US010988743B2

(12) United States Patent
Inui et al.

(10) Patent No.: US 10,988,743 B2
(45) Date of Patent: Apr. 27, 2021

(54) CORYNEFORM BACTERIAL TRANSFORMANT AND METHOD FOR PRODUCING 4-AMINOBENZOIC ACID OR SALT THEREOF USING SAME

(71) Applicants: RESEARCH INSTITUTE OF INNOVATIVE TECHNOLOGY FOR THE EARTH, Kyoto (JP); SUMITOMO BAKELITE CO., LTD., Tokyo (JP)

(72) Inventors: Masayuki Inui, Kyoto (JP); Kazumi Hiraga, Kyoto (JP); Masako Suda, Kyoto (JP); Takeshi Kubota, Kyoto (JP)

(73) Assignees: RESEARCH INSTITUTE OF INNOVATIVE TECHNOLOGY FOR THE EARTH, Kyoto (JP); SUMITOMO BAKELITE CO., LTD., Tokyo (JP)

( * ) Notice: Subject to any disclaimer, the term of this patent is extended or adjusted under 35 U.S.C. 154(b) by 0 days.

(21) Appl. No.: 16/079,896

(22) PCT Filed: Feb. 24, 2017

(86) PCT No.: PCT/JP2017/007232
§ 371 (c)(1),
(2) Date: Aug. 24, 2018

(87) PCT Pub. No.: WO2017/146241
PCT Pub. Date: Aug. 31, 2017

(65) Prior Publication Data
US 2019/0194629 A1 Jun. 27, 2019

(30) Foreign Application Priority Data
Feb. 26, 2016 (JP) ............................ JP2016-036190

(51) Int. Cl.
*C12N 9/10* (2006.01)
*C12N 9/88* (2006.01)
(Continued)

(52) U.S. Cl.
CPC ............. *C12N 9/1096* (2013.01); *C12N 1/20* (2013.01); *C12N 9/88* (2013.01); *C12N 15/09* (2013.01);
(Continued)

(58) Field of Classification Search
CPC .......... C12N 9/1096; C12N 9/88; C12P 13/02
See application file for complete search history.

(56) References Cited

U.S. PATENT DOCUMENTS 4,500,640 A 2/1985 Katsumata et al.
9,803,223 B2 * 10/2017 Fujikura .................. C12N 1/20
(Continued)

FOREIGN PATENT DOCUMENTS

EP 0 077 548 10/1982
JP 57-183799 11/1982
(Continued)

OTHER PUBLICATIONS

Ruckert. M1Tu99. UniProtKB Database. May 2013.*
(Continued)

*Primary Examiner* — Yong D Pak
(74) *Attorney, Agent, or Firm* — Wenderoth, Lind & Ponack, L.L.P.

(57) ABSTRACT

Provided is a microorganism that is capable of efficiently producing para-aminobenzoic acid (4-ABA) or a salt thereof, using saccharides as raw materials, and a method for efficiently producing 4-ABA or a salt thereof by using this microorganism.
A transformant obtained by introducing, into a coryneform bacterium, a gene that encodes 4-amino-4-deoxychorismate
(Continued)

lyase, a gene that encodes a para-aminobenzoate synthase component I, and a gene that encodes a para-aminobenzoate synthase component II, is capable of efficiently producing 4-ABA or a salt thereof from saccharides.

14 Claims, 2 Drawing Sheets

Specification includes a Sequence Listing.

(51) Int. Cl.

| | |
|---|---|
| ***C12P 13/00*** | (2006.01) |
| ***C12N 1/20*** | (2006.01) |
| ***C12N 15/00*** | (2006.01) |
| ***C12N 15/09*** | (2006.01) |
| ***C12P 13/02*** | (2006.01) |
| ***C12N 15/77*** | (2006.01) |

(52) U.S. Cl.
CPC ............ *C12N 15/77* (2013.01); *C12P 13/001* (2013.01); *C12P 13/02* (2013.01)

(56) References Cited

U.S. PATENT DOCUMENTS

| | | | | |
|---|---|---|---|---|
| 2007/0087423 | A1 | 4/2007 | Murakami et al. | |
| 2011/0097767 | A1* | 4/2011 | Pharkya ................. | C12N 15/52 435/128 |
| 2013/0203139 | A1 | 8/2013 | Yukawa et al. | |
| 2014/0371418 | A1 | 12/2014 | Ng et al. | |
| 2017/0211104 | A1* | 7/2017 | Anderson ............. | C12P 13/001 |
| 2018/0044688 | A1 | 2/2018 | Inui et al. | |

FOREIGN PATENT DOCUMENTS

| | | |
|---|---|---|
| JP | 58-67699 | 4/1983 |
| JP | 62-166890 | 7/1987 |
| JP | 2006-124440 | 5/2006 |
| JP | 2015-15 | 1/2015 |
| WO | 2005/010182 | 2/2005 |
| WO | 2012/033112 | 3/2012 |
| WO | 2013/103894 | 7/2013 |
| WO | WO-2014171205 A1 * | 10/2014 |
| WO | 2015/124687 | 8/2015 |
| WO | 2016/027870 | 2/2016 |
| WO | 2016/053649 | 4/2016 |

OTHER PUBLICATIONS

Riley. NC 000913.3. NCBI Database. 2006.*
International Search Report dated Apr. 18, 2017 in International Application No. PCT/JP2017/007232.
Jens O. Kromer et al., "Production of aromatics in *Saccharomyces cerevisiae*—A feasibility study", J Biotechnol (2013) 163: 184-193.
Daisuke Koma et al., "Production of p-Aminobenzoic acid by metabolically engineered *Escherichia coli*", Biosci Biotechnol and Biochem; 2014, vol. 78, No. 2, 350-357.
Bergey's Manual of Determinative Bacteriology, vol. 8, 599 (1974).
Liebl, W. et al., "Transfer of *Brevibacterium divaricatum* DSM 20297T, "*Brevibacterium flavum*" DSM 20411, "*Brevibacterium lactofermentum*" DSM 20412 and DSM 1412, and *Corynebacterium lilum* DSM 20137$^T$ to *Corynebacterium glutamicum* and their distinction by rRNA gene restriction patterns", Int J Syst Bacteriol. 41:255-260 (1991).
Kazuo Komagata et al., "Amino Acid and Nucleic Acid No. 56", 45: 944-963 (1987).
Ya-Jun Liu et al., "*Corynebacterium glutamicum* Contains 3-Deoxy-D-Arabino-Heptulosonate 7-Phosphate Synthases That Display Novel Biochemical Features", Appl. Environ. Microbiol., 74; 5497-5503 (2008).
Kitzing K. et al., "Spectroscopic and Kinetic Characterization of the Bifunctional Chorismate Synthase from *Neurospora crassa*", The Journal of Biological Chemistry, vol. 276, No. 46, Nov. 16, 2001, pp. 42658-42666.
Wen-Chi Cheng et al., "Structures of *Helicobacter pylori* Shikimate Kinase Reveal a Selective Inhibitor-Induced-Fit Mechanism", PLoS One, 7: e33481 (2012).
Meudi, S. et al., "Dehydroquinate synthase from *Escherichia coli*, and its substrate 3-deoxy-D-arabino-heptulosonic acid 7-phosphate", Methods. Enzymol. 142: 306-314 (1987).
Miwa, K. et al., "Cryptic Plasmids in Glutamic Acid-producing Bacteria", Agric. Biol. Chem. 48: 2901-2903 (1984).
Yamaguchi, R. et al., "Determination of the complete nucleotide sequence of the *Brevibacterium lactofermentum* plasmid pAM330 and the analysis of its genetic information", Nucleic Acids Symp. Ser. 16: 265-267 (1985).
Kurusu, Y. et al., "Identification of Plasmid Partition Function in Coryneform Bacteria", Appl. Environ. Microbiol. 57: 759-764 (1991).
Katsumata, R., et al., "Protoplast Transformation of Glutamate-Producing Bacteria with Plasmid DNA", J. Bacteriol., 159: 306-311 (1984).
Eikmanns, B.J. et al., "A family of *Corynebacterium glutamicum/Escherichia coli* shuttle vectors for cloning, controlled gene expression, and promoter probing", Gene, 102: 93-98 (1991).
Kurusu, Y., et al., "Electroporation-transformation System for Coryneform Bacteria by Auxotropic Complementation", Agric. Biol. Chem. 54: 443-447 (1990).
Inui, M. et al., "Metabolic Analysis of *Corynebacterium glutamicium* during Lactate and Succinate Productions under Oxygen Deprivation Conditions", J. Mol. Microbiol. Biotechnol. 7: 182-196 (2004).
Omumasaba, C.A. et al., "*Corynebacterium glutamicum* Glyceraldehyde-3-Phosphate Dehydrogenase Isoforms with Opposite, ATP-Dependent Regulation", J. Mol. Microbiol. Biotechnol. 8: 91-103 (2004).
Pfennig, N. et al., "The Dissimilatory Sulfate-Reducing Bacteria", In the Prokaryotes, A Handbok on Habitats Isolation and Identification of Bacteria, Ed. by Starr, M.P. et al., p. 926-940, Berlin, Springer Verlag (1981).
Nougei Kagaku Jitsukensyo 3, No. 26 (1990).
Hasegawa S. et al., "Improvement of the Redox Balance Increases L-Valine Production by *Cornebacterium glutamicum* under Oxygen Deprivation Conditions", Appl Environ Microbiol. 78(3): 865-875 (2012).
Masayuki Inui et al., "Metabolic Engineering of *Corynebacterium glutamicum* or Fuel Ethanol Production under Oxygen-Deprivation Conditions", J Mol Microbiol Biotechnol. 8(4): 243-254 (2004).
Nobuaki Suzuki et al., "Large-Scale Engineering of the *Corynebacterium glutamicium* Genome", Appl. Environ. Microbiol. 71: 3369-3372 (2005).
Kubota T et al., "Production of para-aminobenzoate by genetically engineered *Corynebacterium glutamicum* and non-biological formation of an N-glucosyl byproduct", Metabolic Engineering, vol. 38, Nov. 2016, pp. 322-330.

* cited by examiner

Changes with time of glucose concentration
in reaction solution of wild strain of *Corynebacterium glutamicum*
under the presence of para-aminobenzoic acid.

Changes with time of production of para-aminobenzoic acid

SEQUENCE LISTING

```
<160> NUMBER OF SEQ ID NOS: 211

<210> SEQ ID NO 1
<211> LENGTH: 1266
<212> TYPE: DNA
<213> ORGANISM: Shewanella woodyi

<400> SEQUENCE: 1

atgctccccg gcatcttcga cgcgcctcac gacgaccctg cttccgtcac acgccttggt      60

tacagctcac tggaccccgt cgatgtgggt gtatcacttc ttatcgacga cgacctcccc     120

gcgatggcta tcggtgcctg gggtgagctc gaggccgtca tcgcaccgga tgcgttatgc     180

acctactgcg atccggacga ggcattagcg cccccacctg gagttttcgc tgcttccgcc     240

agcccttctg acaacgacga tgaatcgacg gagaccgctt ctgatccccg caatggcgtt     300

cgttttggtt tcatctcgta ccccgacccc acggtgtatg ccgcgggcgt taccgctcac     360

caggtgatat ggcgacgcga cggggaatgg ctcaccaacg gcgaccccga ttgggctgcg     420

ggaatcctcg ctacggcgga tcatcgtcgc cactatcact ccgctgacga ggtctcccta     480

cccacgcact ggagcaccgg cgacagggag gcccatcgcc ggggtgtcct cagctgcctg     540

gacgccattc gcgccgggga ggtctaccaa gcgtgcatct ccgctcagtt tcggacgcca     600

atgacgtcgc gcgccgaggc cgcccggtgg tggctctcga ctgtccatcg cacccgcccc     660

aggtacgcga tgttcctggc aacaaatgac cgcgccattg cctcgctgag ccccgaactg     720

tttctggaac gcaggggctc cacggtgtgg tcgtcgccaa ttaaagggac tattcccatc     780

gatcgcgatc ccgaggaact cgcgcggagc aggaaggatg ttgcggagaa catcatgatt     840

gtggaccttg tccgcaatga cctcagccgc gtgtgcaggg atgtgaccgt gccctcgttg     900

ctgaaggtcg tcccggcacc gggggtgtgg catctcgtat cgacggtgtc tgggcaggtg     960

gacgatgtgt cgccggcgcg ggattcccgc attatcgatg cctgtttccc gccggcgtcg    1020

gtgacgggca caccgaagtt acgggcgcgg gaatatctgg ccgagtggga gccggtggcg    1080

cgcggtattc attgtggaac agtggggata aactggggag atatcgtggc gaatgtggcc    1140

attcgcaccg cggaatgggt gaatggcgag ctggttttgg gcaccggcgg cgggatcacc    1200

attgactcca ctcccgacgc tgaatgggct gagatcatga ccaaaacgtc gactttacgc    1260

tggtag                                                               1266

<210> SEQ ID NO 2
<211> LENGTH: 810
<212> TYPE: DNA
```

-continued

<213> ORGANISM: Escherichia coli

<400> SEQUENCE: 2

```
atgttcttaa ttaacggtca taagcaggaa tcgctggcag taagcgatcg ggcaacgcag     60
tttggtgatg gttgttttac caccgccaga gttatcgacg gtaaagtcag tttgttatcg    120
gcgcatatcc agcgactaca ggatgcttgt cagcggttga tgatttcctg tgacttctgg    180
cctcagcttg aacaagagat gaaaacgctg gcagcagaac agcaaaatgg tgtgctgaaa    240
gtcgtgatca gtcgcggtag tggcgggcga gggtacagca cattgaacag cggaccggca    300
acgcggattc tctccgttac ggcttatcct gcacattacg accgtttgcg taacgagggg    360
attacgttgg cgctaagccc ggtgcggctg gggcgcaatc ctcatcttgc aggtattaaa    420
catctcaatc gtcttgagca agtattgatt cgctctcatc ttgagcagac aaacgctgat    480
gaggcgctgg tccttgacag cgaagggtgg gttacggaat gctgtgcggc taatttgttc    540
tggcggaagg gcaacgtagt ttatacgccg cgactggatc aggcaggtgt taacggcatt    600
atgcgacaat tctgtatccg tttgctggca caatcctctt atcagcttgt cgaagtgcaa    660
gcctctctgg aagagtcgtt gcaggcagat gagatggtta tttgtaatgc gttaatgcca    720
gtgatgcccg tatgtgcctg tggcgatgtc tccttttcgt cagcaacgtt atatgaatat    780
ttagccccac tttgtgagcg cccgaattag                                     810
```

<210> SEQ ID NO 3
<211> LENGTH: 816
<212> TYPE: DNA
<213> ORGANISM: Escherichia fergusonii

<400> SEQUENCE: 3

```
atgttcttaa taaatggtca aaaacaaaca tggctggccg cgagtgacag agcgacgcag     60
tttggtgatg gatgtttcac caccgcacgt attcaggatg gacatgtaat tatgctcaca    120
gagcatatcc ggcgattaca ggatgcctgc attaaattga tgattacctt tgagcagtgg    180
gagttactgc aactggaaat ggaaactctg gcaagggaac ataaaagtgg tgtgcttaag    240
gtgattatca ctcgtggtag tggtggtcgt ggttacagtc ctggcagttg tcactcacca    300
ggccgaattt tgtccgtttc tgcatatcca gagcattatt cccgctggcg acagaaggga    360
attacgctaa ctctcagccc tgttcgcctg ggccgcaatc ccttacttgc aggaattaag    420
catcttaatc ggctggagca agtgttgatc cggacacatc tcgatcagac aactgctgac    480
gaggcacttg ttcttgacag cgaaggatgg gttacggaat gctgcgcagc taatttattc    540
tggcgacagg gaaatgtggt ttatacaccg agccttgaat atgccggtgt gaagggcatt    600
atgcgacaat tctgtatcca tttattggca caatcttctt atcgtgttgt cgaagttcag    660
gctcgaccgg aagaggtaat ggcggcagat gaaattttgc tttgtaatgc gctgatgccc    720
gtcattcccg tacgcacctg tggtgataag ttgctgtctt cgagacaatt atttgagttt    780
ttagccccac tttgtgagca cccgaattca ttatga                               816
```

<210> SEQ ID NO 4
<211> LENGTH: 870
<212> TYPE: DNA
<213> ORGANISM: Saccharophagus degradans

<400> SEQUENCE: 4

```
atgctcgaac ctgttgtctc acttgttaat ggtgttaaaa cccaacaaat cgacattcaa     60
aatagaggaa tggcgtttgg cgatggggtg ttcgaaacaa tgcgccttac tcaaggccac    120
```

-continued attcctctac tagaccttca taaagcaagg ctgcacgtcg gtattaaaac gctcggctta 180
aactacagtg aagcggcttt aaataaacac ctcgcacagc tgtttagtat tattaacgac 240
tctaatattg catccggtcg cgttaagctt attgtagcca ggggccaagg gggccaaggg 300
ggccaagggg gccaaggggg gcagggggtt aacccttcgc ctgatgcagg cgtagatgta 360
agtattcttt tgtacgccag ccaattagcc gcttgggtgc agccagcggt tgcgctaaaa 420
accagcagag tacagttacc ccataatgta aacctagccg gtataaagca ccttaaccga 480
ttggattacg tactagcggc acaagctgca atgcccgccg aaaatgagca ggtattattg 540
ctagatgttg caaataactt aatagaaacc gtacatcaca atgtgttttt tattcgcggt 600
agcgaagtga ttacaccatc gcttgctcgt tgcggtgtaa acggcgtgtt taagcagtgg 660
ttagtgaatt cggtaattcc aaaagcgggg ctgcaattag tcgagcgcga aattagccga 720
gtagatgcag aagcttgcga cgcgtgcttt attaccaacg cttactcggg gttaacacct 780
gtaacagcaa taaatgggca cctatttaat agctgtgaaa aattaaacgc tataactggc 840
gaaattaacc aaatattggg tgataaataa 870

<210> SEQ ID NO 5
<211> LENGTH: 816
<212> TYPE: DNA
<213> ORGANISM: Shewanella woodyi

<400> SEQUENCE: 5
atgacacaag tgtgggttaa tggtgtgctg gccaaagaga tcgacccgtt agacagagcg 60
atagcatacg gtgatggtct gtttgccaca atgcgcattg ctgctggaga gatacagttt 120
ctatcggcgc accttgccag attaactcag ggagccaagc gtttaggttt tacttggttt 180
gcttcacaag agcttcaaag tctgcttaag tcatcggcgt taactcaggt taacggctgt 240
gttaagttgc tgctcagtcg cggtgttggt ggccgaggtt acgccgcgcc agatgcttgc 300
ggtattaatg aggtactctc actttatgag ttgccgcaac attacgctca ttggcaaagc 360
gagggcgtat cactgagctt gagtgaggtt aaattagcaa agcagccaag gcttgctgga 420
attaaacacc ttaaccgcct agagcaggtg ctgatcaaat cgacggcgct accaagctcg 480
tttgatgact ggctagtgct cgacagtgat agccaagttg ttgaatcatc catggctaac 540
ctcttttttg ttaagaataa aactgttttt accccagcga ttagccactc aggcgttgcc 600
ggagtgatga gggaacaatt gatttttgct ttagttgagt ctggttatca tattgatatt 660
aagcagataa gctatgccga tattaacaag ttcgatcact gttttatgac caatagcctt 720
tttgggctgg tggatgtaaa ccgtattggt accatcaact attctaaata ttcactttca 780
gacagattga gaaatactct gcaacttacc ctatga 816

<210> SEQ ID NO 6
<211> LENGTH: 930
<212> TYPE: DNA
<213> ORGANISM: Arthrobacter phenanthrenivorans

<400> SEQUENCE: 6
atgacttctc cggcttccgt ggttctcgtt ttcctcgatc ctgatttccc ggacggcagg 60
ctggccgacg cttccaagcc ccagctcctg gtcaccgacc agggcgccac ccgcggggac 120
ggcatcttcg agaccatgct ggcggtgggc ggcacggtcc ggaagctcca ggcgcacctg 180
gaccgcctgg ccggctccgc agccgcgctc gacctggtga tcccaagtga gcaggagtgg 240

-continued cggcgcgcca tcacccatgc tgtcgcccag caccgttcgc agcacccgcc cgcctcggcc 300
gcggcggacg aactggtggt caagctggtg gtgacccgcg gtgtcgaggg tgcgtccgca 360
cccaccgcct gggtccaagc atcaccggtc ggggccggcg cccggcgcca gcgtgaggcc 420
ggcatcgacg tcatcctcct ggaccgcggc tatgacagcg gcgcagccga gcgcgccccc 480
tggctgctgc tgggcgccaa gacgctgtcc tacgccgtga acatggcggc gttgcgccac 540
gcccagaaac agggcgctga cgacgtcatt ttcatctcaa ccgacggccg cgtcctggaa 600
gggcccactt ccactgtcct gatggcccac gcagggacgt ccgacgacgg cacttccgtt 660
aagcgcctca tcacaccgca actggacagc ggcatcctgc ccggaacctc ccagggcgcg 720
ctgttcgctg ctgccaaggc ggcgggttgg gaacttggct acggcccgct ggagccgcag 780
gacctgctgg atgccgacgc cgtatggctg atttccagtg tccgcctgct ggcgccggtg 840
aaccggatcg acggcaagga agtgggtacc gcgtccgtcc agaaagagct caccgcggaa 900
ctgaacgagc tgttggcggg catacagtaa 930

<210> SEQ ID NO 7
<211> LENGTH: 792
<212> TYPE: DNA
<213> ORGANISM: Anabaena variabilis

<400> SEQUENCE: 7
atgttctggt acaacggtaa gctaattaat tcccaaacct tggagttaga tatttatgat 60
cctgggttac tttatggggc aactattttt accacactgc gaatttatgg gcattctctc 120
gatcatagtt taactagttg gcaggcacac tgcgatcgcc tccacacttc cattcgatct 180
ttcgcttggg aacaaccaga ctggaaccgt atccgccaag gtgcagaaat actgttaact 240
catttccccg ttctcagaat cactattttt cctgatggta gggaatggat aattggcagg 300
tatttacccc agaatttatt agaaatccaa aaatatggcg tatcttgcac cattgctgaa 360
ccagaaatat atcgtagttt gccttctcat aaaactggta actatctgag tgcgtggatg 420
gctaaaactt atgcggcaaa gttaaactcc caagaagcaa ttttagtgaa tacagccgga 480
aattggctag aaaccaccac aggcaacctt tggggatggc aaaatgggag ttggtggaca 540
ccacctttaa cagagggaat tttaccgggg attggacgac agcagctaat ccactggctg 600
caaactcatc aacaaacggt gcgggaggag ccttggacat ctgagctagt caacggtttt 660
gaagcgatcg cctacactaa tagtgtggtg gaagttattc ccatacatac cgtttaccag 720
cccacagaat cgttacaata tgatccctac catccacgct tgcaaaaact tagggaacta 780
ttcttagcat ga 792

<210> SEQ ID NO 8
<211> LENGTH: 816
<212> TYPE: DNA
<213> ORGANISM: Azotobacter vinelandii

<400> SEQUENCE: 8
atggcctgct ggatcgacgg ccggcccgat gagccgctac ctccgaccga ccgtggtctg 60
gcctatggcg atggcctgtt cgagaccatc gccgtgcgtc gagggcagcc gctgctgctg 120
gagcggcacc tggcgcgtct gggcgagggc tgtgccaggc tggcgcttcc cggcgacccg 180
gcctcgatcc gcgccgaact gctggccttt tcggccgcgt tgggcgaggg cgtggccaag 240
ctgctgctga cccgcggcga cggtctacgc ggttatgcgg ccccccagcc gccgcagtcg 300
cggcgcatcc tcctgggcag tccgccgccg cggtatccgc cgggcaatgc cgcgcagggc 360

-continued

```
gtgcggctct atccctgccg tacccgcctg gccgagcagc ccctgctggc cggactcaag    420

catctcaatc gcctggagca ggtgctcgcc cgcgccgagt ggcgggatgc cgagcacgcc    480

gaaggactga tgcgcgatct gtcgggacgg gtgatcgagg gggttttcag caacctgttc    540

ctggtcaggg acggtgtcct gctgaccgcc gacctgtgcc gttgcggggt ggccggggtc    600

atgcgcgcgg aaatcctcga acaggcggaa cgggcgggca tcgcgctgca ggtacgtgac    660

atcgacttcg ccgagctgct ggcggcggac gaggtttttc tctgcaacag tctctatggc    720

atttggccgg tccgccggtt cgaagaacac gactggccgg tcggcacgct cacccgtaaa    780

ctgcagggct cgatccgcaa gctactggac tcctga                              816
```

<210> SEQ ID NO 9
<211> LENGTH: 636
<212> TYPE: DNA
<213> ORGANISM: Ochrobactrum anthropi

<400> SEQUENCE: 9

```
atggagccgg attatcagct gatcgaaacc atgcgctggg agccgctctc gggcgtttta     60

cgcttcgatt tgcatatggc gcgtctcgaa aattccgccc gtgaactcgg tttttcctgc    120

aatatggaag ctgtccggca gaaggtttca gaaagcggaa ccggtgagca ggccctgaag    180

gtgcggctga cacttgcgcc cgatggcgtg accactgtct cgaccatgcc ttttgaacca    240

ctctcctgcc agacgatctg gcgaatcgcg attgcccgca cgcaccttga tcacaatgat    300

actctgttgc gccacaagac gacgcgacgg caggcctata tcgcagcacg cgaagagtat    360

tcaacggcag agatcgacga agtcatcctg ctcaatgatc gcggcgaagt ctgtgaggga    420

accattacgt cgatatttct cgatgtaggc ggcacgacct gcacgacgcc cgccctgtca    480

tgcggcctcc tcgacggggt tctgcgccgt gaattgctga acaacaatgt tgtcgaagag    540

ggtatcgtta ccgtcgaaac gctcaaaaat gcgcgcaaca ttctcgtcgg caattcgctg    600

cgcggcatga tccgggcaca gctgatcgag gcttaa                              636
```

<210> SEQ ID NO 10
<211> LENGTH: 732
<212> TYPE: DNA
<213> ORGANISM: Clostridium beijerinckii

<400> SEQUENCE: 10

```
atgagaagga tagttcataa ttatgataaa gtaatgcttg acgatggagt attttttgga     60

agaggaatat ttgaaacaat tctttgtaat gagaaaccta tatatttaga agagcattta    120

cagagattaa aaaaagatat gttggagtta aatttacagc cattagtgga agaaaaattt    180

ttaagagatc atttaagtaa gttggagata aaaaacaaag tattaaaaat aactgttaca    240

cctttaaaca ttataataac cgaaagagaa attgcatata aaaatgacga ttataaaaaa    300

ggaatgtcgt taacaatttc caaggtaaga cgtaacagta cttcaagatt ggcctctatc    360

aaatctacat gctatataga aaacataatt gaaaaagaga atgctaagaa attaggatac    420

gatgatgtga tatttttaaa tgaaaaaggt aatgttacag aaacgagttg tgcaaatata    480

tttatgataa aaaataatga aatttttact ccaaatagtg aagatggatt attaaaaggt    540

ataataagag ataagattat gaaaaaattt aaggtaaccg aaaaaagtat cactatagat    600

gatctaacac attcggaaga ggtaattata acaaatagca taatgggggc aatgtctata    660

aaacagatta atgaaactaa atataatagt gaaaagttta gacatatatt taatgaaaat    720
```

ttgaggagtt ag 732

<210> SEQ ID NO 11
<211> LENGTH: 873
<212> TYPE: DNA
<213> ORGANISM: Xenorhabdus bovienii

<400> SEQUENCE: 11
atgtctgagg ttatcacgcc ttcttatcga aaattagaaa atgaaatgat gtattggatt 60
aatggcaaac cgtgtaatca attacctgtt aatgatcgtg cggtacaatt tggtgatggc 120
tgttttacaa caataagagt tgagcaaggg caggcagctt tgctaccttt gcacataaaa 180
cggttacaaa aaggcgttga aaaactgttt atgccagcac tggattggct gcaacttgag 240
gatcatatta agcaggtggt taccggctgt gaatccggta ttctgaaagt tattctctcc 300
agaggagttg gtggtcgtgg ttatggtatt agtgatgcta tcgagccaaa tcaggttctc 360
tcgttgagtt catatccaga acagtatgtt atccagcgta aaaatggtat ttcactcgtt 420
cttagcccaa ttgttatggg tatcaatccc catttggcgg gtattaaaca cttgaaccgc 480
ttggaacagg ttctgataaa aagattcatt gagcagtcaa aggctgatga agcactggtt 540
cttgatagtg atggcttact ggttgagtgt tgtactgcta atattttctg gcgaaaaggt 600
aaaaacgttt atacgcctga tttgaatcaa tgtggtgtag aaggggtgat gcggcagaag 660
attatgcaat tattggcaga aagtgattat aacctgtcat gtgtcatgcg ttatcctgag 720
gtattagctc atgctgatga ggtgattatc tgcaattcct tgatgcctgt tatcgcagta 780
aaccaaattc aggcgcataa aaatcagcct gcatggaaat atcaatcaag agaattgcat 840
gagtatctat tgcctggatg tttaaggctg tag 873

<210> SEQ ID NO 12
<211> LENGTH: 858
<212> TYPE: DNA
<213> ORGANISM: Bacillus pseudofirmus

<400> SEQUENCE: 12
atgatgatgt atgtagatgg tgaactcgtt tcaggcgaac aagcgaaagt gtctgttttt 60
gaccatggtt acatgtatgg attagggttg tttgagacgt ttcgtgtata taatggtcat 120
ccttttctgt tggatgacca ttttcgccgt ttgcaagaag gattacatat tcttggcata 180
gagtgggaga tgacccgcca ggatgtaatc cgtgtcatag acgagctgat tagcgccaat 240
caatatcaaa accaagatgt gtatgtaagg tggaacgttt ctgcgggtga taagggactt 300
ggcctttata cggggcaata taccgaaccg gtaactgtag tatatacgaa gtcgctctct 360
agacagatgg gccgagaaaa acaaggtgtc attttaaaga cgagacgcaa tactcctgaa 420
acgaagatgc ggttgaagtc acatcactat ttgaataata ttatggctaa acgagaaata 480
ggatctgacc cttcagttga aggcatcttt ttaacggagg atggctatct agcagagggg 540
attgtttcga acttattctg ggtaaagaac ggtatcgtgt atacccccctc tattggtacg 600 ggtattctga atggtataac gagacagttt ataatcaggg tacttgaaga gtgcggctat 660
gcagtaaaaa cgggaagata tcataaagaa gagctctatg aggcagatga agtgtttgtg 720
actaattcta tacaagaagt tgtctctctt acaagtgtcg accgtcagac gtatgattca 780
aaacaagcca taacaaggga gctgcaacaa aggtacaagc tatacagcaa gaaactttgg 840
agcaagagtg agttataa 858

<210> SEQ ID NO 13
<211> LENGTH: 756
<212> TYPE: DNA
<213> ORGANISM: Caulobacter crescentus

<400> SEQUENCE: 13
atgacgagac ctgacgctgt tcccctgaac gatcgcggcc tgctgctggg cgatggcctg 60
ttcgagacga tgctggcgca ggacggggcg gtggcgcacc tgccggctca tcttgaccgg 120
atggccgccg gctgcgccgt cctgggcctg ccgttcgatc gcgaggcggc ccagcgtctg 180
gtcctcgccg ccgcgccgtc gcagggacgc tttgcgatcc gcctgaccct caccgccggc 240
tcgggcggtc gcgggcttga tcggcccgag gcgccggctg tccggctctt cgcccacggcc 300 gcgccctcga cgccggtgac gacgccggcg acgctgatcg tggcggccac gcgccgcaac 360
gagggctcgc cggcctcacg cctgaagacg ctcgcctatc tcgacaatgt cctggcccgg 420
gccgaggcgc gggccgccgg ggccgatgac gcgctgatgc tgaacaatcg cggcgagatc 480
gcctgcgcgg cggcggccaa cctgttctgg ctggcgggcg gtcgcctgtt cacgccgcgt 540
ctggactgcg gggtcctggc ggggaccacc cgcgcccgac tgctggcccg cgaagcggtg 600
gaagaggtcg ccgtgggcgt cgaagcgctg gaggccgccg aggcggtggt gctgaccaac 660
agcctgatcg gcgtgcggcc cgtgtcgcgt ctgggggagc gggcgctgcc cgagcacccc 720
ctggcggcgc ggctgaacgc gcgtctggac gcctag 756

<210> SEQ ID NO 14
<211> LENGTH: 813
<212> TYPE: DNA
<213> ORGANISM: Synechococcus sp.

<400> SEQUENCE: 14
atggtcatgg gctattggta cgcgggggct tggtacgagg ggacagaact gactctcccg 60
gttagtgatc cgagtttttt atttggggcg accctcttta cgaccctccg ggctcaccaa 120
aactccctca cggatccccg cagtctgtgg tctcaccatg gcgatcgcct ccgccacagc 180
attaaaactt tgcaatggcc agcacccgat tgggagcgca ttaaccaggg cgcccaaaaa 240
gtggccaccg tcgcccccgt ggtgcgggtg acaatcctcc atgatggccg cgaactgatc 300
ctcggccgtc cactgccgga acatttagcc caacagcagc agcagggaat ccaaggttgg 360
ttggcccaag acccctactt ccagagaccc caggcggatt ttaaaacagg caattacctc 420
agcgcgtggc aggcccgcca acgggcgatc gccttggggg ccggagaagc aattttgcca 480
gatcccagcg gccactggct cgaaaccgcc accggaaatt tatgggggtt taaacaagga 540
acttggtaca cgccgcccct agggggaatt ttgcctgggg tgatgcgatc gcacctccta 600
gggcaactgc aaaaacacca aatacccgtc caggaaattc cttgggacat tgatttgatc 660
caaaccttcg aggcgatcgc ctacagcaac agcgtcgtgg gcgtgattcc tttccaagca 720
attcagggag caaatttttc cttaaacgct ctccaaatca accatccagc cctgcgccac 780
ctccagcatt tgagcggtca actggtcgtg taa 813

<210> SEQ ID NO 15
<211> LENGTH: 597
<212> TYPE: DNA
<213> ORGANISM: Bacteroides thetaiotaomicron

<400> SEQUENCE: 15
atgtgccaat ttattgaaac gattcgcata gaagacggac aggtttataa tctgtcgtat 60

-continued

```
cacacagcgc gcatgaaccg gactcgtgcc gccttttgga aagaagcggc tcccattgat    120
ttgtccggct ttatatctcc tccgtctctg tccggtatct ggaagtgccg gattgtgtac    180
gataaggaaa tcgaagaggt cggatacact ccttatcaaa tgagaatggt ttcttccttg    240
cgtccggttg cttcggacac tattgattat agttacaaga gtaccaatcg ggaagaattg    300
aatgatctgt ttgcccggag agggaaggca gacgatattc tgatagtgaa agacggatat    360
ctgactgata cctccattgc caacatagcg ctgtatgacg gacatacatg gtatactccg    420
gctcatccct tgcttcaggg gacgaagcgt gcggaactgt tggataatcg gttcatagtg    480
gagaaagata tccggcaggc gcaattgggc gattactccc atatcatgtt gttcaatgcg    540
atgatagact ggaaacggct catcatacct gtcaatgaaa aatattttat tctataa       597
```

<210> SEQ ID NO 16
<211> LENGTH: 813
<212> TYPE: DNA
<213> ORGANISM: Ferrimonas balearica

<400> SEQUENCE: 16

```
atgacacgct ggctcgacgg ccggccaacc gcaacggttc ccggcgacga ccgtggcctg     60
actctcgggg atggccactt caccaccatg ctggttcagc agggtggggt ggtgctctgg    120
cagcgccatc aaacgcgact ggctgaagcc aatgaccgat tgggttttgc ccagccggac    180
tggcatcaac tggaagccga gattcagcag gccagccagg gcgttgagct cggttgcctg    240
cgcctgaccc tgactcgcgg cagtgcgggc cggggctatc agggccaatg gctggcggtt    300
ccccgccgat tgttggccct ctccccttt ccctcccact accgtcaatg gcaacaacag     360
ggcgtcgatg ctgaggtggc tgaactcact ctggcgacgg ggggcccgct ggttggcctg    420
aaaaccctcg ggcggctgga gcaggttctg atcaagcagg aagcggcgag tcgaaacgtc    480
gatgagttgc tggtttgtga tggccatggc cacctggtgg aagccagtgc tggcaacctg    540
tttctggtgt ttgctgatgg caccgtcgta accccaagcc tgtcggaatg cggcattgcc    600
ggcgtcatgc gcgcagaggt tatggcgttg ctggcccagt ccgggttgaa ggtggtggaa    660
cgcccggtcc gggtggaaga gttaaccgat gtggccgaag cctttgtcac caatgccctg    720
atgggcgtga tgccgctgcg ccatatcgga gagaaacgct taaaccgcca actggcggat    780
ctgttattgg agagccatca attatggcgt taa                                 813
```

<210> SEQ ID NO 17
<211> LENGTH: 564
<212> TYPE: DNA
<213> ORGANISM: Enterobacter cloacae

<400> SEQUENCE: 17

```
atgattctgc tgattgataa ctacgattcc ttcacctgga acctttacca gtatttttgt     60
gaactgggtg cagaggtggt tgtccgccgt aacgacgaca tcagcctgac cgagattgac    120
gcgctggccc cgaagaaaat cgttatctcg ccggggccgt gtaccccatc ggaatcgggt    180
atttctctgg atgtgatccg ccactacgcc ggcaggctgc cgattcttgg cgtctgcctt    240
ggccatcagg ccatcgggca ggtgtttggc gccaccatcg tccgcgctgc cagggtgatg    300
cacggtaaaa cctcaccggt tacccacacc ggcacgggcg tgtttagtgg gttaaataac    360
ccgttaaccg tcacgcgcta ccattctctg gtgattgacc cgccgacgct gcccgactgc    420
tttgaggtga ccgcctggag cgagacgcag gagatcatgg gcattcgcca tcgtgaatgg    480
gatctcgaag ggtgcagtt ccacccggag agtattctca gcgaacaggg gcaccagctg     540
```

ctggctaatt tcctcaatcg ctga 564

<210> SEQ ID NO 18
<211> LENGTH: 1863
<212> TYPE: DNA
<213> ORGANISM: Conynebacterium callunae

<400> SEQUENCE: 18
atgcgcgttt taattgttga taattatgat tcatttacct tcaaccttgc cacttatgtg 60
gaagaagtga caggtcaggc gccaacagtg gtgcgcaatg atgacattat tgatgagacg 120
cttttcgacg ccgtcatcct ctcacccggt ccaggtcacc ccggagtgct ggcagatttt 180
ggtatctgta ctgggattat tgaacgcgcg caggtgccca ttttgggtgt ttgcctgggc 240
caccagggca ttgcgctggc gcacggcgcc cgcgttgagt tggcaccaac cccggtgcat 300
gggcaggttt ctaccatcag ccacaacgac agtgcgcttt tcgacgccat cccgcgcgac 360
tttgatgtgg tgcgttatca ctccatgatt gcctcagatt taccggattc tgtggaagca 420
actgcctgga ccgccgatgg tttgatcatg gcattgcaac acaaaaccct gccgcaatgg 480
ggagtgcaat tccacccaga atccattggt ggacagtggg ggcatcagat tattcgtaat 540
tttttgcatg ctgcccgtag ttatcactgg gaaattcaag aggaagtact tgaaatctca 600
gtggatccag cgcgcgtttt tgccactcta tatggcgccg ctgaacaagc attttggcta 660
gatgacgcag ctggcactag ctatttaggt gatgccagcg gaccattagc tcgcactaaa 720
acttttaggg taggcgaggg agacttcttc gaatggcttg ccgcggatct tgctaaaaac 780
actgtcgccc caggtgaggg ctttaggctc ggctgggttg gctatgtggg ttatgaactc 840
aaggctgaat gtggagcaca agccgagcat cgctcaaagc tgcccgatgc acaccttatt 900
tttgccgatc gcgctttggc cattgaaaag gatcgagttc gcctactgtc cttgcaagct 960
gatgcgcagt ggtcggcgca ggtcgaggct gccctgaagc aattgcagcc tgcgccagct 1020
gcgcagatca aacccattga actgcaggtt cgtgatagtc gtgagcagta tttggataag 1080
attgcaaagg ctcaggactt gattcggcga ggagaatctt atgaaatctg ccttaccact 1140
cagttgtcag gggagtgcac acaagatcct tttgaactgt atttagcact gcgcgcggaa 1200
aatccaactg cctatgggtc tttcctaaaa tttggtgaaa ccgccatttt gagctcctca 1260
ccagagcgtt ttatcaccat cgatgctggt gggcgcgtgg agtctaagcc gattaaaggt 1320
actcgcggac gtggtaaaaa tgcggctgag gatgccgaaa tcattaagga attgcagagc 1380
aatccaaaag atcgcgccga aaacctcatg atcgtggatt tggtgcgcaa tgatcttgcc 1440
cgtggcgccc agcccatcac cgtgaaaacc gagaagcttt tcgacgtaga aaccttcgcc 1500
acggtgcacc aattggtaag tacggtttct gcacaattag gtgagaagaa cgccattggc 1560
tgtattcggg cggctttccc cggtggctca atgactggtg cacctaagtt acgaaccatg 1620
gaaattattg atgccctgga ggctgcacca cgtggcattt actccggtgg tttgggatat 1680
ttctcgttgg atggttcggt tgatctttcc atggtgatcc gtactctggt actccatgcc 1740
ggccacctgg aatatggcgt gggcggtgcg attttggcac tatctgatcc cgctgaggaa 1800
tgggaagaaa tccgcattaa gtccactccg ctgcttaaac tgtttggagt ggaatttcca 1860
tga 1863

<210> SEQ ID NO 19
<211> LENGTH: 1869
<212> TYPE: DNA

<213> ORGANISM: Conynebacterium efficiens

<400> SEQUENCE: 19

```
atgcgcgtac tgatcatcga caattatgat tccttcacct tcaacctcgc cacgtatgtg      60
gaggaggtca ccggtgcggc accgacggtg gtgcccaatg atgcgcagat cgacgagacg     120
ctgttcgacg ccgtcatcat ctcacccggc cccggccacc ccggggtggc ggcggatttc     180
ggcagctgcc gcggggtgat cgaacgtggt ctggtcccgg tcctcggggt gtgcctgggg     240
catcagggca tcgcgctcgc ccacggcggc gcggtgggcc cggcgccggt cccggtgcac     300
ggtcaggtca cccgcatcca ccacgacggg tccgagcttt tcgacgccat cccgccccag     360
ttcgacgccg tccgttacca ctccctggtg gccaccgatc tgccgccgga actggaggtc     420
accgcgagga ccggggacgg gctgatcatg gcgctgcgcc accgcgagct gccccagtgg     480
ggtgtgcagt tccacccgga atccatcggc gggcagttcg ggcaccggat catggcgaat     540
ttcctgagcc tggcgcgtcg acaagcgcac cggtgggaga tcaccgagca tgtggtggag     600
acaagcgtcg acccggcggc ggtgttcgag acgctcttcg ccgggtcgga gcacgcgttc     660
tggctcgatg atccgcaggg caccacctat atgggtgatg cctccgggcc gcatgcacgg     720
atccgcaccc accgggtggg ggagggggag ctgttcgact ggctgcgtga tgatctgcgt     780
cgcaaccgcg tggccccggg ggtgggtttc cgcctggggt gggtgggata cctcgggtat     840
gagatgaagg ccgaatgcgg ggtggacaat cggcacgcct catcgcatcc cgatgcccac     900
ctgatcttcg ccgaccgggc catcgccatc gaacccggcc gcgtgtggct catggcgctc     960
ggtgagcagg gggagtggtt cgcggagatg accgccgccc tggggcagct gcgcccaccc    1020
cgtgccgctg ccgccccggc cgcccagctc accgtccggg atgaccgcga cagctacctg    1080
gacatgatcg cccgcgccca ggagttgatc acccgcgggg agtcctatga gatctgcctg    1140
accacccagc tgcgcgcgga ggtggaggtg gatcccctcg ccgcctatct ggcgctgcgg    1200
gcggccaacc ccacctccta tggatcattc ctgcagctgg gggagatggc ggtgctgagc    1260
tcgtcgccgg aacggttcat caccatcgac gcctccggac gtgtggaatc caaacccatc    1320
aagggcaccc gcccgcgggg cagtaccgag caggaggatg cggccttgat cgccgatctc    1380
accgacaacc ccaaggaccg cgccgagaac ctcatgatcg tcgacctggt ccgcaatgat    1440
ctcgcccgcg gggcgcaacc ggcaacggtg caggtggaga agcttttcga cgtcgagacc    1500
tacgccaccg tccaccagct cgtcagcacc attaccgccc agctggaggg taaggacccc    1560
attgactgcg tgcgggcggc gttccccggt ggttccatga ccggtgcacc gaagatccgc    1620
accatggaga tcatcgacga gctggagacc ggcccccgtg gtgtctattc cggtggcctg    1680
ggctatttct cccttgatgg ggcggtggat ctgtcgatgg tgatccgcac cgtggtctac    1740
acccccggcg tcctggagta cggggtcggc ggggcgatcc tggccctgtc ggaccccgcc    1800
gcagagtggg aggagatccg ggtgaaatcg aggcccctgc tgggtctgct cggggtggag    1860
ttcccgtga                                                            1869
```

<210> SEQ ID NO 20
<211> LENGTH: 2115
<212> TYPE: DNA
<213> ORGANISM: Conynebacterium casei

<400> SEQUENCE: 20

```
atgattcttc tacttgataa tcatgactct tatactttca atctttacca gctcattgcc      60
gaagtagcgg ggcagtctcc tttggtggtt cgtgccgaac acgccgaggg cgaaagcttg     120
```

-continued

```
ccgcagcgag taagcgctgg cgaattcagc catgtggtga tttcccctgg gccgggaacc    180
cctgaagatc cgcaggactt tgacgccgcg cgcgaagtca tcgaagccgc aagcgatatc    240
ccggtgcttg gcatctgcct tggacaccag ggactagctc tcattaatgg ctccgctatc    300
catagagcgc ctgagccgaa acacggattc atcagcacta tccaccacac tggaaccgaa    360
ctattcgcca ctatcccgca agatttcaag gtggtgcgct accactcact gtgcgtggac    420
gatattgata caacgcgcgt ccagccgcag gcgtggtccg aagacggcgt ggtcatggcg    480
ttgaaagtgc tggatcagcc acactggggc gtgcaatttc acccggaatc catcctgact    540
gagcacgggc gaaccttggt ggaaaacttc ctggggcaaa agcccacaac agaaatcccg    600
aaggaaagcg ctccggtagt cccaggccct aaatctgtgc ctgagaagtg gaagcttgaa    660
catcgcgcga tcaccatggc gattgactgc gaggcaactt ttgccaggct aaaagctcac    720
gcacaagatg cattctggct cgactccgca accgcagact taggcgcgga tacggagtca    780
ggacgatatt caatccttgg gactaatgca ggttccaagg ctgcatcgat tcgctatgac    840
atcagcactg ggatggttca agttgcccgc ggcgatgaga ccttcagtgc tgagactgat    900
atcttgtcct atcttcggga actactagct gagtccgtgg cgacccatga cctgccagcc    960
cttccgtttc ttggcggcta tgtcggattt ctaggctttg agtgcaaagc cctcacggtt   1020
gggccagggc tacacagtgc agttactccc gatgcctatt gggtgtttcc gcaggctttt   1080
gtggtctttg atcatcggca ggcaattgca catctatgcg ttgtctatga cgcgatcgag   1140
ggcccaacgg ctgagaccgc ccagctgatg gaatggctcg aagaatcatt agaagacacc   1200
ccgctaccta gttctacgaa gctcgctgcg cacacagcct ctgagctcga cgggcaatgg   1260
cgtctgtcgg cagacgaata cgtggaacga atcggcgaag tagataaagc gctgcgccgt   1320
ggcgacagct acgaagtctg cttgaccgat acctatgaaa cctcggccgc agttgatggt   1380
tgggacttgt accggcagct gcggcgaaac aatcctgcac cttacgcggc ctacctcaag   1440
ctcggcgcct ttggcgacga gttggaggtt ctatcatctt caccggagcg cttcctcaaa   1500
gttgaacaag acggcaccgt ctcgagcaag ccgattaagg gaacgattgc gcgcgcagaa   1560
gaccctgatg aggaccgccg acgcagctac tacctgcaaa cagatccaaa gacgcgcgcc   1620
gaaaatttga tgatcgtgga cctgctgcgc aatgacctgg gccgtgtctg cgaagtcggc   1680
tctgtggagg ttccggtgct catgggagtg gagtctttcc ggactgtcca tcagctggtc   1740
agcaccgtca tgggcaaact aagggccgat gcagatctta tcgatctgct tgaagccacc   1800
ttcccgggtg gttccatgac tggcgcgccc aaagaacgca cgctgagcat cattgattct   1860
ttagaagccg gaccgcgcgg agtatattcg ggcaccatcg gatacatggg actcgacggc   1920
acggcggact taaatattgt tatccgcacc atcgtcaaag ctggcgacaa cctcagcgtc   1980
ggcgctggtg gagctatagt tctcgattct gtcgctgtgg aagaaaatgc cgagaaagaa   2040
ctcaaagcag cagcactttt gcgctctatc gctcaagtct ggggcgcaaa cgtccccgat   2100
agggagacaa tctaa                                                    2115
```

<210> SEQ ID NO 21
<211> LENGTH: 1863
<212> TYPE: DNA
<213> ORGANISM: Conynebacterium glutamicum

<400> SEQUENCE: 21

```
atgcgcgttt taattattga taattatgat tctttcacgt ttaatctcgc cacctatgtg     60
```

gaagaggtta cgggtcaggc acctgtggtg gtgcctaatg atcaagaaat agatgagacg 120
cttttcgacg ccgtcatcct ctcaccgggc ccgggccacg ccggcgttgc ggccgatttt 180
ggtatctctg caggcgtcat tgagcgtgca cgcgttccga ttttgggtgt gtgtttaggc 240
caccagggca ttgcgttggc tcatgacggt gatgttgatt tggcgcccag gccggtccac 300
ggtgaggttt cgcagatcac ccatgatggt tcaggtttat ttgcaggcat ccctgaaacg 360
tttgaggcgg tgcgttatca ctcgatggtg gcaacccgct tgccggagtc attgagagct 420
acagctacca gcgatgatgg tttgatcatg gcattggcac atgaaatgct tccgcagtgg 480
ggtgtgcaat ttcatccgga atctattggt ggacaattcg gccatcagat cattaagaac 540
ttccttaatt tagcgcgcac atatcgctgg caactcatgg agaaaactat tccgctcagc 600
gttgattcag cagcggtttt tgaaacattc tttgcccatt cctcccatgc tttttggctc 660
gatgatgccc aaggaaccag ctatcttggt gatgccagcg gtcctctcgc acgcacaaaa 720
acccataatg tcggcgaggg ggatttcttc acctggctaa aggaggatct cgccgccaac 780
tcagttgcgc ccggtcaagg ttttcgtctt ggctgggttg gttacgttgg ttatgagctt 840
aaagcggaag ctggcgcacg ggctgcacac acttcgagtc ttccggatgc gcacctcatt 900
tttgccgatc gcaccatcgc agtggaatcg gatcaggttc ggttgctggc gttgggggag 960
caagacgcat ggtttgaaga aaccacggag aagctgcata atcttgtcgc cccgcggata 1020
cctgcgtccg gacacctcgc tttgcaggtt cgagattcca aagatgggta tctcgacaaa 1080
attcgcagag cccaggagct gattactcgc ggcgaatcgt atgaaatctg cctgaccaca 1140
aaacttcagg gcaccactga tgcggcccct ctggctgcct atctagcact gcgtggggcc 1200
aatcccaccg catatggtgc gtatcttcag ctgggggata cctctatttt gagttcctcg 1260
ccggagcggt tcatcaccat tgattcggca gggcatgtgg aatcaaagcc cattaaaggc 1320
accaggccgc gtgggcgaac agcgcaagaa gaccaagaaa tcattgctga gctgcgcagt 1380
aatcctaaag atcgtgcaga aaacttgatg atcgtagatt tggtccgcaa cgacttagcc 1440
cgcggcgctt tgcccaccac agttaaaaca tccaagcttt tcgacgtcga aacctacgcc 1500
acagtccacc aacttgtcag caccgtctct gcagagttgg ggccacgcag tccgattgag 1560
tgcgtgcgcg cagcattccc cggtggttcg atgactggtg ccccaaagct gcgcaccatg 1620
gagatcatcg atgagctgga ggcagctcct cgcggtattt actcaggtgg cttgggatat 1680
ttttccctcg acggcgcagt tgatctctcc atggtgatca gaactctcgt catccagaac 1740
aatcacgtgg agtacggagt gggcggtgca cttcttgctc tgtctgatcc ggaggctgag 1800
tgggaggaaa tccgcgttaa atcacggcct ctgctgaatt tatttggggt tgaattccca 1860
tga 1863

<210> SEQ ID NO 22
<211> LENGTH: 1842
<212> TYPE: DNA
<213> ORGANISM: Conynebacterium ureicelerivorans

<400> SEQUENCE: 22
atgatcctgc tcgttgacaa ttacgattca tacacgttca acctcgccca ccttattgcg 60
gaggtgaccg ggcacgagcc cctcgtcgtg cccgccggcg acgcagcggg tctgccggaa 120
cgcgtccgcg ctggcgagtt cagccacgtt gtgatctccc ctggcccggg caccccagag 180
cgggacgagg acttcgtcgc ctcccggcgc gttatcgagg cggctgcaaa ggcgcaggtt 240
ccgttgctgg gcgtgtgcct cggccaccaa gggctagcca tgctcgccgg tgcggccgta 300

-continued

```
acccgggctc gcgagccgcg ccacgggttc gtctccacac tcacccactc cggcgagggg    360
atcttcaccg gcatcccgca aggcttcgag gtggtgcgct accactcgtt gcacgtcgag    420
gaggttcccg gcgtcacggt ccacgcgcgc agcgaggacg gcgtggtcca ggcgctgaaa    480
gtggacgggc ttccccactg ggtgtgcag ttccaccccg agtccgtgct cacgcagcac    540
ggcgcggcca tcatgcgtaa cttcctgggc ggctggcggc tgatccaccg ggaggtgccc    600
ggtggcatcg actgccagag ggtgttcgac gccatcaggc gcagcggcaa cgacgcgttt    660
ttcctggact ccgccgattc gcgcggcagc ttctccatcc tcggcgacac tgcgggcgcc    720
ctgtcccgct ccatcccctt cacgcttggc gacggcgaca ttctgcacga cctcgaacgg    780
gaactttcca cccccatcca cggagcgccc gatttgccgt tcaccggcgg ggtaatcggc    840
tacctcggct acgagtgcgc cgagctgacc atgccgatca cgttgcgcca ccgctccccc    900
tacccggacg cgtattttgt ccggccgcaa tccttcatcg tgtacgacca ccagaccgaa    960
accgcccacc tgtgcgccct ggccggcgag ggcgcagagg ggttgctcgg ccggctcgag   1020
caggcgcttc agggggcgga gggagccgga ggtgcgtcga taggtgaagg ctcctggagc   1080
aacccggact acctcggcag catcgagcag gcccaggagt tgctgcgcgc gggcgagagt   1140
tacgaggtgt gcttgaccga cactttcacc gccgaagcga cgggcgatat ctaccgccaa   1200
ctgcgcgaac acaaccccgc gccgtacgcc gcacacctca tcttcgaggg cgtggaggtc   1260
gccagcgcat cgcccgagcg cttcctcacc gtgcgcggcc gcgaggtgga ggcgaagccg   1320
atcaagggca ccatcgccgc tgatcaggac cccgcgctgc ttgacgacga caaaacccgc   1380
gccgaaaacc tcatgatcgt ggacctgctg cgaaacgacc tctcccgcgt ttgcgagccg   1440
ggtaccgtgc gcgtgccccg gctcatgcag gtggagtcgt acgcgagggt gcaccagttg   1500
gtttccacca tcaccgggca gctgcgcgag gggtgcaccg ccgtcgacgc tgtgcgcgcg   1560
acgttcccgc ccggctccat gaccggcgcg ccgaagctgc gcacctgcga gatcatcgac   1620
cgcttagaga cctccccgcg cggcgtctac tccggcgcgc tgggctactt cggcttcgac   1680
ggccaggctg atctctccgt ggtgatccgc accgccgtgc gcgcaggcaa caccgtcacc   1740
gtgggtgcgg gcggcgcgat cgtgctggcc tccgaccccg agtccgaact cgccgagcgc   1800
aacctcaagg cacagtccgt gctcggggcg tgggatgcgt ag                      1842
```

<210> SEQ ID NO 23
<211> LENGTH: 1692
<212> TYPE: DNA
<213> ORGANISM: Conynebacterium argentoratense

<400> SEQUENCE: 23

```
atgccgcgca ttgtgttgat cgacaaccag gattcttttt cgcatctttt agctgatgcg     60
atttttcgag ccgtcgggat tcttccgcag gtggttgccc atgacggcga attgcctgcg    120
aacgccgacg tgtttgtgct ctcccccggc cccggccgac cagaggacgc gcggttgagt    180
atcgaggccg tgcgcagcgg tgtgccgtgc gtgggggtgt gtttggggca tcaggtgatt    240
gctatggaag ccggtgcgac ggtagggccc gcgcagtttc ccatgcatgg ccgtgtcagc    300
caggtgtcgc attgcggcac aggaatgttc gcggggttgc cgcagtcgat ggaggttgtg    360
cgctatcact ccttggagat cacagatttt aatgacgccg cgttggaggt tctggcccgc    420
gcggacgacg gttcgatcat ggcctgccgc cggatggatg caccgcagtg ggtgtgcag    480
tttcacccgg agtccattgc gaccgtgcag ggcgtggacc ttgtgcgtaa tgccctgctg    540
```

-continued

```
tgtgcattag agccgtggaa gtgggcgcag cgctacccgt attttgcgtg gtttgaattc     600
gacggataca cccgcatcgc tgccgggaat gagcgctggg aggggccact ggacaccgat     660
gtcgccctgt atggcgccct atcgtatgag gccacaggcg gggtggatgg cagtagtgcc     720
gcgcagctgc ataccaggga caactccggt gccgatagtg cgcagagtat atggtttcac     780
cccgagcatg agctgcattg ggagggggcc gtaccggaag aacttttagg cgatgttccg     840
ccagcaccgc aggccagtgc tatttctttc cgtgacagcc gcgaagacta tcgcgaagct     900
atttcacgtt gtcgccaggc cattgcccgc ggtgattcct acgagttgtg cttgaccacc     960
gctgcgtcat caatcttgct tgaagatgtt tctgcgcttg agctgtatgt gcgcctacgc    1020
tcgctggtgc cggcacccat gcgcgggatg ttaacgagcc ccgaggtgtc aatcatttca    1080
gcatcaccgg agcgcttcgt ccgcgttcgc cccgggcagg cagcaactgg gggtgggcgc    1140
acgatctcgg cccatccgat caagggaaca cgtccagccg gttgcgaccc cgcggagctg    1200
ctatctagcg aaaaggatcg cgccgagaac ctgatgatcg tcgacctgat gcgcaacgat    1260
ctcgccccgcg tgtgcacccc gggaagcgtc acggtggagg aactttttgg tatttacgag    1320
ctcccccagg tcactcagat gatttcgact atttctggtc acgtgcgacc ggaagtctcc    1380
gccatcgacg ccgcgctcgc tgctttcccg ggcggctcga tgacgggcgc accaaagcag    1440
aaaactatgg atcttctgcg ggaatacgaa gggcaccctc gcggttatta ttccggggtg    1500
atgggctaca ttgactgtga cgacattgac ttgtccatgc tgattcgctg cgtcgtgcta    1560
cgtcagcggc gtctgcacta cggcgtgggc ggtgcaataa cgtggctgag cgacccagat    1620
gatgaatacg atgaggtcct tgtgaaggcc cggccgttgt ttgcgctgct gggccaacag    1680
tatgtgccgt ag                                                        1692
```

<210> SEQ ID NO 24
<211> LENGTH: 2112
<212> TYPE: DNA
<213> ORGANISM: Conynebacterium terpenotabidum

<400> SEQUENCE: 24

```
atgatcagga cactccttgt cgacaaccat gactccttca cctggaatct cgtccacgac      60
ctcatccggg tcaacggtgc cgagccggtc gtggtgccca atgactggga cgggtgggcg     120
gatgagggtg ctgagctgct cgaccgcgtc gacaacgtgg tcatctcgcc cggcccgggc     180
accccgctga accctgacga cgtcggtatc ggtccggcgg tcatcgctgc tgcggtggag     240
cgcaatgtcc ccgtcctcgg tatctgcctg ggacaccaac tcatcgccca cctctacggg     300
gcgaccgtcg gccgagccga cgagcccgtt cacggccggt cggcacaggt cgaccatgac     360
ggcaaggaga tcttccgcgg tctgccgtcc ccctttgagg ccgtccgcta tcactcgctg     420
gccgtcaccg gcgtccctga ggacgccggc atcaccgtga ccgcccacag cgaggacggc     480
accatcatgg ggctgacggt gcccggcaga ctgctgtggg gggtgcagtt ccacccggag     540
tcgatcaaca ccgggcacgg cgcggagatc ctcgcgaact tcgccgacct cacccgcgag     600
cacagtcggg tccggacggt ccgggacaag atcgtccccc tcacgggact ctccgaggca     660
gacacccgcg ccctgtccgc agccctgttc cgccgacact tcgccgacgc cacggacgct     720
gtctggctcg acgggaactc agtgggggac ccgcgcgccc gcttctccgt gatgggtgcc     780
gccgacgggc gcaacgccgg cccctccgcg gcggtcgcca ccgccgacgt ggacgccggg     840
accgtcaccc tcacccgtcg gggggagacg cagacgctgc acaccggcgt cctcgactgg     900
ctgcagcacg acctcgaccg gtggaacatc cgcggtggcg ggctggacgc cgacctggcc     960
```

```
ggccaacctc ccttctcctt ccagctcggt tgggtcggct acctcggcta cggcgtcaag   1020
gcccagtgct gtgacgggga gggcgggccg aacagtcaca ccccgcatga gccggacgcc   1080
gcattcgtct tcctcgaccg ggcggtcgtc atcgaccacc agaaggcgca ggcacatctg   1140
ctcaccctcg accgcccact cgcccgggac gtcggcccgt gggccaccgc cgacgagacg   1200
aaatgggcgg agcagaccgc cgcagtgctg cgtgacctgg tccgtcgccg cccgtgggag   1260
gaccagcgac ccgcagatat cccggtcgac ctcgagctcc acgaccgggc gtcctacacg   1320
gagaaggtcc ggcagatcca ggaactcatt cgcgccgggg agacctacga ggcctgtctg   1380
accaccacgg tgtccggcgt gccggccgtc gccggggcgt ccctcctcga gatctacgag   1440
agcctgcggg ccgccaaccc ggcaccgttc gcgtcctacc tgcaactgcc gggggtgacg   1500
gtgatgtcca cctcgccgga acgcttcctc cgggtggacg ctgccggtgc cgtcacctct   1560
tcgccgatca agggcacccg cccggtcggt gcgaccgagg aggaggacct gcgcatccgg   1620
gccgatctgc agagcagtga gaaggaccgg gcggagaacc tcatgatcgt cgacctggtc   1680
cgtcacgacc tcggtcgggt cgctgcacca ggcacggtcc aggtgccggc gctgttcacg   1740
gtggagagct atgcgacggt ccatcagttg gtcagtactg tcacggcccg gctcggcgac   1800
gggaacacgg gagtggacgc ggtccgcgct gccttcccgc ccggttcgat gaccggggcg   1860
ccgaaggaga ggacgatgcg cctgctggag gagctggagg acggtccgcg tggcgtgtac   1920
agcggggcgg tcgggtactt ctccctcgac ggcgcggtgg atttggcggt ggtgatccgc   1980
acactggtgt cctccgacgg gcagctgcgt tacggggtag gtggggcggt tgtcgcgcag   2040
tctgaccccg acggcgagta cgaggaaacg ttggtcaaga tgcgcgcggt ccggcagcgg   2100
gggagccgtt ag                                                       2112
```

<210> SEQ ID NO 25
<211> LENGTH: 2388
<212> TYPE: DNA
<213> ORGANISM: Neurospora crassa

<400> SEQUENCE: 25

```
atgggctcag taacaagaac cacgccattt gatgagcaac tctccatcct ctatgtcgac     60
tgtttcgact ctttcacaaa caacatcatc ggtcttctcg aggagcgtct aggcgcaaat    120
gtcatcatgg ttcgcatcga tgacaagcag gcggataggg atcttcacat gctgcttcgg    180
gccgtggatg gcgttgtcat cgggcccgga cccggtcatc ctggaaaccc ccaagatgtt    240
ggcttcattg acaagctctg ggctctcagt ggcacagaac tccttcccat ctttggcatc    300
tgcctcggct tccagtctct gtgcctcaac catggtgccg atgtcaagaa actcaagagc    360
ccccgccatg gcattgtcag ccgatccacg caccaaggta ccgatattct caaaggactc    420
ggtgatctcg attgtactca gtatcactcg cttcatgccg atctcgagct aacaggagct    480
cctccgaccc acttctggca accaaacaat gtatgccctg atctgttgcc tctcgcttgg    540
gatcttagcg atgagaataa cggcccagtg ttgatggctg tgcgccatgt ctccaagccg    600
ttctgggggt gtcagtttca tcccgaatcc atctgtacct cggaagctgg caaggacttg    660
ctcgtgaact ggtggaggca tgcccttcgg tggtcggcca acaacggtcg ggtcaagacc    720
atggagctca ctggtcgtta tcttcccaac tcgctttcca gcttctttgt ggacgcacct    780
attcagtctg gtcatctaca ggcatctcac ctcgctcaag aactgcgctc ggctgccggc    840
cgtgatgaca tcttcctccg ctgggccaaa tatccagctc agggtgtgac cccccactgtt    900
```

-continued

```
cttctggaga agctcggtca ccgagatgac gaggtcattc ttctggactc gcaaggacac    960
aacatgggtc gcttcgatat tcttggactc gtcgttcccg gtaagaccgc gaacgtcacc   1020
tacagctctt atgaccgcac gctcagatat ggcaatcact ccaagaacat cgattcgatc   1080
gaagaatgct ggcctctctt tcaggaggct ctcgatatct actacccccca gaaccaggaa   1140
atcgaccggt ccaagctgcg ctcggatatg gacagattca ttgccggcca cctgcccgcc   1200
gacagcccct tttggggcgg gtttatgggg tatatttcgt acgaggccgg acttgagacc   1260
atcgacgtca ggcttcccga aaagccaacc gacggctcag ctatccccga catcaacttt   1320
gcctttatcc accgtagcat cgttatcgat caccacacca accagatcta cgtccaatcc   1380
cttctgccca atgattggac ctggattctc cgcgtcggta gccttatcga ctccgtttct   1440
gctgcctcca gcaaatctga ctgcccgtca ctcacttcca ttgcggagtc tcgtcacctc   1500
aacgacacac tcgcccgctc caccatcacc cgcccgaccg gcgattccta ccgcgcgcaa   1560
gtccaaaatt gccaagacca tctccgagcc ggcgactcct acgagctctg cctcacagac   1620
gagagctcca tcgtcatccc ctcggaccca tcttctaact cacactcacc cctcgacgcc   1680
tggtccctct acaagaagat gcgccttaat aacccagccc cgcacggcgc ctacctcaac   1740
ctgcccaaca tatccattgt cggtaccagc ccggagcgct ttctctcctg gtcgcgcggc   1800
ggccactgcc agttccgacc catcaagggc actgtaaaaa agggccctgg gatgacccac   1860
tccatcgcca gcgaaatcct caacagcagc aaagaacggg ccgaaaacct gatgatcgtc   1920
gacctcatcc gccacgacct gtccggtgtc gtcggcgccg acaacacctg ggtgtccaag   1980
ctgatggtca tggaggagta cgagaaggtg taccagctcg tgagcgtcat cgagggccaa   2040
ctgcctccct cggaactacc cggcgctccc aggggactgc atgtcctcaa gaactcgttg   2100
cctccgggat cgatgacggg ggcgccaaag aaaaggtcgt gcgagatctt ggttgatctg   2160
gagaaacggc cgaggggtgt ctatgcgggt gtgctgggat atatggatgt tggtggcgca   2220
ggagactttg cggtggtcat tagaacgctg gtaaggaata agttggagga acaagaggtg   2280
tggcggattg gggcgggtgg ggcggttact attcagagta cggatgaagg ggagtttgag   2340
gagatggaga ttaaggcagg gagcgtgctg gagtcgatga tgaagtga                2388
```

<210> SEQ ID NO 26
<211> LENGTH: 2073
<212> TYPE: DNA
<213> ORGANISM: Rodococcus opacus

<400> SEQUENCE: 26

```
atgagtaccc ggacgctgtt ggtcgacaac tacgattcgt tcacctacaa cctgttcacc     60
ctgctggccg aggtgaacgg tgaacccccc acggtcgtgc acaacgacgt ggagtgggat    120
tcgatcccct ggtccgactt cgacaacatc gtcatctccc ccggccccgg acgcccggag    180
cggcgacgag acttcgggat cagtgcgcgc atcatcacgg agaccgaact acccgtcctc    240
ggcgtgtgcc tcggtcatca gggactgtgc cagctgttcg ggggcagcgt agttctcgca    300
cccgaaccga tgcacggccg cgtgtcgctc gtcgaacatg acggttccga actcttcgcc    360
ggcattccgt caccgttccc gacggtccgc taccactcgc tgatcgtcga ggatctcccc    420
gacgacctcg aggccaccgc ctggaccgcc gacggcctgc tgatgggtgt ccgccaccgg    480
actcgtccgc tgtggggcgt ccagttccac cccgaatcga tcagcaccgc cttcggtcac    540
gaactgctcg cgaacttccg cgatctcacg cagacgcatt ccgggacacc cacgcacggg    600
tccatgctga gaatcccgat tccccacgcg ccgtacgtgg tccagcaggt gcgcgtcgat    660
```

```
cacgaagtcg atccccgcac cacgttcgag gatctcttcg cgtccgggcc caacgcgttc    720
tggctggacg ggacgtcggc ctcggaaccg acttcgcgat tcaccatcat gggcaattgt    780
tccggcccgc gcgccgagta catcacgtac gacgtcagcg aagcgatcgt ccggatcacc    840
cgcgaggggt tgccggtcga acaggtgcac gcaccgttct tcgactacct cgagcggcaa    900
ctgcaggccc ggtcggtgcc cggtctcccg ggtgtgccgt tcggcctcgg ctacgtgggg    960
tacctcggct acgaactgaa ggccgagacc ggcggcacgg cggcccacaa gtcgcccacc   1020
cccgatgccg cgctggtgtt cgccgaccgc gccgtcgtca tcgaccattc gggcgagcgg   1080
acctacgcgc tgtgcctgag tgatcatcag gacgatccgg agttgcgccg ctggctcgac   1140
gagatggagg tggcactgca tcggctggcc gagccggaca acccgccgac cgcggtgtcg   1200
ccgatccgga agccggagtc cgccgaactc gccctgcgcc acgagcacga caagtacctc   1260
gaacacatcg cgacctcgct cggtgagatc cggaccggtg agtcctacga ggtgtgcctg   1320
accaacatgg cgacagtgga ccagtcgatc gatcccctgc acacgttcga gttgctgcgc   1380
tccatcagcc ccaccccgta cagcgcgtac ctccagttcg ccggactgtc ggttctcagc   1440
gcctcccccg aacggttcct gaggatcggc gcggaccggg tggtggagtc caaacccatc   1500
aaggggacgc ggccgcgcgg cgcgaccccc gccaaggacg cggcgcttcg gcaggacctg   1560
ctcgacagcg agaaggaccg cgccgagaac ctgatgatcg tcgatctgac gcgcaacgat   1620
ctggctcggg tgtgcgttcc cggatctgtg cacgttccca agctcttcga cgtcgagacg   1680
tacgcggccg tgcatcaact cgtgtcgacc gtgcgcggga ccctcagcgc ggatgcctcc   1740
gtcgtcgagt gtgttcgcgc cgccttcccg ggcggatcga tgacgggcgc cccgaaaatc   1800
cggaccatgg agatcatcga ccggctcgag tccgggccgc gcggtgtgta ttccggttcg   1860
atcggctact tctcactgac ggggacggcc gacctgtcga tcgtcatccg gacgatagtc   1920
gccacggaca ccgaggtgac gttcggtatc ggtggggcga tcacggcact ctccgacccg   1980
gaggaggagt tcgacgaggc gatggtcaag gccgccacca tgttgcgggc actaaccgtg   2040
acggcagacc ggccgaacga gatcgggcag tga                                 2073
```

<210> SEQ ID NO 27
<211> LENGTH: 2085
<212> TYPE: DNA
<213> ORGANISM: Rodococcus erythropolis

<400> SEQUENCE: 27

```
atgagttccc gcacccttct ggtggacaat tacgactcgt tcacctacaa cctgttcacc     60
ctgttgaccg aggtcaacgg ggttgttccc accgtggtcc gcaacgacgc ggattgggat    120
tccctcgatc tggcgtcgta cgacaacgtg gtcatctccc ccggtcccgg ccggccggat    180
cgcgaccgtg atttcggaat cagccgccgt ttcatcgagg aagcgcctct cccacttctc    240
ggtgtctgtc tcggccacca gggcctgtgc gagttgttcg gcgcggatgt cgtggttgcg    300
cccgtaccga tgcacggccg gatttcgctg atcgatcacg acggttcggg catctttgcc    360
ggacttccgt cgccgttccg agcagttcgc taccactcgt tgaccgtcga gaatctgccg    420
aatgccttcg ttcgtaccgc gtggacgtcc gacggtctgc tcatgggtgt ccggcaccgg    480
accaagccga tgtggggcgt gcagttccat ccggagtcga tcagtacgga gttcggcatc    540
gatttgctcg agaacttccg tgatctgtct gtcggacgaa ctctggattc ggtgatccga    600
cccgaaccgg ctccgcaaac acccgacctg cgaccggcga tcaactacga cgtcgacgac    660
```

-continued gtgactctcg attttgcggt ggatccgtcg gcggcctttg cagcactctt cgcagacggc 720
ccgaacgcgt tctggctaga ccgcgcggca actgcagaac cgagtgcacg cttttcgatt 780
ctcggcgatt cgtcggggcc gctggccgag ttcatcacgt acgacgtgca ggccgaggta 840
ctcactgtca gccgaaaagg cctgtccgac gagaacattc gagttccgtt cttcgattac 900
ctggacgggc aactcgcgac acgcttcgtt ccctcgcatc cggaactcga tttcaacctc 960
ggatacgtgg gctacctcgg ctacgaactg aaggcgcaga ccggaggaag ggcagtccat 1020
ccggcaccca ctcctgatgc cgccctggtg tttgccgatc gcgccgtcgt catcgatcac 1080
accgccggcc gcactcacgt tttgaggttg cgcgagaaag tccgcgacgc cggccacgac 1140
gattggctcg aatcgaccgt cgacgccctg gcgcgactcg gcgcggacct tccggaacgc 1200
acccccgttc cattgatcag cgacaccgtc tggacgcagg ctcgcctgcg gcatgatcgc 1260
gatcagtacc tgtcgttgat cggaacggcc ctctcggaga tccgggcagg tgagtcctac 1320
gaggtatgtc tgaccaacat ggcgagcgtc gacgagacga tcgacgcacg gcgggcgttc 1380
gagtatctac gctcgatcaa tccgacgccg tacagcgcac tgctcgactt caccggcatc 1440
tcggtggtct cggcctcgcc tgagcggttc cttcgcgtcg actcggacgg caacgtcgag 1500
tccaagccga tcaaagggac ccgcccgcgc ggcgtcacgc gagcgcgtga tgctgccctg 1560
aggcaggacc tgctcgacag cgagaaggac cgcgccgaga acctgatgat cgtggacctc 1620
actcgcaacg acctcaccaa ggtctgcgtt ccgggaagtg tccacgttcc gaggctgttc 1680
gcgatcgagt cgtactcgtc cgttcaccaa atggtgtcga ctgtgcgtgg acatctgagt 1740
ccaggatcgt cggcggtgga ctgtgtccgt gccgcgttcc ccggtggatc gatgacaggc 1800
gccccgaagg tacggacgat ggagatcatc gaccgcctcg aatccggccc acgtggggtc 1860
tactcgggat cgatcgggta cttcgccctc ggtggcgccg cggacctctc gatcgtaatt 1920
cggtcgctcg tctgcaccga gagcggcgtg accttcggaa tcggcggtgc catcacagcg 1980
ttgtccgatc cggaagaaga attcgacgag accacggtca aggcgtccac gctgctccgt 2040
gcgctcgacg cggtgtcctc gcgggtcctc gagtacggcg ggtag 2085

<210> SEQ ID NO 28
<211> LENGTH: 35
<212> TYPE: DNA
<213> ORGANISM: Artificial sequence
<220> FEATURE:
<223> OTHER INFORMATION: PCR primer

<400> SEQUENCE: 28
ctctcatatg ttcttaatta acggtcataa gcagg 35

<210> SEQ ID NO 29
<211> LENGTH: 30
<212> TYPE: DNA
<213> ORGANISM: Artificial sequence
<220> FEATURE:
<223> OTHER INFORMATION: PCR primer

<400> SEQUENCE: 29
ctctcatatg catgactaat tcgggcgctc 30

<210> SEQ ID NO 30
<211> LENGTH: 41
<212> TYPE: DNA
<213> ORGANISM: Artificial sequence
<220> FEATURE:
<223> OTHER INFORMATION: PCR primer

<400> SEQUENCE: 30
ctctcatatg ttcttaataa atggtcaaaa acaaacatgg c 41

<210> SEQ ID NO 31
<211> LENGTH: 33
<212> TYPE: DNA
<213> ORGANISM: Artificial sequence
<220> FEATURE:
<223> OTHER INFORMATION: PCR primer

<400> SEQUENCE: 31
ctctcatatg tcataatgaa ttcgggtgct cac 33

<210> SEQ ID NO 32
<211> LENGTH: 27
<212> TYPE: DNA
<213> ORGANISM: Artificial sequence
<220> FEATURE:
<223> OTHER INFORMATION: PCR primer

<400> SEQUENCE: 32
ctctcatatg ctcgaacctg ttgtctc 27

<210> SEQ ID NO 33
<211> LENGTH: 37
<212> TYPE: DNA
<213> ORGANISM: Artificial sequence
<220> FEATURE:
<223> OTHER INFORMATION: PCR primer

<400> SEQUENCE: 33
ctctcatatg ctacaaaagc caagaataaa gagagag 37

<210> SEQ ID NO 34
<211> LENGTH: 32
<212> TYPE: DNA
<213> ORGANISM: Artificial sequence
<220> FEATURE:
<223> OTHER INFORMATION: PCR primer

<400> SEQUENCE: 34
ctctctcata tgacacaagt gtgggttaat gg 32

<210> SEQ ID NO 35
<211> LENGTH: 38
<212> TYPE: DNA
<213> ORGANISM: Artificial sequence
<220> FEATURE:
<223> OTHER INFORMATION: PCR primer

<400> SEQUENCE: 35
ctctctcata tgtcataggg taagttgcag agtatttc 38

<210> SEQ ID NO 36
<211> LENGTH: 30
<212> TYPE: DNA
<213> ORGANISM: Artificial sequence
<220> FEATURE:
<223> OTHER INFORMATION: PCR primer

<400> SEQUENCE: 36
ctctctcata tgacttctcc ggcttccgtg 30

<210> SEQ ID NO 37

-continued

<211> LENGTH: 33
<212> TYPE: DNA
<213> ORGANISM: Artificial sequence
<220> FEATURE:
<223> OTHER INFORMATION: PCR primer

<400> SEQUENCE: 37
ctctctcata tgttactgta tgcccgccaa cag 33

<210> SEQ ID NO 38
<211> LENGTH: 31
<212> TYPE: DNA
<213> ORGANISM: Artificial sequence
<220> FEATURE:
<223> OTHER INFORMATION: PCR primer

<400> SEQUENCE: 38
ctctctcata tgttctggta caacggtaag c 31

<210> SEQ ID NO 39
<211> LENGTH: 37
<212> TYPE: DNA
<213> ORGANISM: Artificial sequence
<220> FEATURE:
<223> OTHER INFORMATION: PCR primer

<400> SEQUENCE: 39
ctctctcata tggtcatgct aagaatagtt ccctaag 37

<210> SEQ ID NO 40
<211> LENGTH: 24
<212> TYPE: DNA
<213> ORGANISM: Artificial sequence
<220> FEATURE:
<223> OTHER INFORMATION: PCR primer

<400> SEQUENCE: 40
ctctccatgg cctgctggat cgac 24

<210> SEQ ID NO 41
<211> LENGTH: 30
<212> TYPE: DNA
<213> ORGANISM: Artificial sequence
<220> FEATURE:
<223> OTHER INFORMATION: PCR primer

<400> SEQUENCE: 41
ctctccatgg tcaggagtcc agtagcttgc 30

<210> SEQ ID NO 42
<211> LENGTH: 27
<212> TYPE: DNA
<213> ORGANISM: Artificial sequence
<220> FEATURE:
<223> OTHER INFORMATION: PCR primer

<400> SEQUENCE: 42
ctctccatgg agccggatta tcagctg 27

<210> SEQ ID NO 43
<211> LENGTH: 30
<212> TYPE: DNA
<213> ORGANISM: Artificial sequence
<220> FEATURE:
<223> OTHER INFORMATION: PCR primer

<400> SEQUENCE: 43
ctctccatgg ttaagcctcg atcagctgtg 30

<210> SEQ ID NO 44
<211> LENGTH: 43
<212> TYPE: DNA
<213> ORGANISM: Artificial sequence
<220> FEATURE:
<223> OTHER INFORMATION: PCR primer

<400> SEQUENCE: 44
ctcttcatga gaaggatagt tcataattat gataaagtaa tgc 43

<210> SEQ ID NO 45
<211> LENGTH: 34
<212> TYPE: DNA
<213> ORGANISM: Artificial sequence
<220> FEATURE:
<223> OTHER INFORMATION: PCR primer

<400> SEQUENCE: 45
ctcttcatga gtaaggattt tagtcgcgat tgtg 34

<210> SEQ ID NO 46
<211> LENGTH: 32
<212> TYPE: DNA
<213> ORGANISM: Artificial sequence
<220> FEATURE:
<223> OTHER INFORMATION: PCR primer

<400> SEQUENCE: 46
ctctctcata tgtctgaggt tatcacgcct tc 32

<210> SEQ ID NO 47
<211> LENGTH: 33
<212> TYPE: DNA
<213> ORGANISM: Artificial sequence
<220> FEATURE:
<223> OTHER INFORMATION: PCR primer

<400> SEQUENCE: 47
ctctctcata tgctacagcc ttaaacatcc agg 33

<210> SEQ ID NO 48
<211> LENGTH: 33
<212> TYPE: DNA
<213> ORGANISM: Artificial sequence
<220> FEATURE:
<223> OTHER INFORMATION: PCR primer

<400> SEQUENCE: 48
ctcttcatga tgatgtatgt agatggtgaa ctc 33

<210> SEQ ID NO 49
<211> LENGTH: 32
<212> TYPE: DNA
<213> ORGANISM: Artificial sequence
<220> FEATURE:
<223> OTHER INFORMATION: PCR primer

<400> SEQUENCE: 49
ctcttcatga ccttataact cactcttgct cc 32

<210> SEQ ID NO 50
<211> LENGTH: 25
<212> TYPE: DNA

<213> ORGANISM: Artificial sequence
<220> FEATURE:
<223> OTHER INFORMATION: PCR primer

<400> SEQUENCE: 50
ctcttcatga cgagacctga cgctg 25

<210> SEQ ID NO 51
<211> LENGTH: 29
<212> TYPE: DNA
<213> ORGANISM: Artificial sequence
<220> FEATURE:
<223> OTHER INFORMATION: PCR primer

<400> SEQUENCE: 51
ctcttcatga accagctagg cgtccagac 29

<210> SEQ ID NO 52
<211> LENGTH: 30
<212> TYPE: DNA
<213> ORGANISM: Artificial sequence
<220> FEATURE:
<223> OTHER INFORMATION: PCR primer

<400> SEQUENCE: 52
ctctctcata tggtcatggg ctattggtac 30

<210> SEQ ID NO 53
<211> LENGTH: 32
<212> TYPE: DNA
<213> ORGANISM: Artificial sequence
<220> FEATURE:
<223> OTHER INFORMATION: PCR primer

<400> SEQUENCE: 53
ctctctcata tgggattaca cgaccagttg ac 32

<210> SEQ ID NO 54
<211> LENGTH: 36
<212> TYPE: DNA
<213> ORGANISM: Artificial sequence
<220> FEATURE:
<223> OTHER INFORMATION: PCR primer

<400> SEQUENCE: 54
ctctctcata tgtgccaatt tattgaaacg attcgc 36

<210> SEQ ID NO 55
<211> LENGTH: 32
<212> TYPE: DNA
<213> ORGANISM: Artificial sequence
<220> FEATURE:
<223> OTHER INFORMATION: PCR primer

<400> SEQUENCE: 55
ctctctcata tggaggcttt gttcaacggt tc 32

<210> SEQ ID NO 56
<211> LENGTH: 25
<212> TYPE: DNA
<213> ORGANISM: Artificial sequence
<220> FEATURE:
<223> OTHER INFORMATION: PCR primer

<400> SEQUENCE: 56
ctcttcatga cacgctggct cgacg 25

<210> SEQ ID NO 57
<211> LENGTH: 34
<212> TYPE: DNA
<213> ORGANISM: Artificial sequence
<220> FEATURE:
<223> OTHER INFORMATION: PCR primer

<400> SEQUENCE: 57
ctcttcatga ctttaacgcc ataattgatg gctc 34

<210> SEQ ID NO 58
<211> LENGTH: 36
<212> TYPE: DNA
<213> ORGANISM: Artificial sequence
<220> FEATURE:
<223> OTHER INFORMATION: PCR primer

<400> SEQUENCE: 58
ctctcatatg attctgctga ttgataacta cgattc 36

<210> SEQ ID NO 59
<211> LENGTH: 34
<212> TYPE: DNA
<213> ORGANISM: Artificial sequence
<220> FEATURE:
<223> OTHER INFORMATION: PCR primer

<400> SEQUENCE: 59
ctctcatatg tcagcgattg aggaaattag ccag 34

<210> SEQ ID NO 60
<211> LENGTH: 45
<212> TYPE: DNA
<213> ORGANISM: Artificial sequence
<220> FEATURE:
<223> OTHER INFORMATION: PCR primr

<400> SEQUENCE: 60
ctctcatatg cgcgttttaa ttgttgataa ttatgattca tttac 45

<210> SEQ ID NO 61
<211> LENGTH: 30
<212> TYPE: DNA
<213> ORGANISM: Artificial sequence
<220> FEATURE:
<223> OTHER INFORMATION: PCR primer

<400> SEQUENCE: 61
ctctcatatg ccacagcaaa gtactcatgg 30

<210> SEQ ID NO 62
<211> LENGTH: 28
<212> TYPE: DNA
<213> ORGANISM: Artificial sequence
<220> FEATURE:
<223> OTHER INFORMATION: PCR primer

<400> SEQUENCE: 62
ctctcatatg cgcgtactga tcatcgac 28

<210> SEQ ID NO 63
<211> LENGTH: 29
<212> TYPE: DNA
<213> ORGANISM: Artificial sequence
<220> FEATURE:

-continued

<223> OTHER INFORMATION: PCR primer

<400> SEQUENCE: 63
ctctcatatg aggtgcctca cgggaactc 29

<210> SEQ ID NO 64
<211> LENGTH: 42
<212> TYPE: DNA
<213> ORGANISM: Artificial sequence
<220> FEATURE:
<223> OTHER INFORMATION: PCR primer

<400> SEQUENCE: 64
ctctcatatg attcttctac ttgataatca tgactcttat ac 42

<210> SEQ ID NO 65
<211> LENGTH: 30
<212> TYPE: DNA
<213> ORGANISM: Artificial sequence
<220> FEATURE:
<223> OTHER INFORMATION: PCR primer

<400> SEQUENCE: 65
ctctcatatg tggggccatt agattgtctc 30

<210> SEQ ID NO 66
<211> LENGTH: 42
<212> TYPE: DNA
<213> ORGANISM: Artificial sequence
<220> FEATURE:
<223> OTHER INFORMATION: PCR primer

<400> SEQUENCE: 66
ctctgcatgc gcgttttaat tattgataat tatgattctt tc 42

<210> SEQ ID NO 67
<211> LENGTH: 38
<212> TYPE: DNA
<213> ORGANISM: Artificial sequence
<220> FEATURE:
<223> OTHER INFORMATION: PCR primer

<400> SEQUENCE: 67
ctctgcatgc tcatgggaat tcaaccccaa ataaattc 38

<210> SEQ ID NO 68
<211> LENGTH: 33
<212> TYPE: DNA
<213> ORGANISM: Artificial sequence
<220> FEATURE:
<223> OTHER INFORMATION: PCR primer

<400> SEQUENCE: 68
ctctctcata tgatcctgct cgttgacaat tac 33

<210> SEQ ID NO 69
<211> LENGTH: 31
<212> TYPE: DNA
<213> ORGANISM: Artificial sequence
<220> FEATURE:
<223> OTHER INFORMATION: PCR primer

<400> SEQUENCE: 69
ctctctcata tgcagacgta cctacgcatc c 31

<210> SEQ ID NO 70
<211> LENGTH: 28
<212> TYPE: DNA
<213> ORGANISM: Artificial sequence
<220> FEATURE:
<223> OTHER INFORMATION: PCR primer

<400> SEQUENCE: 70
ctctcatatg ccgcgcattg tgttgatc 28

<210> SEQ ID NO 71
<211> LENGTH: 29
<212> TYPE: DNA
<213> ORGANISM: Artificial sequence
<220> FEATURE:
<223> OTHER INFORMATION: PCR primer

<400> SEQUENCE: 71
ctctcatatg ctacggcaca tactgttgg 29

<210> SEQ ID NO 72
<211> LENGTH: 28
<212> TYPE: DNA
<213> ORGANISM: Artificial sequence
<220> FEATURE:
<223> OTHER INFORMATION: PCR primer

<400> SEQUENCE: 72
ctctcatatg atcaggacac tccttgtc 28

<210> SEQ ID NO 73
<211> LENGTH: 30
<212> TYPE: DNA
<213> ORGANISM: Artificial sequence
<220> FEATURE:
<223> OTHER INFORMATION: PCR primer

<400> SEQUENCE: 73
ctctcatatg gaaagtgtca gtcacacctc 30

<210> SEQ ID NO 74
<211> LENGTH: 28
<212> TYPE: DNA
<213> ORGANISM: Artificial sequence
<220> FEATURE:
<223> OTHER INFORMATION: PCR primer

<400> SEQUENCE: 74
ctctcatatg ggctcagtaa caagaacc 28

<210> SEQ ID NO 75
<211> LENGTH: 31
<212> TYPE: DNA
<213> ORGANISM: Artificial sequence
<220> FEATURE:
<223> OTHER INFORMATION: PCR rimer

<400> SEQUENCE: 75
ctctcatatg tcacttcatc atcgactcca g 31

<210> SEQ ID NO 76
<211> LENGTH: 25
<212> TYPE: DNA
<213> ORGANISM: Artificial sequence
<220> FEATURE:
<223> OTHER INFORMATION: PCR primer -continued

<400> SEQUENCE: 76
ctctcatatg agtacccgga cgctg 25

<210> SEQ ID NO 77
<211> LENGTH: 29
<212> TYPE: DNA
<213> ORGANISM: Artificial sequence
<220> FEATURE:
<223> OTHER INFORMATION: PCR primer

<400> SEQUENCE: 77
ctctcatatg acgttcactg cccgatctc 29

<210> SEQ ID NO 78
<211> LENGTH: 26
<212> TYPE: DNA
<213> ORGANISM: Artificial sequence
<220> FEATURE:
<223> OTHER INFORMATION: PCR primer

<400> SEQUENCE: 78
ctctcatatg agttcccgca cccttc 26

<210> SEQ ID NO 79
<211> LENGTH: 29
<212> TYPE: DNA
<213> ORGANISM: Artificial sequence
<220> FEATURE:
<223> OTHER INFORMATION: PCR primer

<400> SEQUENCE: 79
ctctcatatg cgtcatggct ggatctacc 29

<210> SEQ ID NO 80
<211> LENGTH: 29
<212> TYPE: DNA
<213> ORGANISM: Artificial sequence
<220> FEATURE:
<223> OTHER INFORMATION: PCR primer

<400> SEQUENCE: 80
ctctgtcgac acgagttctc gcagcacat 29

<210> SEQ ID NO 81
<211> LENGTH: 30
<212> TYPE: DNA
<213> ORGANISM: Artificial sequence
<220> FEATURE:
<223> OTHER INFORMATION: PCR primer

<400> SEQUENCE: 81
ctctgtcgac ataaatcctg gtcagcggtg 30

<210> SEQ ID NO 82
<211> LENGTH: 33
<212> TYPE: DNA
<213> ORGANISM: Artificial sequence
<220> FEATURE:
<223> OTHER INFORMATION: PCR primer

<400> SEQUENCE: 82
ctctcctgca ggctgaccag gatttatctg tcc 33

<210> SEQ ID NO 83
<211> LENGTH: 31

<212> TYPE: DNA
<213> ORGANISM: Artificial sequence
<220> FEATURE:
<223> OTHER INFORMATION: PCR primer

<400> SEQUENCE: 83
ctctcctgca gggatcgtca ccttccaaac c 31

<210> SEQ ID NO 84
<211> LENGTH: 29
<212> TYPE: DNA
<213> ORGANISM: Artificial sequence
<220> FEATURE:
<223> OTHER INFORMATION: PCR primer

<400> SEQUENCE: 84
ctctagatct tctaggccag gaactaacg 29

<210> SEQ ID NO 85
<211> LENGTH: 27
<212> TYPE: DNA
<213> ORGANISM: Artificial sequence
<220> FEATURE:
<223> OTHER INFORMATION: PCR primer

<400> SEQUENCE: 85
ctctagatct gaagggtgct tcgcttc 27

<210> SEQ ID NO 86
<211> LENGTH: 34
<212> TYPE: DNA
<213> ORGANISM: Artificial sequence
<220> FEATURE:
<223> OTHER INFORMATION: PCR primer

<400> SEQUENCE: 86
ctctcctgca gggtggatac aaatgggatg tctg 34

<210> SEQ ID NO 87
<211> LENGTH: 32
<212> TYPE: DNA
<213> ORGANISM: Artificial sequence
<220> FEATURE:
<223> OTHER INFORMATION: PCR primer

<400> SEQUENCE: 87
ctctcctgca gggatgaagt tgctgaagca gg 32

<210> SEQ ID NO 88
<211> LENGTH: 28
<212> TYPE: DNA
<213> ORGANISM: Artificial sequence
<220> FEATURE:
<223> OTHER INFORMATION: PCR primer

<400> SEQUENCE: 88
ctctgtcgac cagatggcag ttgaggtg 28

<210> SEQ ID NO 89
<211> LENGTH: 30
<212> TYPE: DNA
<213> ORGANISM: Artificial sequence
<220> FEATURE:
<223> OTHER INFORMATION: PCR primer

<400> SEQUENCE: 89
ctctgtcgac cgatcagtgg agatcaacac 30

<210> SEQ ID NO 90
<211> LENGTH: 33
<212> TYPE: DNA
<213> ORGANISM: Artificial sequence
<220> FEATURE:
<223> OTHER INFORMATION: PCR primer

<400> SEQUENCE: 90
ctctgtcgac ctgtggtgac tttattgtct agg 33

<210> SEQ ID NO 91
<211> LENGTH: 31
<212> TYPE: DNA
<213> ORGANISM: Artificial sequence
<220> FEATURE:
<223> OTHER INFORMATION: PCR primer

<400> SEQUENCE: 91
ctctgtcgac gccagcttct gtaagtaact c 31

<210> SEQ ID NO 92
<211> LENGTH: 41
<212> TYPE: DNA
<213> ORGANISM: Artificial sequence
<220> FEATURE:
<223> OTHER INFORMATION: PCR primer

<400> SEQUENCE: 92
ctctagatct gtgctgatct taatattgaa tcgttttatt c 41

<210> SEQ ID NO 93
<211> LENGTH: 30
<212> TYPE: DNA
<213> ORGANISM: Artificial sequence
<220> FEATURE:
<223> OTHER INFORMATION: PCR primer

<400> SEQUENCE: 93
ctctagatct gactactgtg agtggcttga 30

<210> SEQ ID NO 94
<211> LENGTH: 32
<212> TYPE: DNA
<213> ORGANISM: Artificial sequence
<220> FEATURE:
<223> OTHER INFORMATION: PCR primer

<400> SEQUENCE: 94
ctctcctgca ggacaaagtg cttagaggtg cg 32

<210> SEQ ID NO 95
<211> LENGTH: 32
<212> TYPE: DNA
<213> ORGANISM: Artificial sequence
<220> FEATURE:
<223> OTHER INFORMATION: PCR primer

<400> SEQUENCE: 95
ctctcctgca gggaagcagg agaaattcgt cc 32

<210> SEQ ID NO 96
<211> LENGTH: 30
<212> TYPE: DNA
<213> ORGANISM: Artificial sequence
<220> FEATURE:
<223> OTHER INFORMATION: PCR primer

<400> SEQUENCE: 96
ctctgagctc tgattgcacg atggcgaaaa 30

<210> SEQ ID NO 97
<211> LENGTH: 30
<212> TYPE: DNA
<213> ORGANISM: Artificial sequence
<220> FEATURE:
<223> OTHER INFORMATION: PCR primer

<400> SEQUENCE: 97
ctctgtcgac ctgcaacaag tgaaaaaaga 30

<210> SEQ ID NO 98
<211> LENGTH: 30
<212> TYPE: DNA
<213> ORGANISM: Artificial sequence
<220> FEATURE:
<223> OTHER INFORMATION: PCR primer

<400> SEQUENCE: 98
ctcttctaga gctgccgtag ctttttggga 30

<210> SEQ ID NO 99
<211> LENGTH: 30
<212> TYPE: DNA
<213> ORGANISM: Artificial sequence
<220> FEATURE:
<223> OTHER INFORMATION: PCR primer

<400> SEQUENCE: 99
ctctctcgag tactcacctt ttcgatccgc 30

<210> SEQ ID NO 100
<211> LENGTH: 30
<212> TYPE: DNA
<213> ORGANISM: Artificial sequence
<220> FEATURE:
<223> OTHER INFORMATION: PCR primer

<400> SEQUENCE: 100
ctctgagctc gtgaacatat cggcatcgag 30

<210> SEQ ID NO 101
<211> LENGTH: 30
<212> TYPE: DNA
<213> ORGANISM: Artificial sequence
<220> FEATURE:
<223> OTHER INFORMATION: PCR primer

<400> SEQUENCE: 101
ctctgtcgac ctatggcgtt ctatactgcg 30

<210> SEQ ID NO 102
<211> LENGTH: 30
<212> TYPE: DNA
<213> ORGANISM: Artificial sequence
<220> FEATURE:
<223> OTHER INFORMATION: PCR primer

<400> SEQUENCE: 102
ctcttctaga tatgcaagaa gcaagcaagt 30

-continued

<210> SEQ ID NO 103
<211> LENGTH: 30
<212> TYPE: DNA
<213> ORGANISM: Artificial sequence
<220> FEATURE:
<223> OTHER INFORMATION: PCR primer

<400> SEQUENCE: 103
ctctctcgag tctcataaaa gttctccgat 30

<210> SEQ ID NO 104
<211> LENGTH: 30
<212> TYPE: DNA
<213> ORGANISM: Artificial sequence
<220> FEATURE:
<223> OTHER INFORMATION: PCR primer

<400> SEQUENCE: 104
ctctcctgca ggtccagtgt ggatcgcaac 30

<210> SEQ ID NO 105
<211> LENGTH: 33
<212> TYPE: DNA
<213> ORGANISM: Artificial sequence
<220> FEATURE:
<223> OTHER INFORMATION: PCR prpimer

<400> SEQUENCE: 105
ctctcctgca gggaggatat ggtgactagc ttg 33

<210> SEQ ID NO 106
<211> LENGTH: 30
<212> TYPE: DNA
<213> ORGANISM: Artificial sequence
<220> FEATURE:
<223> OTHER INFORMATION: PCR primer

<400> SEQUENCE: 106
ctctgatatc cttcctaaac gatgagcgag 30

<210> SEQ ID NO 107
<211> LENGTH: 30
<212> TYPE: DNA
<213> ORGANISM: Artificial sequence
<220> FEATURE:
<223> OTHER INFORMATION: PCR primer

<400> SEQUENCE: 107
ctctgatatc ttggtcagtt cagtctggag 30

<210> SEQ ID NO 108
<211> LENGTH: 31
<212> TYPE: DNA
<213> ORGANISM: Artificial sequence
<220> FEATURE:
<223> OTHER INFORMATION: PCR primer

<400> SEQUENCE: 108
ctctcctgca ggcaccgttg tcagcttcac t 31

<210> SEQ ID NO 109
<211> LENGTH: 32
<212> TYPE: DNA
<213> ORGANISM: Artificial sequence
<220> FEATURE:
<223> OTHER INFORMATION: PCR primer

<400> SEQUENCE: 109
ctctcctgca ggctgactgt ggcatacctc ta 32

<210> SEQ ID NO 110
<211> LENGTH: 31
<212> TYPE: DNA
<213> ORGANISM: Artificial sequence
<220> FEATURE:
<223> OTHER INFORMATION: PCR primer

<400> SEQUENCE: 110
ctctgtcgac gatagaagaa gtaggcacct c 31

<210> SEQ ID NO 111
<211> LENGTH: 30
<212> TYPE: DNA
<213> ORGANISM: Artificial sequence
<220> FEATURE:
<223> OTHER INFORMATION: PCR primer

<400> SEQUENCE: 111
ctctgtcgac caatctgtat ggttgcctcg 30

<210> SEQ ID NO 112
<211> LENGTH: 1053
<212> TYPE: DNA
<213> ORGANISM: Escherichia coli

<400> SEQUENCE: 112
atgaattatc agaacgacga tttacgcatc aaagaaatca aagagttact tcctcctgtc 60
gcattgctgg aaaaattccc cgctactgaa aatgccgcga atacggttgc ccatgcccga 120
aaagcgatcc ataagatcct gaaaggtaat gatgatcgcc tgttggttgt gattggccca 180
tgctcaattc atgatcctgt cgcggcaaaa gagtatgcca ctcgcttgct ggcgctgcgt 240
gaagagctga aagatgagct ggaaatcgta atgcgcgtct attttgaaaa gccgcgtacc 300
acggtgggct ggaaagggct gattaacgat ccgcatatgg ataatagctt ccagatcaac 360
gacggtctgc gtatagcccg taaattgctg cttgatatta acgacagcgg tctgccagcg 420
gcaggtgagt ttctcgatat gatcacccca caatatctcg ctgacctgat gagctggggc 480
gcaattggcg cacgtaccac cgaatcgcag gtgcaccgcg aactggcatc agggctttct 540
tgtccggtcg gcttcaaaaa tggcaccgac ggtacgatta aagtggctat cgatgccatt 600
aatgccgccg gtgcgccgca ctgcttcctg tccgtaacga aatgggggca ttcggcgatt 660
gtgaatacca gcggtaacgg cgattgccat atcattctgc gcggcggtaa agagcctaac 720
tacagcgcga agcacgttgc tgaagtgaaa gaagggctga acaaagcagg cctgccagca 780
caggtgatga tcgatttcag ccatgctaac tcgtccaaac aattcaaaaa gcagatggat 840
gtttgtgctg acgtttgcca gcagattgcc ggtggcgaaa aggccattat tggcgtgatg 900
gtggaaagcc atctggtgga aggcaatcag agcctcgaga gcggggagcc gctggcctac 960
ggtaagagca tcaccgatgc ctgcatcggc tgggaagata ccgatgctct gttacgtcaa 1020
ctggcgaatg cagtaaaagc gcgtcgcggg taa 1053

<210> SEQ ID NO 113
<211> LENGTH: 2964
<212> TYPE: DNA
<213> ORGANISM: Corynebacterium glutamicum -continued

<400> SEQUENCE: 113
atgctaggca tgcttcgatg gactacagca ggtgaatccc acggccaggc gcttatcgcc 60
acggttgaac acatgccagc aggcgtgccc gtgactaaag atgaggtctc gtatcaattg 120
gcgcgccgac gccttggata tggtcgcggc gctcgcatga agtttgagca agacgcgttg 180
accttcctga ccggcatccg ccacggcctc actttgggta gccccatctc aatcatgatc 240
ggcaacactg agtgggataa gtggaccacc atcatgtcct ctgacgcttt ggacatggaa 300
gacccagaca acgttgcggc gatgtcttcg ggtcgcggtg caaaactgac tcgtccgcgt 360
ccaggccacg cagattacgc aggcatgctc aagtacggat tcgatgatgc ccgcaacgtg 420
ctggagcgtt cttcagcccg tgagacggca gctcgcgtgg cagcagcaac cgttgcgcgt 480
tccttcctcc gtgaaacctt gggcgtggag gtgctctctc acgtaatttc cattggtgcg 540
tccgagcctt acgtcggcgc ggagccaacc tttgcagata ttcaagcaat cgatgattcc 600
ccagttcgtg cattcggtaa agacgctgaa aaatccatga tcgcggaaat cgaggccgca 660
aagaaagccg gcgataccct cggtggcatc gtggaagtga ttgttgaagg cctacccatc 720
ggtttgggct cacacatttc tggcgaagat cgcctcgatg cgcagatcgc agctgcactc 780
atgggcattc aggccatcaa gggcgtggaa atcggtgacg gtttcgaaga agctcgtcga 840
cgtggctccg aagcccacga tgaagtgttc ctggatgaca acggcgtata ccgcaacacc 900
aaccgtgcag gtggcctcga aggcggcatg accaacggtg aaaccctgcg cgttcgtgct 960
ggcatgaagc caatttctac tgtgcctcgc gccctgaaaa ccattgatat ggaaaacggc 1020
aaggcagcaa ccggaatcca ccagcgttcc gacgtgtgcg ctgttccagc cgccggtgtc 1080
gttgcagaag caatggtcac cctggttctc gcccgcgcag tcctgcagaa attcggcggt 1140
gactccctga gtgaaaccaa gagcaacatt gacacctacc tcaaaaacat tgaggaacga 1200
atgaaattcg aaggtttaga ggatggagcg taatgaagtg aatgatcaaa ttcacttaga 1260
tcatcaatca gatgacacct ctgaatgctc ctgcccgatc gtggttcttg tgggtttgcc 1320
aggagctgga aaatccacca ttggacgtcg attagcgcgc gccttaaaca ctgaactcgt 1380
cgactccgac gaactcattg agcgcgccac cggaaaagcc tgcggcgccg tgttcagcga 1440
gctcggcgag ccagccttcc gcgagctcga ggccatccac gtggccgaag cactgaaatc 1500
ctccggagtg gtgagcttgg gaggcggatc tgtgctgaca gaatccaccc gtgaactgct 1560
caaaggccac gacgtggtct ggatcgacgt gccagtagaa gaaggcatca ggcgcaccgc 1620
aaacgagcgt tcccgccccg tgctgcaagc cgccgacccc gccgagcact accgcaacct 1680
ggtgaaagtg cgcaccccgt tgtacgaaga ggtggcaacc taccgacttc gcaccaacaa 1740
ccgcagcccc cagcaagtgg tggcagcagt gttgcatcat ctagaaatcg attaattaaa 1800
ccgggcacct gattaacatt gggctgcccg gtttcttcct attacaagcg aaaggcaacg 1860
tgccccatga gcgcagcgca gattttcaac accgtccacg tcaatggatc ttccccctat 1920
gatgtccaca ttggttccgg cctcaacgag ctcattgttc agcgcgcagc ggaatcaggc 1980
gcggagcagg tagcgatttt gcaccagccc agcatggatg acattgcatc cgagttggat 2040
gcagcactag tcgctgctgg tttgaaggtc ctgcacctta atgttcccga tgcggaaaac 2100
ggcaagtcct tggaagtagc ggggcagtgc tgggatgaat tgggtggcgc agcattcggc 2160
cgccgcgata tcgtcatcgg acttggtggc ggtgctgcca cagatctcgc gggattcgtc 2220
gctgctgcgt ggatgcgtgg cgtgcgcgtc attcaggttc caaccacctt gttggccatg 2280
gtggacgctg cggtgggcgg caagactggc atcaataccg ccgcaggcaa gaaccttgtg 2340
ggcgcgttcc acgagcctga cgcagtattc attgacaccg aacgcctagc caccctgcct 2400
gacgcggaaa tcatcgcggg atccgccgaa atcatcaaaa ctggtttcat cgccgaccca 2460
gaaatcctgc gcctttacga aactgatccc gcagcctgcc tgaagaaaga agtcgaaggc 2520
tcccacctac ctgaactgat ttggcgctcc gtcaccgtca agggctccgt ggtcggccaa 2580
gacctcaaag aatctagcct gcgcgaaatc ctcaactacg gacacacctt tgcccacgcc 2640
gtcgaactcc gcgaaaactt ccgctggcgc cacggcaatg ccgttgcagt gggcatgatg 2700
ttcatcgcta acctctccca caagctcggg cttatcgacg cgcccctcct cgagcgccac 2760
cgctcaatcc tggcggccat cggtctgccc acttcctacg aaggcggagc cttcgacgag 2820
ctttacgacg gcatgacccg cgacaagaaa aaccgcgacg gcaacatccg cttcgtcgca 2880
ctgaccgccg tgggcgaggt tacccgcatt gaggggccct caaaacaaga tttacagagt 2940
gcttatgagg caatcagcca ctaa 2964

<210> SEQ ID NO 114
<211> LENGTH: 1293
<212> TYPE: DNA
<213> ORGANISM: Corynebacterium glutamicum

<400> SEQUENCE: 114
atggtctttg tgtctgattc gtctatctct ttgcccattt gggatgctcc gcgcgctcgc 60
ggccccatag tctcggacct ggctatccct ggttccaagt cgatcaccaa ccgcgccctc 120
atcttggctg cgctcgcatc aactccatcc accatcattg atgtccttcg tagtcgtgat 180
accgatctca tgactgatgg tctacgcagc ctcggaatca ccattactga agaggcagtc 240
gatcgctacc gcgttgagcc cggacagttg tctgctggct ccgttgagtg tggtcttgct 300
ggtacggtca tgcgcttttt gcctcctgtt gctgctttcg ctgatggtcc tgttcatttt 360
gatggcgatc ctcaagctcg tgttcgtccg atgaccagca ttttggatgc gctgcgttcg 420
cttggtgtgg aggtggacaa caacaatctg cctttcactg ttaatgctgg tgaggtccct 480
gagggtggcg tggttgagat tgatgcttcc ggctcatctc agtttgtttc tggtcttttg 540
ctttcagcgc ctcgttttaa aaatggcgtc accgttaagc acgtcggtgg tcgtctgccg 600
agcatgccgc atattgagat gaccgtcgat atgcttcgtt ccgcaggcat tgagatcgaa 660
gagtcagaaa atcagtgggt tgttcatcct ggtgagatct tgggtcggac ctggcgcatt 720
gagccggatc tttctaatgc gactccgttc ctagctgccg ctgcggtcac tggtggaacc 780
atcaagatta atcactggcc aatcaaaact actcagcctg gcgatgctat tcgttcgatt 840
cttgagcgca tgggctgcga agttgagctg gttgctcagg gtgaaggtta cgatctgtcg 900
gtgactggtc cggttgctct caagggcatt gagatcgata tgtccgatat cggtgagttg 960
acccctaccg tggcggcgtt ggctgcgttg gcgtcgacag agtctcgttt gaccggtatt 1020
gctcatcttc gtggccatga gacggatcgt ttggctgcgt tgactgcgga gatcaacaaa 1080
cttggtggaa agtgcactga gcttaaggat ggtctgttga ttgagcctgc gtcgctgcac 1140
ggtggtgtgt ggcattcata tgctgatcat cgtatggcta ctgctggtgc gatcattggc 1200
ctcgcggttg atgacgttca ggttgaagac attaagacca cttccaagac tttccctggt 1260
tttgaaaatg tttgggagga gatggttggc tag 1293

<210> SEQ ID NO 115
<211> LENGTH: 438
<212> TYPE: DNA

<213> ORGANISM: Corynebacterium glutamicum

<400> SEQUENCE: 115
atgcttggaa aaattctcct cctcaacggc ccaaacctga acatgctggg caaacgcgag 60
cctgacattt acggacacga caccttggaa gacgtcgtcg cgctggcaac cgctgaggct 120
gcgaagcacg gccttgaggt tgaggcgctg cagagcaatc acgaaggtga gctaatcgat 180
gcgctgcaca acgctcgcgg cacccacatc ggttgcgtga ttaaccccgg cggcctgact 240
cacacttcgg tggcgctttt ggatgcggtg aaggcgtctg agcttcctac cgttgaggtg 300
cacatttcca atccgcatgc ccgtgaagag ttccgccacc attcttacat ttccctcgcc 360
gcggtctccg ttatcgctgg cgctggcatc cagggttacc gtttcgcggt cgatatcctg 420
gcaaatctca aaaagtag 438

<210> SEQ ID NO 116
<211> LENGTH: 831
<212> TYPE: DNA
<213> ORGANISM: Corynebacterium glutamicum

<400> SEQUENCE: 116
ataaggatca acgaataaaa ttgggttctc acatcactca ccgggcggcc gtactcggct 60
cacccatcga gcattccaaa tccccagtcc tccacaacac cggctataaa gccctcggac 120
tggaccaatg ggaatacgac cgctttgagt gcaccggcga catgctcccc ggaatcgtct 180
ccggcgctga tgaaacctac cgcggattct ccgtcactat gccgtccaaa ttcgcagccc 240
tcgaattcgc cgacgaagta accgaacgcg cccgcgccat cggctccgca aacacacttc 300
tgcgcaccga aaccggatgg cgcgcagaca acaccgacgt cgacggcatc aggggagccc 360
tcggtgaact cctcggcagc gcatcactgg ccggcaaaca cgccatcgtc atcggctccg 420
gcggcaccgc acgccccgcc atctgggcac tcatcgaagc cggggtcgcg cggatcacgg 480
tgctcaaccg ctccgatcga accgccgaac tgcaaacgct tttcgacgaa acccccacca 540
ccttggccta cgccccgctc gaacatctcg acatcgaagc cgacgtcgta gtctctacag 600
tgccctccgc agcaatcgca ggcctcgaag acacactcgc aatcgcccca gtcctcgacg 660
tcatctacga tccttggcca acaccactcg tagaagtcgc acgagccaaa ggtctcaaag 720
ctgtcggagg ccacgtcatg ctggcacacc agtcctacgg acagtttgaa caattcaccg 780
gaatggatgc accccgcgat gctatgcgtg aggctttgga agaatcccta g 831

<210> SEQ ID NO 117
<211> LENGTH: 37
<212> TYPE: DNA
<213> ORGANISM: Artificial sequence
<220> FEATURE:
<223> OTHER INFORMATION: PCR primer

<400> SEQUENCE: 117
ctctgatatc atgaattatc agaacgacga tttacgc 37

<210> SEQ ID NO 118
<211> LENGTH: 30
<212> TYPE: DNA
<213> ORGANISM: Artificial Sequence
<220> FEATURE:
<223> OTHER INFORMATION: PCR primer

<400> SEQUENCE: 118
ctctgatatc gacttatcag gcctgtggtg 30

<210> SEQ ID NO 119
<211> LENGTH: 24
<212> TYPE: DNA
<213> ORGANISM: Artificial sequence
<220> FEATURE:
<223> OTHER INFORMATION: PCR primer

<400> SEQUENCE: 119
tttgtccggt cggcttcaaa aatg 24

<210> SEQ ID NO 120
<211> LENGTH: 19
<212> TYPE: DNA
<213> ORGANISM: Artificial sequence
<220> FEATURE:
<223> OTHER INFORMATION: PCR primer

<400> SEQUENCE: 120
aaagccctga tgccagttc 19

<210> SEQ ID NO 121
<211> LENGTH: 31
<212> TYPE: DNA
<213> ORGANISM: Artificial sequence
<220> FEATURE:
<223> OTHER INFORMATION: PCR primer

<400> SEQUENCE: 121
ctctcatatg ttacgctcca tcctctaaac c 31

<210> SEQ ID NO 122
<211> LENGTH: 33
<212> TYPE: DNA
<213> ORGANISM: Artificial sequence
<220> FEATURE:
<223> OTHER INFORMATION: PCR primer

<400> SEQUENCE: 122
ctctcatatg ttagtggctg attgcctcat aag 33

<210> SEQ ID NO 123
<211> LENGTH: 29
<212> TYPE: DNA
<213> ORGANISM: Artificial sequence
<220> FEATURE:
<223> OTHER INFORMATION: PCR primer

<400> SEQUENCE: 123
ctctccatgg tctttgtgtc tgattcgtc 29

<210> SEQ ID NO 124
<211> LENGTH: 28
<212> TYPE: DNA
<213> ORGANISM: Artificial sequence
<220> FEATURE:
<223> OTHER INFORMATION: PCR primer

<400> SEQUENCE: 124
ctctccatgg ctagccaacc atctcctc 28

<210> SEQ ID NO 125
<211> LENGTH: 31
<212> TYPE: DNA
<213> ORGANISM: Artificial sequence
<220> FEATURE:

<223> OTHER INFORMATION: PCR primer

<400> SEQUENCE: 125
ctctcatatg cttggaaaaa ttctcctcct c 31

<210> SEQ ID NO 126
<211> LENGTH: 37
<212> TYPE: DNA
<213> ORGANISM: Artificial sequence
<220> FEATURE:
<223> OTHER INFORMATION: PCR primer

<400> SEQUENCE: 126
ctctcatatg ctactttttg agatttgcca ggatatc 37

<210> SEQ ID NO 127
<211> LENGTH: 28
<212> TYPE: DNA
<213> ORGANISM: Artificial sequence
<220> FEATURE:
<223> OTHER INFORMATION: PCR primer

<400> SEQUENCE: 127
ctctcatatg ggttctcaca tcactcac 28

<210> SEQ ID NO 128
<211> LENGTH: 30
<212> TYPE: DNA
<213> ORGANISM: Artificial sequence
<220> FEATURE:
<223> OTHER INFORMATION: PCR primer

<400> SEQUENCE: 128
ctctcatatg ctagtgttct tccgagatgc 30

<210> SEQ ID NO 129
<211> LENGTH: 1929
<212> TYPE: DNA
<213> ORGANISM: Ralstonia eutropha

<400> SEQUENCE: 129
atggtagcca gcatccagcc cccgccctct cccccggccc ctctcccgca agcgggcgag 60
gggagcaccc agccaggggg aggagatgtc ttcgtccttc tcgacgacgc cacggccccg 120
gcggcgcaag ccgcatcacg cctctacacc ggcttcatcc gtgaagacgt cttgcccgcc 180
ggcagcgaca tcgcgcaact cgacaccatg cttgccgaag gctggcgcca gggctggcat 240
gccaccctgt ttgcccccta cgaattcggc ggcgcgctgg tcgatgcccc ggtgcacacc 300
ggcaacgcga tgccgttcca cgacggcgcg ctgcgcctgc tgtggttccg caacctgcgc 360
cggctcgatg ccgcggcggt cacggcgtgg ctgcaggcga aagccgaccc caggccggcg 420
ggcctgatgg acgtggcctc cgatacctcc cgcgaggcat tcgacgatgc catcgcccgc 480
atccaccagt ggatcgaagc cggcgacacc taccaggtca actacaccca gcgcctgcac 540
ttcgatgcct ttggcgaccc ggtggcgctg tatgccgcgc tgcgcgccgc gcagccggtg 600
ccgtatggcg tgctggccag cctgccggat cgtgccacgg tgctgtcgct gtcgcccgag 660
ctgttcgtgc gccacgacgg ccagggccac atgctgaccc ggccgatgaa gggcaccgcg 720
ccgcgctcgg gcgatgccgt gcgcgatgcg caggccgccg ccgcgctggc cgccgatgcc 780
aagaaccgcg ccgagaacgt gatgatcgtc gacctgctgc gcaacgacct ggggcgcatc 840
gcgcagccgg gcagcgtggc ggtgccggag cgctttgcgg tgcagccgtt tggcgcggtg 900
ctgcagatga cctctaccgt caccgcgacg gcgcggcccg gcacgcgctt tggcgcgctg 960
atggcggcgc tgttcccgtg cggctccatc accggcgcgc ccaagcggcg caccatgcag 1020
atcattgccg aactggaagg cacgccgcgc gggctgtaca ccggggcgat cggctggatc 1080
gatgcgccaa ccgacgaagg caccgcggga ccgttcgcgc tgtcggtggc aatccgcacg 1140
ctggtactgg cgcctctcgc ggataccggc ctgcgcgcgg gtgaaatggg cgtgggcggc 1200
ggcatcgtcc atgacagcgt cgcggcggag gagttcgatg aatgcggctg gaaggcgcgt 1260
ttcctgacgc ggcacgatcc cggttttacg ctgttcgaaa ccatgcgcgt gcaggacggc 1320
gagtgccttt acctggcgcg gcatcttgcg cgcattggcg cttcggcaca tacgttcggc 1380
ttcgctttcg atgccgatgc ggcacgcaac gcggtggccg cgcaggtagc gcagctgggc 1440
gcggggacat ggcgcctgcg tatgagcgtg gacaagcgcg gcgcgctcgc atttgccagc 1500
ggcgcggtgg caccgatgcc ggccggtccg gtcaggatcg atatcgcccc cgagccacta 1560
cccgccgccg atccgctgcg ccgccacaag accagcgcgc gcgcagtgtt cgatgcgggc 1620
tggcaggccg ccgagcgtgc cggtggcttt gacctgctgt tcttcaacac gcgcggtgaa 1680
ctgctggaag gcgggcgcag ctcggtcttc gtccgtatcg atggccgctg gctgacgccg 1740
ccgctgtcgg ctgacatcct gcccggcgtg atgcgcgcgg tggcgctgga cgagggaggg 1800
gcggccctgg gcgcccccgg cgaagtggtg acggaagcgg tgatcacgcg cgcgatgctc 1860
gcgcgcgccg aggccatcgt cctggtcaac gccttgcgcg gcgcgatgcc ggcgacgctg 1920
agtcagtaa 1929

<210> SEQ ID NO 130
<211> LENGTH: 27
<212> TYPE: DNA
<213> ORGANISM: Artificial sequence
<220> FEATURE:
<223> OTHER INFORMATION: PCR primer

<400> SEQUENCE: 130
ctctcatatg gtagccagca tccagcc 27

<210> SEQ ID NO 131
<211> LENGTH: 30
<212> TYPE: DNA
<213> ORGANISM: Artificial sequence
<220> FEATURE:
<223> OTHER INFORMATION: PCR primer

<400> SEQUENCE: 131
ctctcatatg ttcaggctta ctgactcagc 30

<210> SEQ ID NO 132
<211> LENGTH: 1497
<212> TYPE: DNA
<213> ORGANISM: Corynebacterium resistens

<400> SEQUENCE: 132
atgacggccg atcgcgatgc gaacttacct gcgtggcacc ctcaactgct acggcttcac 60
tttcagacca tccccatcga agcggacggc tcggcgcttt tcgatactct cttcgcaggc 120
tcccacaatg ccgtctggct ggattcgcca ggtgcttcca cctctgtgtt gtgcgatgac 180
tccggcccgt ttgcccactc actttttatc gacgccaaca ccacggccgc ttctaacaat 240
gccttcgacc aggcccagga gctgctcgat atttataccg tggagattcc cccggagctc 300

-continued

```
ccgtgtgatt tcgctttagg cttggtgggc gcatttggtt acgagttaaa aactcatgca    360
ggcgctacat gcaatgcgca atcgccttcg cctcaccttg aacctcttcc tgatcttgct    420
ctgatttaca ctgatcgcgc tgtagtcatc gaccacaaaa accagcagac tcacctgctg    480
tatctgctac cagtcgaaaa cgagtaccac gaactgcaga aagcgtggtt gcaacgggtc    540
atcaacgcga tcgaggaacg ccccgcaacc accggagcaa atccgttagc agcccagaat    600
tcttcgcccc ctcttccggc acctaagttc actctcgatc aatccaagtt cgaatacctc    660
gaatcgattg cgcgttgttt ggactacatc gctgctggtg attcatacga aatctgcctg    720
acaaacacgg cacaggggcc cagtatggct gaaattggct tagagcccat cgatgcctat    780
tcggccctcc gccacaccag cccagtgcca tatggcgcct acttacagtt cacgccgcgt    840
caagcggggt atgtgccgtt tcagctcctc agtgcttcgc ctgaacaatt cctcaaaatc    900
actaacgggc acgtcaccgc gcaacctatc aagggaactc ggccacgagg tcggaatgcg    960
gaggaggacg cggcgtggcg tcgagaatta aaaacaaacc ccaaagaccg agccgagaat   1020
ctgatgattg tcgacctatt gcgcaatgat ttaggtcggg tctgccagcc cggcaccgtt   1080
cgcgtgccac gaattttcgc ggtggagact tatagccacg tgcatcagct ggtcagcaca   1140
attgaaggtc atttagcacc gggagtgaca actttgaaat gcgtggcggc atgcttcccc   1200
ggtggatcaa tgaccggtgc accgaaactg cggacgatgg aaatcattga tgaactcgag   1260
aagcggccgc gaggattcta ttcgggtgca gtggggtggg tctcgccaaa cggatctgcc   1320
gacttgtcga tcgtgattcg cacgctggtg tgctcaccga atgcaacgac ctttggtgtt   1380
ggcggtgcaa ttgtgtggga ttcagatccg gagggcgagt tcgcagaaac aatggtgaag   1440
gcgcgagctc tgctggaagc gcttggagcg gacatcgaag ataagccaac gttctaa      1497
```

<210> SEQ ID NO 133
<211> LENGTH: 1593
<212> TYPE: DNA
<213> ORGANISM: Corynebacterium falsenii

<400> SEQUENCE: 133

```
atgcctaacc ccgcctcggg cgcattccgc cgccctcgcc tcgccttccg cacccttccc     60
attgaggtgc cgggagctgt ggtgtggcgg accctttttt ccgacgccac cacgcccgcc    120
atctggctcg attcctcctc gagtgaccag caggagggtc accaccaggg gcacggcggt    180
gcgggtcgat tctctatcct ctgcgatgcc agcggacccg gcgcggagta tctccgctat    240
acggtcggaa agcccggaga gcccggagga aacggtggat tattcgccca cgtagcgcgg    300
cgtgtggcgc tgggcgatac cgacctggcg gtaccggagg actggccatg tgaattcgcc    360
ctggggtggg tgggcgcgtg ggggtatgag ctgcgacatc ttatcgagcc ggcgcacggg    420
gtgggctcgg cgcagggcgc cccggacctt ccccaggcac cggatgcggc gctgatcttt    480
gcgacccgcg cggtcgttat tgagcacggt gtgggcacgc acctgatggt gctcacagat    540
gaggccaacc cagccaccgc cgcagagcag caggactggc tggatgccac ggacgctcgc    600
ctgcgcgatt ccgtccctgc accgtcccct cgcagtgact accgccccat gcaaccgggc    660
cgggatgttc ccttccgctt cgtgcagtcc aagcagcgct acctggacaa catcaatcgc    720
tgcttggagt acatcgctgc gggcgactcc tacgagatct gcctgaccaa caccgcgata    780
ggcccaagca tcgcggacat tgtccctttg gaggccacga aggccacgca ggccacagag    840
accgcagtac ccacagaacg cgacccctac ctcgccgctt tcgagcgact gcgcgcggtg    900
agccccgtgc cgtatggagt gttcgcccgg ttccccggta cgtccgaggg ggaacgggat    960
```

-continued

```
gtgcgggtgc tgggggcgtc gccggagagg ttcctcaagg tcagcgcggg cgggcatgtc   1020
agcgccaagc cgatcaaggg aacgcggccg cgcgcaacca gcccggccgc cgatgcgcgt   1080
atcgcagatg agctgcgggg caacccgaag gatcgcgcgg aaaacctcat gatcgtggac   1140
ttgctgcgca acgatatcgg ccgcgtatgc acaacgggca gcgtacaggt gccggtgatc   1200
ttcgatgtgg aaacgtactc tcacgtgcac caactggtga gcaccatcga agggcagttg   1260
gccccgggcc actcggtggt ggatctgctg gtggcctgct tccccggcgg atccatgact   1320
ggcgcgccga aggtgcggac gatggagatc atcgcggagc tggaaggcat gccgcggggg   1380
ctgtattccg gcgcgattgg gtggctatcg ccaactgggg ctggggatct gagcatcacg   1440
atccgcacgc tggtggatga cggccaacgg gcgagcttcg gcgtgggtgg ggcgatcgtg   1500
gcggattccg atccggaggc ggagttcgag gagacgctgg tgaaggcctc tgcgctgctc   1560
gatgcgctgg gggcctacct ggaattcagc tag                                1593
```

<210> SEQ ID NO 134
<211> LENGTH: 1413
<212> TYPE: DNA
<213> ORGANISM: Bacillus subtilis

<400> SEQUENCE: 134

```
atggcacaac gcagaccggc aggcaaaaaa atacctttc aaaaagactc attcttacaa      60
caatttgaga aacttgcgca atcccggaaa catcatgtac ttctcgaaag tgcaagaggc   120
ggcagatata gtatagccgg tcttgatcca attgcgactg tgaaaggaaa agacggaata   180
actacaatta agcatggtga tgagatgctg tttaaagaag gtgatccatt acgggccttc   240
cacagctggt ttaaaacact ggaaacagaa acgaatcatg agttccctga ctttcaaggc   300
ggggcaatcg ggtttctcag ctatgattac gcacggtaca ttgaaaattt taaaatgctc   360
tcattagatg atttagaaac accagatatt tattttcttg tttttgatga tatagcagtt   420
tatgaccatc aagaagagtc tctatggctg attactcatg ttaatggttc tgatcaggaa   480
acagcggatg tgaagctatc tgagttagag cagatgtggt tgactgagct tcccgctgtc   540
acttcgcgag agatgaagcc tgaaacagct ggttctttcg cggcgccatt taccgaggat   600
gggttctcac aagctgtaga gaaaatcaaa caatacattg ccagcggaga tgtgtttcaa   660
gtcaatctat caataaggca gtcacagtca ctgtctgtcc acccatatca aatttacaaa   720
accttgagag aagtaaatcc ttctccttat atggcgtatt tagaaacacc tgatttccaa   780
atcatttgcg gatcgcctga actgcttgtc agcaaaaagg gcaagctatt agagacgaga   840
ccgattgcgg gcacccgttc cagagggaaa acaaatgaag aagacgaggc gcttgcaaac   900
gaattgatac acaatgaaaa agaacgcgcg gaacatgtca tgctggttga tcttgagcga   960
aatgatctgg gaagagtatc acgttacggg tctgtgcgcg taaatgaatt catggcaatt   1020
gaaaaatact cgcatgtgat gcacattgtg tctaatgtcc aaggtgaact gcaggatggg   1080
tatgatgctg tagatattat tcatgctgtg tttcccggag gaaccattac tggtgcaccg   1140
aaagtaagaa cgatggaaat tatagaagaa cttgagccga cacgccgagg gctttatact   1200
ggatctatag gatggtttgg atataatcac gatctgcagt ttaatatcgt cattcgaacc   1260
atttatgcaa ccggagggca ggcatttatg cagtccggtg caggagttgt gattgattct   1320
gttccgaagc acgaatacaa ggaatcattc aaaaaagctt ttgcgatgca aagagcatta   1380
gagctgagcg aagaagagac aaaaattaga tga                                1413
```

<210> SEQ ID NO 135
<211> LENGTH: 1413
<212> TYPE: DNA
<213> ORGANISM: Bacillus amyloliquefaciens

<400> SEQUENCE: 135

```
atggcacaac gcagaccggc aggaagaaga atacctttta cgaaacaagc atttttacag     60
cagtatgaaa acctttcgaa atcgagaaaa cggcatgttc tgctcgaaag cgcgagaggg    120
ggaagattca gtatagccgg tctagatccg attgcgtccg tcaaggggaa agacggaatt    180
acgacaatca agcatgaagg ggaaacgctg tttaaagaag gtgacccgct gcgggccttt    240
catgagtggt ttgaggcgct tgggacggaa acaaacgatg agttcccgga cttccaaggc    300
ggcgcaattg gctttatcag ttacgactac gcccgatata ttgagaattt taagatgctg    360
tctttagatg atttggaaac acctgatatt tactttctcg tttttgacga tgtggccgtt    420
tatgaccatg aggaagaggc gttatggctc attactcata ccgaatcgga agaagcggag    480
cttgcggaag agaagctgtc cggcttagag gatatgtggt gttccctcca aacggaggac    540
gagccttatt caccgctgaa ccgggacgga gacggatcgt atgccgctcc gttcactgaa    600
gaaggatttt cacaggctgt agaacaaatt aaacaatata ttgcgagcgg tgatgtgttt    660
caggttaatt tgtccatcag gcaatcccag tccttatccg ttcatccgta tgaagtgtat    720
aaacatttga gaaacgttaa tccgtctcct tacatggcct atctggagac gccgggtttt    780
caagtgatat gcgggtcgcc ggagctattg gtaacaaaaa aggggaagaa gcttgaaatg    840
agaccgatcg cgggtacgcg ttcaagagga aaagacgatg ctgaagacaa ggcgcttgct    900
gatgaattaa ttcacaatga aaaagaacgt gcggaacacg tcatgcttgt tgatcttgag    960
cgcaatgatc tcgggcgcgt atcgcgctac ggctccgtgc gggtgaacga gtttatggcg   1020
atcgaaaagt actcccacgt catgcatatc gtgtcaaatg tacagggaga actgcaggac   1080
ggatatgacg cgacagatat tattcatgcg gtttttccgg gcggcaccat cacgggagcg   1140
cccaaagtga gaacgatgga aattatagaa gagcttgagc cgacaagacg agggctttat   1200
actggatcta taggctggtt tggatttaac ggagatttgc agtttaacat tgtaatccgg   1260
acgatctatg cagccggagg acatgctttt atgcagtccg gcgcaggagt ggtcattgac   1320
tcggttccga agcatgaata caaggaatcg ttcaaaaaag cttttgcgat gaaaaaggca   1380
ttagagctga gcgaagaaga gacaaaaaat tag                                1413
```

<210> SEQ ID NO 136
<211> LENGTH: 1398
<212> TYPE: DNA
<213> ORGANISM: Bacillus thuringiensis

<400> SEQUENCE: 136

```
atgcaacgaa gaaaatcttt agcgctttct attccatatc agttagattt ctttaagcaa     60
tataaatttc tttctaagga taaaccgcaa cacattttgt tagagagtgg acgtggcggt    120
cgttataaca tcgtgggatt aaacccagta gcggtaatcc gagggaaggg tgaagcgtta    180
catataagtg aaagtggtaa ggaaacaata aagcaaggaa acccattgga tttaatgcag    240
gaatatatgg agcgatggaa aacggattat aatccggaat acccgccttt tcaaggtggt    300
gcaattggtt actttagtta tgattgcatc cgttatattg aaaaacttcc ttctcttgcg    360
gaggatgata ttaatatacc tgatatattc tttttattat ttgatgatgt gtttgtgtat    420
gatcaaaaag aaaaagtatt atggattatt acacattatg tagataagca tgaagaggca    480
```

aaagagcgat taaatgaatg gaagattctt tgggcgacag aagcgccgga agtgactata 540
ccgtttgcgt gccctgaaaa gaaaaatgaa gcagttgctt ttactgaaga aagctttatg 600
aaggcggttg aatgtattca agaatatatt ggggctggtg atgtgttcca agtaaacttg 660
tcgacaagac aagaaagaac gttacaaaca cacccactag aaatatatac aagtcttcgt 720
gaaattaatc catctccata tatgggttac ttggagctcg gggattttca aattgtaagt 780
ggatcgccag agttgctaat taagaaacag ggaactgaag taagtacaag accaattgct 840
ggaacgagat ctagaggggc aaatgaacaa gaggatgaag aattggcaag ggaattaatt 900
gagaatgaaa aagaaagagc agagcacgtc atgcttgtgg atttagaacg aaatgattta 960
ggacgtgttt gtaaatatgg cactgtagaa gtagacgagt ttatggtaat tgagaaatac 1020
tcacatgtta tgcatattgt ttctaatgtg cgtggtgagg tggaagaaga taaagatgct 1080
ttcgatttag tgaaggctgt attccctgga ggaacaatta cgggtgctcc gaaaatacgt 1140
acgatggaaa ttattgaaga attagaacct gttcgccgag ggatttatac aggttcaatc 1200
ggttggattg gttattctgg agatacagaa ttgaatattg taattaggac acttcttgct 1260
aaagacggaa aagcgcatgt acaagcaggg gcgggaattg taattgattc aaatccggaa 1320
aatgaatata aagagtcgtt aaaaaaggcg attgctttat ggcgtgcaaa agaacgtagc 1380
gaagaaacgg ttaggtga 1398

<210> SEQ ID NO 137
<211> LENGTH: 1362
<212> TYPE: DNA
<213> ORGANISM: Escherichia coli

<400> SEQUENCE: 137
atgaagacgt tatctcccgc tgtgattact ttactctggc gtcaggacgc cgctgaattt 60
tatttctccc gcttaagcca cctgccgtgg gcgatgcttt tacactccgg ctatgccgat 120
catccgtata gccgctttga tattgtggtc gccgagccga tttgcacttt aaccactttc 180
ggtaaagaaa ccgttgttag tgaaagcgaa aaacgcacaa cgaccactga tgacccgcta 240
caggtgctcc agcaggtgct ggatcgcgca gacattcgcc caacgcataa cgaagatttg 300
ccatttcagg gcggcgcact ggggttgttt ggctacgatc tgggccgccg ttttgagtca 360
ctgccagaaa ttgcggaaca agatatcgtt ctgccggata tggcagtggg tatctacgat 420
tgggcgctca ttgtcgacca ccagcgtcat acagtttctt tgctgagtca taatgatgtc 480
aatgcccgtc gggcctggct ggaaagccag caattctcgc cgcaggaaga tttcacgctc 540
acttccgact ggcaatccaa tatgacccgc gagcagtacg gcgaaaaatt tcgccaggta 600
caggaatatc tgcacagcgg tgattgctat caggtgaatc tcgcccaacg ttttcatgcg 660
acctattctg gcgatgaatg gcaggcattc cttcagctta atcaggccaa ccgcgcgcca 720
tttagcgctt ttttacgtct tgaacagggt gcaattttaa gcctttcgcc agagcggttt 780
attctttgtg ataatagtga aatccagacc cgcccgatta aaggcacgct accacgcctg 840
cccgatcctc aggaagatag caaacaagca gtaaaactgg cgaactcagc gaaagatcgt 900
gccgaaaatc tgatgattgt cgatttaatg cgtaatgata tcggtcgtgt tgccgtagca 960
ggttcggtaa aagtaccaga gctgttcgtg gtggaaccct tccctgccgt gcatcatctg 1020
gtcagcacca taacggcgca actaccagaa cagttacacg ccagcgatct gctgcgcgca 1080
gcttttcctg gtggctcaat aaccggggct ccgaaagtac gggctatgga aattatcgac 1140

-continued

```
gaactggaac cgcagcgacg caatgcctgg tgcggcagca ttggctattt gagcttttgc   1200

ggcaacatgg ataccagtat tactatccgc acgctgactg ccattaacgg acaaattttc   1260

tgctctgcgg gcggtggaat tgtcgccgat agccaggaag aagcggaata tcaggaaact   1320

tttgataaag ttaatcgtat cctgaagcaa ctggagaagt aa                      1362
```

<210> SEQ ID NO 138
<211> LENGTH: 1362
<212> TYPE: DNA
<213> ORGANISM: Escherichia fergusonii

<400> SEQUENCE: 138

```
atgaagacgt taactcccgc tgtgattact ttaccctggc gtcaggacgc cgctgaattt     60

tatttctccc gcttaagcca cctgccatgg gcgatgattt tacattctgg ttatgccgat    120

catccgcata gtcgcttcga tattgtggtg gccgagccga tttgcacttt aaccactttc    180

ggtaaagaaa ccgttgttag tgaaggcgaa aaacgcacaa ctactaccga tgacccgcta    240

caggtgctcc agcaggtgct ggaccgcacc aacatttgtc caacacataa cgaagatttg    300

ccatttcagg gcggcgcact ggggttgttt ggctacgatc taggccgccg ttttgaatca    360

ttgcctgaaa ttgcggagca agatctcgat ctgcctgata tggcagtggg tatctacgac    420

tgggcgctga ttgtcgacca tcagcgtcag gtaatttctc tgctcagcca ttttgatgtc    480

aatgcccgcc tggactggct tgaaagccag caaatcacgt caaaacttga tttccagctc    540

acttctgcct ggcaatccaa tatgacccgc gagcagtacg gcgaaaaatt tcgccaggta    600

caggaatatc tgcacagcgg cgattgctat caggtgaatc ttgcccagcg ttttcaagcg    660

acctattctg gtgatgaatg gcaaatattc gttcagctta ataaggccaa ccgcgcgcca    720

tttagtgctt ttttgcgtct tgaacagggc gcgattttaa gcctttcgcc agagcggttt    780

atcctttgcg ataatagtga aattcagacc cgcccgatta aaggcacgct gccacgcctg    840

tccgaccctc agaaagatag caagcaggca gagaaactgg cgaactcccc caaagatcgc    900

gctgaaaatc tgatgattgt tgatttaatg cgtaatgata tcggtcgcgt tgccgtagcc    960

ggttcggtaa aagtaccaga gctgttcgtg gtcgaaccct tccctgccgt gcatcatctg   1020

gtcagcacca taacggcgcg gctaccagaa cagttacacg ccagcgatct gctgcgcgcg   1080

gctttcccag gaggctcaat aactggtgca ccgaaagtac gggctatgga aattatcgac   1140

gaactggaac cgcagcgacg caacgcctgg tgtggcagca ttggttattt gagcttttgc   1200

ggcaacatgg acaccaacat caccatccgc acgctgacgg cggttaacgg gcaaatttac   1260

tgttccgctg gcggtggtat tgtcgctgat agccaggaag aagcggaata tcaggaaact   1320

tttgataaag ttaataagat cctacgtcaa ctggagaaat aa                      1362
```

<210> SEQ ID NO 139
<211> LENGTH: 1062
<212> TYPE: DNA
<213> ORGANISM: Streptomyces coelicolor

<400> SEQUENCE: 139

```
gtgctcgacc tcccgcccct cgcccgcttc ggcgaccgtc tcgccaccgg tctcctcgac     60

gtcacgagtg atcccgccgc cctcgaatcc gaggggttct gggccgtctg cgcggacttc    120

gaaggcggcc tgacctgcgc acgcttcgcg gaggtacgga ccgagccggt gcccgcgccc    180

acgccggggg agtggcgggg gcccgccgtc ggcgactgga cgtcgtcgct cgaccgcgcc    240

gcgtacacga cgggcgtacg gcgtatccgc gcccacatag ccgcgggcga ggtctaccag    300
```

gccaacctct gccgggtgct gacggcaccg atcggcccgg gcgccgacgt ggacgccctc 360
accgccctgc tggcccgcgg caacccggcg ccgtacgccg ggacgatccg gctgccggag 420
cacggcgtcg agatcgccac cgcctcgccc gagctgttcc tgcgccggga cggccgcacg 480
gtcgagtccg ggccgatcaa ggggaccggg cggaccgagg ccgacctgct ggagaaggac 540
tacgccgaga acgtcatgat cgtggacctg gtccgcaacg acctggggcg cgtctgcgcc 600
accggcacgg tcacggtgcc cgacctgtgc gccgtcgaga agcacccggg cctcgtccac 660
ctggtctcca cggtgcgcgg cgagctgccc gccgacgccg gctggccgga cctgctcgac 720
gcggccttcc cgcccgggtc cgtcaccggc gcgcccaagt ccagcgccct gcggatcatc 780
gacgcgctgg agaccgcgcc ccggggcccg tactgcgggg gcgtcggctg ggtcgacgcc 840
gaccggggca cgggcgggct ggccgtcggc atccgcacct tctggctcga gcgggccgcc 900
ggcggcgagg cccggctgcg tttcggcacc ggcgccggca tcacctgggg ctccgacccg 960
gagggcgagt ggcgggagac cgaactgaag gccgcccggc tgctcgcggt agcgtcgggg 1020
gcgtacgagg tgaacgcgac gggagaggtg ctggcgacgt ga 1062

<210> SEQ ID NO 140
<211> LENGTH: 1056
<212> TYPE: DNA
<213> ORGANISM: Streptomyces griseus

<400> SEQUENCE: 140
gtgtccgacc tcgcccccttt ggcccgtttc gacggcctca tcgcctccgg tctgcaggat 60
gtgacccacg atcccgcggc tctcgactca tccggtttct gggcggtatg tgccgatttc 120
gaagggcgtc ccgtctgcgc ccgcttctcc gatgtgcgcc aggaggcggt gccccctccc 180
gtgcccggag cgtggcgcgg gcccgccacc ggcgactgga cctcctcgct ggaccgtgac 240
gcctacacgg cgggcgtccg gcggatccgt gaacacatcg cggcgggcga cgtctaccag 300
gccaacctct gccgggtgct gtccgcaccg ctccccggcg gcggggccgg ggcggatgtc 360
gacgccctga cctcgctgct cgcgcgcggc aaccccgccc cgtacgcggg aacgatccgg 420
ctgccgggcc acggcgtcga ggtcgccacc gcctccccgg aactcttcct ccggcgcgac 480
ggacggaccg tggagtccgg gccgatcaag ggcaccggcc gcaccgagaa cgacctgctg 540
gccaaggacc acgcggagaa cgtgatgatc gtggacctgg tccgcaacga cctcggccgg 600
gtctgcgcca ccggaagcgt gagcgtcccc gacctctgcg tcgtcgagaa acacccgggc 660
ctcgtccacc tggtctccac cgtccggggc cggctggccg acggggcggg ctggcccgag 720
ctgttctcgg cggccttccc gcccggctcg gtcaccgggg cgccgaagtc cagcgcactg 780
cggatcatcg ccgagctgga gcgggccccg cgcggaccgt actgcggggc catcggctgg 840
gtcgacgccg accggggcac ggcctcgctc gccgtcggga tacggacctt ctggatcgac 900
cggaccgggc ccgcgcccct gctgcggttc gggaccgggg ccgggatcac ctggggatcc 960
gacccggaac gcgaatggga cgagaccgag ctcaaggcct cccggctgct cgctgtagcg 1020
tcgggggcgc atctggagac ggaagggacc gcgtga 1056

<210> SEQ ID NO 141
<211> LENGTH: 1062
<212> TYPE: DNA
<213> ORGANISM: Streptomyces lividans

<400> SEQUENCE: 141

-continued

```
gtgctcgacc tcccgcccct cgcccgcttc ggcgaccgtc tcgccaccgg tctcctcgac     60
gtcacgagtg atcccgccgc cctcgaatcc gaggggttct gggccgtctg cgcggacttc    120
gaaggcggcc tgacctgcgc acgcttcgcg gaggtacgga ccgagccggt gcccgcgccc    180
acgccggggg agtggcgggg gcccgctgtc ggcgactgga cgtcgtcgct cgaccgcgcc    240
gcgtacacga cgggcgtacg gcgcatccgc gcccacatag ccgcgggcga ggtctaccag    300
gccaacctct gccgggtgct gacggcaccg atcggcccgg gcgccgacgt ggacgccctc    360
accgccctgc tggcccgcgg caacccggcg ccgtacgccg ggacgatccg gctgccggag    420
cacggcgtcg agagcgccac cgcctcgccc gagctgttcc tgcgccggga cggccgcacg    480
gtcgagtccg ggccgatcaa ggggaccggg cggaccgagg ccgacctgct ggagaaggac    540
tacgccgaga acgtcatgat cgtggacctg gtccgcaacg acctggggcg cgtctgcgcc    600
accggcacgg tcacggtgcc cgacctgtgc gccgtcgaga agcacccggg cctcgtccac    660
ctggtctcca cggtgcgcgg cgagctgccc gccgacgcag gctggccgga gctgctcgac    720
gcggccttcc cgcccgggtc cgtcaccggc gcgcccaagt ccagcgccct gcggatcatc    780
gacgcgctgg agaccgcgcc ccggggcccg tactgcgggg gcgtcggctg ggtcgacgcc    840
gaccggggca cgggcgggct ggccgtcggc atccgcacct tctggatcga gcgggccgcc    900
ggcggcgacg cccggctgcg tttcggcacc ggcgccggca tcacctgggg ctccgacccg    960
gagggcgagt ggcgggagac cgaactgaag gccgcacggc tgctcgcggt agcgtcgggg   1020
gcgtacgagg tgaacgcgac gggagaggtg ctggcgacgt ga                      1062
```

<210> SEQ ID NO 142
<211> LENGTH: 1365
<212> TYPE: DNA
<213> ORGANISM: Salmonella enterica

<400> SEQUENCE: 142

```
atgatgaaga cgttatctcc cactgttatc accttaccct ggcgtccgga cgccgctgaa     60
cactattttg cgcccgtaaa ccatttgccc tgggcgatgc tgctgcattc aggtgatgct    120
attcatccct ataaccgttt tgatattctg gtcgccgatc ctgtcaccac actgaccacg    180
cgcgcccagg aaaccacggt atgtactgcg cgcacgacta ccgtcactct cgacgatccg    240
ttacacgttt tgcagactca actggaggcg ctgccttttc atcctcagcc tgaccctgac    300
ttaccctttc agggcggcgc gctgggtctg tttggttatg atttagggcg gcgtttcgaa    360
attctgcccg atactgccgc gcgcgatatc gctttacccg atatggcgat tggcctttac    420
gactgggcgc tgattgtcga tcaccataaa caggtagtgt cgctgataag ctatcacgat    480
gcagacgccc gatatcgctg gctcaccggc cagcgcgcgc cgacccgaac gcccttcagg    540
cttacctcgg cctggcaatc caatatgacg cgttgcgagt atggcgagaa gtttcgtcag    600
gtgcaggcct ggctgcacag cggggactgc tatcaggtca atctttccca gcgttttcag    660
gcgagctacg agggtgatga atggcaggct ttcgaacgcc ttaaccgcgc aaatcgcgcc    720
ccgttcagcg cctttcttcg tttacatgac ggcgccatat tgagcctttc tcccgagcgt    780
tttatccaac tggagaacgg tcatattcag acgcgcccga tcaaaggtac gcttccacgg    840
cttaacgatc cgcaggcgga tcgtcagcag gcgcagaaac tggctaattc aatgaaagat    900
cgcgctgaaa atttgatgat tgtcgatttg atgcgtaacg acattggccg ggtcgccgta    960
ccaggttcgg tgaaagtgcc ggaactgttc gtcgtcgaac catttcctgc cgttcaccat   1020
ctggttagca ccattactgc ccgtttacca gactcgcttc atgccaccga tctgctgcgc   1080
```

gcggctttcc ccggcggctc cattaccggc gcgcctaaag tgcgggcaat ggaaattatc 1140
gacgaactgg agccgcagcg acgcaacgcc tggtgcggta gcatcggtta tctgagtttc 1200
tgcggcaaga tggataccag tattactatc cgcaccgtca cggcaacgca gggccaactc 1260
tattgctcag ccggcggcgg tatcgtggcc gatagcaacg aagaagcgga atatcaggaa 1320
acttttgata aagttaatcg tatcctgcac ccactggaga actaa 1365

<210> SEQ ID NO 143
<211> LENGTH: 1365
<212> TYPE: DNA
<213> ORGANISM: Salmonella bongori

<400> SEQUENCE: 143
atgatgaaga cgttatctcc cactgttatc accttaccct ggcgtcagga cgccgctgaa 60
cactattttg cgcccataag ccagttgccc tgggcgatgt tgctgcattc cggtaatgcc 120
cttcatccgt ataatcgctt tgatattctg gttgccgatc ccatcaccac cctgatcacg 180
cgggcaaaag acaccacggt acgcacagct cacagcacca ccgtcagcct caacgatccg 240
ttacagattt tacagtcaca gctggaggcg ctgtcttttc atcctctgcc tgatcctgac 300
ctaccgttcc agggcggcgc gctgggtctg tttggttacg atctgggccg acatttcgaa 360
gatctgcccg ctctcgccgc gcaggacatc gctttacccg atatggcgat cggcatttac 420
gactgggcgc tcattgtcga tcaccaaaaa caggccgtgt cactgataag ctatcacgat 480
gcagacgccc gttatcgctg gctcattagc cagcgtgcgc cgacccgggc gccctttacg 540
ctgacctcgg cctggcaatc caatatgacg cgccgcgagt atggtgaaaa gtttcgccag 600
gtgcaggcct ggctgcacag cggcgactgt taccaggtca atcttgccca gcgttttcag 660
gcaagttatg agggtgatga gtggcaagct ttcgaacgcc ttaaccgcgc aaatcgcgcg 720
ccgtttagcg cctttcttcg tctccgtgac ggcgccatat taagcctttc tcctgagcgt 780
tttatccagt tggagaacgg tcacatccag acacgtccaa ttaaaggtac gcttccacgg 840
cgccatgagc tgcaggcgga tcgcctgcaa gcacaaaaat tggcaaactc gccgaaagat 900
cgcgccgaaa atctgatgat cgtcgatctg atgcgtaacg acattggtcg ggtcgccgtt 960
ccggggtcgg tgagagtccc ggagctgttt gtcgtcgaac cgtttcccgc cgttcaccat 1020
ctggtcagca ccattaccgc tcgcttaccg gactcgcttc atgctacaga cctgctgcgt 1080
gccgcctttc ccggcggttc catcactggc gcgcctaaag tgcgagcgat ggaaattatc 1140
gatgaactgg agccgcagcg acgcaacgcc tggtgcggca gcattggcta tctgagtttc 1200
tgcggcaaca tggataccag tattaccatt cgaacactca ccgcgacaca gggccaactc 1260
tattgctctg ccggcggcgg tatcgtggcg gatagcacgg aagaagcgga atatcaggaa 1320
acctttgata aagttaatcg tatcctgcat caactggaga attaa 1365

<210> SEQ ID NO 144
<211> LENGTH: 1362
<212> TYPE: DNA
<213> ORGANISM: Pseudomonas aeruginosa

<400> SEQUENCE: 144
atgcccagtt gtcatgttca ccccctgccc taccatagcg acccaagctg tctctttgcc 60
atcatccatg aggcgcccgg tgcggtgatg ctcgattcgg gtcgccccat cgctacccgt 120
ggacgctatg accttatgag cgcctggcca ttggcagaac tggcgccgct gcccgacgaa 180

-continued

```
tcggccaacc gcttcttcgc ccgcctacgc gaagcggccg gaagcctggg ccccgcgcag    240
ctgccagcgc cgtacgaact gcccttcgcc ggcggtctgc tgggctattt atcctacgac    300
ctgggtcggc gcatcgagcg catcggcgaa cacgcccgcg atgacctggg cctgccgctg    360
gcctccgtcg gcctgtatgc ctgggcgctg atcagcgacc accaggccgg caccagccaa    420
ctggtattcc acccgcgatt ggacgagcgc gaacgccagc gcctgatcgc cctgttcagc    480
gaggaagcgc aaggcacggc cggcaacttc aagcttctgg gaaaattccg acggagcatc    540
agcgcatccg actatcggca ggcgatccgc cgcatccagg actacatcca ggcaggcgac    600
tgctaccagg tgaactatag ccagcgcttc caggccgctt gcagcggctc gccgtggccg    660
gcctatcgcg ccctgcgcga ggcctgcccg acgccgttct ccggctacct gcgactggcc    720
gacggcgcga tcctcagcct gtcgccggag cgcttcctca agctcggcaa gggcaaggtg    780
gaaacccggc cgatcaaggg cacccgcccg cgcggcaaga cccccgagga ggacatggcg    840
ctggcggcgt cgctgctggc cagccccaag gaccgcgcgg aaaacctgat gatcgtcgac    900
ctgctgcgca acgacatcgg acgcagttgc caacctggca gcgtacgggt accggagctg    960
tttgccctgg aaagctatcc caacgtgcat cacctggtga gcagcgtcac cggcgaactg   1020
gcgccgggca aggacgccct cgacctgctg gaaggcagct tccccggcgg ctcgatcacc   1080
ggcgcgccga agattcgcgc catgcagatc atcgacgagc tggaaccgag ccgacgcggc   1140
atctactgcg gcagcctgtt ctacctcgac gtgcgcggcg agatggacag ctcgatcgcc   1200
atccgcaccc tgctggtcag ggacggccag gtcagttgct ggggcggcgg cggcatcgtc   1260
gccgactcgc actgggagga cgagtaccag gaaaccctgg acaaggtccg ggtgctgctg   1320
gaaaccctgg aaggaatggc cgggacagcg tccccggaat ag                       1362
```

<210> SEQ ID NO 145
<211> LENGTH: 1341
<212> TYPE: DNA
<213> ORGANISM: Pseudomonas putida

<400> SEQUENCE: 145

```
atgccgacct gcacgctaca ccccctgccc taccagcccg accctgccgc ctatttcgcc     60
cacctgcgcc aggcccccgg tgcgatcctg ctcgacagcg ctcgccccgg cgccgaacgc    120
gggcgtttcg acctgctcag cgcctggccg ctgcaacaac tgcaggcgca gcccgatgaa    180
gatggccgcg tcttcctcca gcgcctgcgc gctggcctgg cacaactggg ccacgccgac    240
ttgcccaacg gtgtagagct gcccttcgcc gggggcctga tcggctacct gagctacgac    300
ttcggccgcc gcctggaaca cctgccaagc ctggccgtgg acgacctggg cctgccagac    360
gcacaactgg gcctgtatgc ctgggcactg gtcagcgatc acttgctcgg caccagccag    420
ctggtgttcc accctagcct ggccggcgac gagcgcgaac gcctgatcag cctgttccag    480
gacaccagcg ccaccaccgg cgacttccgg ctgctcgcgc cgatggccgg tgacctggag    540
ccggagcaat acaaaaccgc tttcgaccag gtacaacgct acatccaggc cggtgactgc    600
taccagatca acctcaccca acgctttcgc gcaccctgcc aaggcgatcc atggcgggcc    660
taccaggccc tgcgccaggc ctgcccgacc cccttctccg gctaccagca actggccgac    720
ggcagtaccc tgctgagctt ttcgcccgag cgcttcatcc gcgtcagcca gggccaggtg    780
gaaacccggc cgatcaaggg cacccgccca cgcgccagtg acccggcgca agaccagcgt    840
aatgcccagg agctgctgca cagcccgaag gaccgctcgg aaaacctgat gatcgtcgac    900
ctgctgcgca acgacctggg gcgcacgtgc gagattggct cagtgaaggt accggaactg    960
```

ttcagcctgg agagttaccc caacgtgcac catctggtca gcagcatcac cggccagctg 1020
gccagcgaca aggatgcgct ggacctgatc ggcgacagct tccctggcgg ctcgatcacc 1080
ggcgcaccga agatccgcgc catgcagatc atcgacgaac tggagcccgc gcgccgcgcg 1140
ctgtactgcg gctcgctgct gtatgtggat gtgcgcggcg aaatggacag ttcgatcgcc 1200
attcgcagct tgctgatcaa agatggccag gtcagttgct ggggcggcgg cgcggtggta 1260
gccgactcgc agtggcaggc cgagtatgaa gagtcgatcg ccaaagtgcg ggtgctgatg 1320
cagaccctgc agggcttgtg a 1341

<210> SEQ ID NO 146
<211> LENGTH: 1344
<212> TYPE: DNA
<213> ORGANISM: Pseudomonas fluorescens

<400> SEQUENCE: 146
atgttgacct gttccgtaca cccgctgccc taccgcgcca accccgccga ctattttgcg 60
gccgtccgcc atgcgcccgg cgccgtgctg ctcgacagtg gccggccgag tgccgatcgt 120
ggccgttatg acttgctcag cgcctggccg ctggaacaac tggcggtgtt gccggacgag 180
cgcggagaag atttcctgca acgcctacgg accaatctga cccggttggg cgacgcgcaa 240
ttgcccgacg actacgaatt gcctttcgct ggtggcctga ttggttacct gagctacgac 300
ttcggccgtc atctggaaaa cctgccgagt caggccctgg atgacctgca attgcccgat 360
gcgcgatttg gtctgtacga ctgggccttg atcagcgatc accaatcggc caccagccaa 420
cttgtgttcc acccctcagt cagcgccagc gagaaacagc ggttgatcga tgtattcagc 480
caaccggtgg gcacggaact gaccccattc aaactgaaca gcccgatggc agccgatctc 540
tcggccaatg aataccgtca ggcgttcgaa cgtatccagc attacattca ggccggcgac 600
tgctatcagg tcaatttcgc ccagcgtttc cgcgcgccgt gccagggcga tccatggctg 660
gcctactgca aattgcgcga ggcctgcccg acaccgtttt ccgggttcca gagcctgccc 720
gacggcaacg cagtgctgag cgtgtcgccc gagcgtttcg tcaaagtcag ccagcgtcag 780
gtggaaaccc gcccgatcaa gggcacccgt ccccgtggcg cgaacccgac cgaggacgcg 840
gcgaacgccg ccgaattgct ggccagcccc aaggatcgcg cggaaaacct gatgatcgtc 900
gacctgctgc gcaatgatct gggccgcacc tgccgtatcg gctcggtgcg agtgccagag 960
ctgttcagcc tggaaagcta tccgaacgtg catcacctgg tcagcagcgt gaccggcgaa 1020
ctggcgcagg atcgcgacgc cctggacctg attgccggca gcttccccgg cggctcgatc 1080
accggcgcac cgaaaatccg tgcgatgcag atcatcgatg agctggagcc gacccggcgt 1140
ggtttgtatt gcggttcgtt gctgtatctg gacgtgcgcg gcgagatgga cagctccatc 1200
gccattcgca gtctgctggt gaaggatgga caagtgtgtt gctggggcgg tggcggaatc 1260
gtcgccgatt ctgactggga agcggagtat caggaatcga tcaccaaggt cagagtcctg 1320
ctcgaaaccc tgcagaacct ctga 1344

<210> SEQ ID NO 147
<211> LENGTH: 1377
<212> TYPE: DNA
<213> ORGANISM: Yersinia pestis

<400> SEQUENCE: 147
atgtgtgaga aatttttaac cgtcaaagag ttaccttatc accctgatgc cctgcttcaa 60

-continued

```
caattcaccc cacttgccaa ccaagcttgg gcgatgttgt tgcactcagg atttgctcaa    120
cacccccata gtcgctttga tatcttggtc gctgatccaa aaataacgct gacaactcat    180
ggggataaaa cggttattgt cagtgatcag gggcaggaaa cctccctcgc ggatcccttc    240
tctttgctgc agcagcaact ggataaattc gccccagcga tgcctgctca ccctgatctg    300
ccgtttcagg gcggagcgtt agggctattt ggttacgact taggccgccg agttgaaaaa    360
ttgcctgaac tggcggcgca cgatatcgcc ttgccggata tggccattgg cctgtatgac    420
tgggcgctca ttgctgacca ctctcggcag aagctcacgc tggtatccct tggcgatgcc    480
gaacagcgct tgcattggct gcatcagcaa acaaccgatg agaacctcgt cccccttcaaa    540
ctcacggttc catggcaggc agatatgtca cgggagcagt acggcgaaaa attccgccaa    600
attcaagcgt atctgcgtag cggtgactgt taccaaatca atctggcaca aagattcagc    660
gcagagtatc agggggatga atggcaagca tttctgtcac tgagtcgtag caatcaagcc    720
ccctttttcag cttttattcg cttacccgac aacgccatat tgagtgtttc accagaacgt    780
ttcttgtggt tggagaatca tcaggttcaa acccggccga ttaaaggtac gctaccccgt    840
ttggccgatc ctgagcagga tcgccagcaa gctgagcgat tggcgaattc agccaaagat    900
caggctgaaa atctcatgat tgtggactta ctgcgtaacg atattggccg tgtcgcacgt    960
ccgggtagcg tccgcgtacc agagctgttt gtggtggagc cttttcctgc ggtgcaccac   1020
ttagtcagta caattaccgc aatacttccc ccagaatgtt cgccgaccga attactgcgc   1080
gcctgtttcc ccggcgggtc aattactggt gcccccaagg tccgagcaat ggaaattatt   1140
gaacaactcg aaccctatcg acgcaatgct tattgcggta acattggcta cataagttgc   1200
tgcggcacca tggataccaa tattactatc cgtaccctga tgacagagaa cggtaagata   1260
tattgttctg ccggaggggg gattgtcgcc gacagccaag agcaagctga atatcaagaa   1320
acgttcgata aggtcgcccg tattttaccg caactggggg agtgtgttat ttcgtga      1377
```

<210> SEQ ID NO 148
<211> LENGTH: 1377
<212> TYPE: DNA
<213> ORGANISM: Yersinia pseudotuberculosis

<400> SEQUENCE: 148

```
atgtgtgaga aatttttaac cgtcaaagag ttaccttatc accctgatgc cctgcttcaa     60
caattcaccc cacttgccaa ccaagcttgg gcgatgttgt tgcactcagg atttgctcaa    120
cacccccata gtcgctttga tatcttggtc gctgatccaa aaataacgct gacaactcat    180
ggggataaaa cggttattgt cagtgatcag gggcaggaaa cctccctcgc ggatcccttc    240
tctttgctgc agcagcaact ggataaattc gccccagcga tgcctgctca ccctgatctg    300
ccgtttcagg gcggagcgtt agggctattt ggttacgact taggccgccg agttgaaaaa    360
ttgcctgaac tggcggcgca cgatatcgcc ttgccggata tggccattgg cctgtatgac    420
tgggcgctca ttgctgacca ctctcggcag aagctcacgc tggtatccct tggcgatgcc    480
gaacagcgct tgcattggct gcatcagcaa acaaccgatg agaacctcgt cccccttcaaa    540
ctcacggttc catggcaggc agatatgtca cgggagcagt acggcgaaaa attccgccaa    600
attcaagcgt atctgcgtag cggtgactgt taccaaatca atctggcaca aagattcagc    660
gcagagtatc agggggatga atggcaagca tttctgtcac tgagtcgtag caatcaagcc    720
ccctttttcag cttttattcg cttacccgac aacgccatat tgagtgtttc accagaacgt    780
ttcttgtggt tggagaatca tcaggttcaa acccggccga ttaaaggtac gctaccccgt    840
```

ttggccgatc ctgagcagga tcgccagcaa gctgagcgat tggcgaattc agccaaagat 900
caggctgaaa atctcatgat tgtggacttg ctgcgtaacg atattggccg tgtcgcacgt 960
ccgggtagcg tccgcgtacc agagctgttt gtggtggagc cttttcctgc ggtgcaccac 1020
ttagtcagta caattaccgc aatacttccc ccaaaatgtt cgccgaccga attactgcgc 1080
gcctgtttcc ccggcgggtc aattactggt gcccccaagg tccgagcaat ggaaattatt 1140
gaacaactcg aaccctatcg acgcaatgct tattgcggta acattggcta cataagttgc 1200
tgcggcacca tggataccaa tattactatc cgtaccctga tgacagagaa cggtaagata 1260
tattgttctg ccggaggggg gattgtcgcc gacagccaag agcaagctga atatcaagaa 1320
acgttcgata aggtcgcccg tattttaccg caactggggg agtgtgttat ttcgtga 1377

<210> SEQ ID NO 149
<211> LENGTH: 1368
<212> TYPE: DNA
<213> ORGANISM: Enterobacter sp.

<400> SEQUENCE: 149
atgccacaca tgaagacatt accccccact gtcattacat tgccgtggcg ccatgacgcc 60
gccgaattct ggtttacgcg cttaagccct ctcccctggg caatgctgct gcattccggg 120
tacgcggatc atccttatag ccgctttgat attctggtgg ctgacccact gacgacactg 180
gtcaccgagg gtgatatcac gcgcattacc tctgcgcgct ctcgtttttc tcatgaagat 240
ccgctgacgt tacttgaaca cgagatccac gcgctggcac tgcctacgga ttcccatcct 300
gacctgcctt ttcagggcgg ggcgctgggc ctttttggtt acgatttggg tcgtcggttc 360
gaaacgctgc ctaatatggc gcagaatgat attttgctgc cggatatggc ggtggggttg 420
tatgactggg caatcattgt cgatcaccac aaaaaagtgg tttcgcttct cagccattcg 480
gacgtaaatg cccgactggc atggcttgac gcacaacccg tgcccgagac ggctgagttt 540
tcgctaacgt ctgcgtggcg ctcaaatatg agcgccgagg actatgctga aaagttcggg 600
caggttcagg cgtatttaca cagcggtgac tgctatcagg taaatctcgc ccaacgattc 660
caggccacgt atcgcggtga tgaatggcag gcgtttaagc atttaaacgc gaacaatcgt 720
gcgccgttca gcgcgtttct gcgcctggaa cagggcgcaa tcctgagtca gtcgccagag 780
cgttttatac atctggctga tggagccatt cagacgcgcc cgattaaggg cacgcttccg 840
cgtctgccag accccgaagc cgatcgcgag caggccgaaa aattggccgc atccccgaaa 900
gatcgtgccg agaatctgat gattgtcgat ttaatgcgta acgatattgg gcgtgttgcg 960
gtgccgggga gcgtacgcgt cccggaactg tttgtcgtgg agccgttccc ggcggttcat 1020
catctggtca gcaccattac agcccagctt cctgccagcc gttccgcctg cgatctgctg 1080
cgcgcggcgt ttcctggcgg atcaatcacc ggtgccccaa aagtccgtgc gatgcaaatt 1140
atcgacgaac tggagccgca tcgtcgtaac gcctggtgcg gaagcattgg ttatgtgagc 1200
gtgtgcggca ccatggacac cagcattacc attcgtaccc tgacggcctg cgacggacaa 1260
ctctattgtt ccgcaggggg cggcatcgtg gccgacagtc aggtcgatgc tgaatatcag 1320
gaaacgtttg ataaagtaaa ccgcatcctg caacaactgg agagctaa 1368

<210> SEQ ID NO 150
<211> LENGTH: 1329
<212> TYPE: DNA
<213> ORGANISM: Enterobacter cloacae

<400> SEQUENCE: 150
atgaacatgc gcttccccac tgttattacc ctgccgtggc gtactgacgc cgctgaattc 60
tggtttgctc gtctgagcca tcttccctgg gcgatgctgc tgcattccgg ccatgcggac 120
catccttaca gccgcttcga cattgtggtt gctgacccgg tgcgcacggt gacatccgaa 180
aaccagccct ccacgcacga tccgctgatc aagcttcagg aggctatcga cgagctgggt 240
ttgtctgcca cgccgaaccc ggatcttccc ttccagggcg gtgcgctggg cgtgtttggc 300
tatgaccttg gtcgccgctt tgaaacgctg ccttccgttg cgaaggcgga tattccgctg 360
ccggatatgg cggtgggact ttacgactgg gcgctgattg tcgatcacca taaacaggtg 420
gtctccctgc tcagccattc ggatgtggag gcacgcctgg cctggctgaa cgcgcagcag 480
ccagcagccg cgccggattt ccgtctgacc tctgcgtggc gttcaaacat gaccccgcag 540
acctatgcgg aaaaattcgc acgcgtgcag gcatatctgc aaagcggcga ttgttatcag 600
gtgaaccttg cccagcgctt ccaggcaacg tatcagggcg atgaatggca ggcctttacc 660
cgcctcaatg ccagcaaccg ggcacctttc agtgcgttta tccgtctcga tcagggcgcg 720
atcctgagtc tttcgcctga gcggtttatt catctggcgg aaggcaagat ccagacacgc 780
ccgattaaag ggaccttgcc gcgcctgagc gatccggctg ccgaccgcca gcaggcggaa 840
aagctcgccg tgtcaccgaa ggaccgcgcc gaaaatttaa tgattgtcga cctgatgcgc 900
aacgacattg gccgggtggc ggtaccgggc agcgttcgcg tgccggagct gttcgtcgtc 960
gagcctttcc cggcggtgca ccatctggtc agcaccatta ctgcacagct gccggcttcg 1020 cgtacccccct gcgatcttct gcgcgccgcg ttcccgggtg gctccatcac cggcgcgcca 1080
aaagtgcggg cgatggagat tatcgatgag ctggaaccgc accgtcgaaa cgcctggtgc 1140
ggcagcattg gctacgttag cgtctgcggc acgctggata ccagcatcac tattcgcacc 1200
ctgacggcct gcgacggcca gctttactgt tccgcaggcg gcgggattgt tgctgacagc 1260
caggtcgagg cggaatatca ggaaaccttt gataaagtta accgtatcct gcaacaactg 1320
gagaactga 1329

<210> SEQ ID NO 151
<211> LENGTH: 1254
<212> TYPE: DNA
<213> ORGANISM: Mycobacterium smegmatis

<400> SEQUENCE: 151
atgcggatcg agcggttctg cacgccggac ggccaggctg acgccccttc cgtgctgcgc 60
agcgtcgccg cggccgcgtc ggccgccggt ctggcaccgc ctgccgcgct gatcggtgac 120
tggttcggct cgcgtgccgt catcgcgccg accgtcaccg cgctgcccgc cgaacccgac 180
gcggtgttcg atgtgcctca gggttcggcc gaaggtgccg ccgtgggtgg tggctggttc 240
ggctacctgt cgtatcccga tccaggggcc tgcgagagcg caccacgcat ccctgtggcc 300
gcaggcgggt ggtcggactg cgtcctgcgg caggacaccg aagggcagtg gtggtacgaa 360
agtctcgccg gcgcaccgct tcccgcatgg ctgcgtgacc tggcgcccac accttcccgc 420
ccgcacaccg tcgactgggt gccgccggat cgtggcgcgc accgccgtgg cgtgctggcc 480
tgcctggagg ccatcgcggc gggcgaggtg tatcaggcat gcgtatgcac ccggttcacc 540
gggcgcctgg acggctcgcc gtcggacttc ttcgccgacg cggtggcgcg caccgcacct 600
gcgcgcgcgg cgtacgtggc cggcgactgg ggtgccgtcg cgtcgctgtc accggaactg 660
ttcctgagcc ggcgaggatc gtcggtgtcg tcgagcccca tcaaggggac gctgccgcgc 720

-continued cacgccgacc ccgccggact gcgggcatcg gtcaaggacg tcgccgagaa cgtcatgatc 780
gtcgacctgg tgcgcaacga tctcggtcgc gtcgcgcgga ccgggtcggt gacggtgccc 840
gaactcctcg cggtcaagcc cgcaccgggc gtgtggcatc tggtgtcgac cgtggcggcc 900
gaggtcgagc agtgcgtgcc catgggcgcg ctgctcgatg ccgctttccc gcccgcgtcg 960
gtcaccggca cgccgaaagg ccgcgcgcgt gagctgctgc gcgcctggga gcctggtttg 1020
cgtggaatat actgcgggac agtcggtctg gcctcacccg tcgcgggctg cgagttgaac 1080
gtcgcgatcc gcaccgtcga gttcggcgcc gacggatcgg ctgtgctcgg cgtgggcggc 1140
ggtatcaccg cggactccga ccccgaccgc gagtgggagg aatgtctgca caaggccgcc 1200
agcatcgtgg ggccggtgac cgatcagtcc cttgagcgca gcacggcgtc gtag 1254

<210> SEQ ID NO 152
<211> LENGTH: 1356
<212> TYPE: DNA
<213> ORGANISM: Klebsiella pneumoniae

<400> SEQUENCE: 152
atgttgtccc ccgcgattat taccctgccc tggcgcccgg atgcggccga acactatttt 60
gcgccgttaa gcgccctgcc ctgggcgatg ctgctgcatt ccggctttgc cgaccatccg 120
cataaccgct ttgatattct ggtggctgcc ccgcgcgcca cgctgctgac gcgcggtgaa 180
cagacgtggg tcgacgacgg cgaaaccgtt gttgtctcag cggaagatcc gctgcagctc 240
ctgcagcagc agttggatcg tcagccgttc acgccgcaac cccatgacga tctgccgttt 300
ctcggcggcg cgctgggatt attcggttac gacctgggcc gtcgctttga gcgtctccct 360
tcgcacgcgc aggccgatat cgcgctggcg gatatggcgg tggggatcta tgactgggcg 420
cttatcgtcg accaccagcg ccaacagata tcgctgctca gctatgacga cccgcagcag 480
cgtctacagt ggctggaggc gcaaacgccg acgccgggtg aaaccttcgc cctgacctct 540
gcctggcagt caaatatgag ccgccagcag tacggggaaa aatttcgcca ggtacaggcc 600
tatctgcaca gcggcgactg ctatcaggtc aacctcgccc agcgttttca ggccagctac 660
gtcggtgatg aatggcaggc cttccgccag ctgaacgccg tcaaccgcgc cccctttagc 720
gcctttattc gcctcgatga aggggcgatt tttagcctgt cgccggagcg ctttatccag 780
ctgcgccagg gggagatcca gacgcggccg ataaaaggca ccctgccgcg gctcgattcg 840
ccgctggcag atgcgcagca ggctgagaag ctggcgaatt cgccgaaaga tcgcgccgag 900
aatttaatga ttgtcgacct gatgcgcaac gacatcggcc gcgtcgccgt cccgggcagc 960
gtgcgggtcc ccgagctgtt cgtggtggag ccattcccgg cggtccatca tctggtcagc 1020
accatcaccg cccgcctgcc aatgacgctg cacgccagcg acctgctgcg cgccgccttt 1080
cccggcggct cgatcaccgg cgcgccgaaa gtgcgggcga tggagattat cgatgaactg 1140
gagccccaac gacgcaacgc ctggtgtggg agcattggct acctgagcta ttgcggcaat 1200
atggatacca gcatcaccat tcgcaccctg acggcatggc agggacagct gtactgctcc 1260
gccggcggcg gaattgtggc ggatagcgag gaagcggcgg aatatcagga aacttttgat 1320
aaagttaatc gtatcctgca gcaactggag aactag 1356

<210> SEQ ID NO 153
<211> LENGTH: 1371
<212> TYPE: DNA
<213> ORGANISM: Xenorhabdus bovienii -continued

<400> SEQUENCE: 153
atgaagattg cattacaaaa acgactttta ccttattctc ctgatcttgc cacccgatat 60
tttgctcctc tctcagtatc accttgggca atgttgttac attctggaac ggctgaacat 120
ccccataacc gatttgatat tttagttgcc gaaccagtaa caacgcttat cacacgggac 180
gaatcaacag aaataaactg taatggtgac gtttcgctct ctcaggaaga tccattcttg 240
ttgttgaaaa agcatctgca tattcgcaat attgctccgc aattcgatcc tgattaccct 300
tttcaggggg gtgcattagg tctatgggga tacgatcttg gccgcaagat tgaaaaatta 360
cctgccattg ctgccaatga actggatttt ccggatatgg ccgttgggat ttacgactgg 420
gctctgatca tcgatcatca ccaacagaaa gcaacattac tgggttatca caatctcgat 480
aatcgtctgg catggctaga atcgcagaaa aaaaaccggg aaacaaattt ctccctgagc 540
agtcaatggc aatctaatat gactgctcag caataccacg aaaaaatcgc ccagattcat 600
cgctatctgc gtgatggaga ctgctatcaa gtcaatctgt cgcagcgctt tcatgccagc 660
tatcagggtg atgaatggca ggccttcacc caactcaatg atagtaaccg cgctcccttt 720
tctgctttta tccgtttgcc tgaaaactgc attatcagcg tttcgcctga acgtttttta 780
ttactggaag ataagaaaat ccagacgcgt ccaattaagg gaacattacc acgattgcaa 840
gatccggaag aagatcattt acaagccaaa aaattggcta actcccgtaa agatcgcgct 900
gaaaatctga tgattgttga cttattgaga aatgacatcg gacgggttgc aacgccaggc 960
tcagtcaaag ttcctgaatt gtttgtcgtt gaaccctttc ccgctgtgca tcatctggtc 1020
agtaccatta cagcgacatt acctgatgaa tatcatgcca ccgatttact ccgagcctgt 1080
tttccaggtg gttcaatcac tggcgcaccc aaaattcgtg ctatggaaat cattgaagaa 1140
ttagaacctc atcgtcggca tggatattgc ggtgccattg gctacattag tttctgcggt 1200
acaatggaca gcaatatcac catacgtacc ttactgacag aaaagggaaa aatttactgt 1260
tgggctggag gtggtatcgt cgcagatagc attgctgaaa aagaatatca ggaaacattt 1320
gataaactgg ggcgcatttt acctcaatta ggagaactcc atataccatg a 1371

<210> SEQ ID NO 154
<211> LENGTH: 1368
<212> TYPE: DNA
<213> ORGANISM: Pantoea ananatis

<400> SEQUENCE: 154
ttgtgctcaa tgaacgttca aactcataac ctacgttatt ctcctgacgc ccttacgcac 60
tatttttccc gtattgcgca tctgccatgg gcgatgctgc tgtcgtcagg gcacgccgat 120
cacagcgata accgttttga tatcctgacc gccgatcccc ttaccacact gacgacgcgt 180
ggcaggataa cagaaattcg ccatgcacat ggccatgaaa acagtgagga cgatcctctc 240
tctctcgtgc agcactactg caacgcgttg ggcatccccc caacacgcca tccggattta 300
ccctttgtgg gcggcgcgct ggggctgttt ggctatgacc tggggcggcg ctttgagcag 360
ttacctcaga tcgccaccgc cgatctgcag acgccggata tggcggtggg catctacaac 420
tgggcattaa ttgccgatca tcatcgtcag acattgaccc tggttgctgt agaggatgtt 480
gcgcagcggc tcagttggct ggaaggctgg cccacacgcg aaagcgcgcc gttttcactg 540
accagcgaat ggtccgctaa cctcagcgtt gatgactacg cggaacgttt tcgcaaggtc 600
caggcctata tccaggcggg tgactgctac caggtcaacc tgtcacagcg cttcaaggcc 660
ggttatcagg gtgacgaatg gcgtgcgttc tgcttgctta atcaggctaa tcgcgcgcct 720
ttcagcgctt ttttacgcct gccggagagc gccattctca gcctttcccc cgagcgcttt 780
atggcgctgg atcaacacgt cattacgacc cgcccgatta aaggtacgcg cccgcgtgac 840
agcgatccgc tgcgggacgc cgcccaggcc aaaagtctgc ggacgtccgc caaagaccgg 900
gcagagaatc tgatgattgt cgatctgctg cgtaatgata taggccgggt cgccgtggcc 960
ggttccgtaa gcgtacccga actgtttgtg gtggaaccct ttccggcagt gcatcatctg 1020
gtcagcaccg ttcgcgccac gctgcccgaa aatctgcagg cctgcgatct gttacgcgcc 1080
tgctttcccg gcggttcgat cacgggtgcg ccgaaaattc gtgcaatgga aattatcgat 1140
gaactggaac cgcaacgccg taacgcctgg tgtggcagca tcggatatct gagtgtgtgt 1200
ggtcgtatgg acaccagtat tacgattcgt acgttgattg ccgaagatca tcacctctac 1260
tgttcggctg gcggcggttt agtggccgac agcgagctgg aatcggaata tcaggaaacc 1320
ctggataagg tcagccgcat tttgcccgcg ctggaaaaag gggcctga 1368

<210> SEQ ID NO 155
<211> LENGTH: 1377
<212> TYPE: DNA
<213> ORGANISM: Providencia stuartii

<400> SEQUENCE: 155
atggttatca ataaaataca actcccctat tatcctgatg ttgctattga ctattttacg 60
ccactagccc atcaaccttg gtcaatgctg ctccattcag gcaatgccga gcattcgcat 120
aacagatacg atattgttgt ggctgatcct attgcaacgc taaccactat tggcgataaa 180
acgacgatca cccacccgca ttcggttgag agttcagacg cagacccatt taacctcctt 240
caacaaacta ttgaacacta cgcccctgac catgctagtg atgatacgct tcctttcact 300
ggcggtgctc tcggtatttg gagctacgat ttaggtcgtc gtatcgaaaa aatgccacac 360
atagcgacta cggatttatc gtttccagat atggccgttg ggatatatca atgggcgttg 420
attgtcgata atcaagaaaa aacggtcacc ttattcagtt attctgatac caataaacgc 480
cttgattggt tgaagaaaca aaaagcttca cgtaaaacca agttcgccct taccagttca 540
tggcattcaa atatgtcaca agagcagtat cacgagaaaa tcggccaaat acatgaatac 600
ttgcgtagcg gtgattgcta tcaaataaat ctagcgcagc gttttcaagc aaaatataag 660
ggtaatgaat gggatgcatt tttattatta acccgagcaa atcgcgcccc tttctcttct 720
ttcattcgtc ttcctaataa tgcggtgatc agcatctcgc ctgaacgctt tatccagtta 780
caagatggtg agatacaaac acgtccaatc aaaggcacac tacctcgttt agaggatgaa 840
cacgccgatg ccatgcaagt cgaaaagttg gcgaattccc ctaaagatcg tgctgaaaac 900
ttgatgattg tcgatttact ccgtaatgat attggtcgag ttgcacaacc aggaacagtc 960
aaggtccctg aattattcgc tgtcgaagcc ttccctgcgg tttatcactt agttagcaca 1020
attactgcaa cacttgataa accctatacg gcaacagatc ttctgcgtgc aagtttccca 1080
ggaggctcaa ttactggtgc ccctaaaatt cgggcgatgc aaatcattga agagcttgaa 1140
cctcatcgtc gtcatggcta ttgtggcgct ataggctata ttagtttttg tggcaaaatg 1200
gataccaaca ttaccatccg tacactgtta acagataaaa aacggatttt ttgctgggct 1260
ggcggtggta ttgtggcaga tagccaagcg gataaagagt atcaagaaac ctttgataag 1320
ttacggctga tattacccgt gttaggagaa gtagagcacg atgaccaaac tgaatga 1377

<210> SEQ ID NO 156

<211> LENGTH: 1332
<212> TYPE: DNA
<213> ORGANISM: Azotobacter vinelandii

<400> SEQUENCE: 156
atgcccagtt gccgtatcca cacactcccc tatagcgccg atccgacccg ctatttcgag 60
aagatccgcc aggcacccgg cgccgtactg ttcgacagtg gccgaccggc atcgcgacgg 120
ggccgttacg acctgctcag cgcctggccg cgggcccgcc tcgttccttc tgccggtgaa 180
accggcagcg gttttctcca acgactgcgc caggccgcat cgagtctggg acatatcgag 240
acacctggac ttcctttcgc gggcggcctg atgggctacc tgtcctacga tttcgcccgt 300
cgtctcgaac gcctgcctga tacgacccac gatgacctgg agcttcccga tgcccagctc 360
ggactgtatg cctgggcagt gatcacggac caccaggcgc agaccaccac gctggtctgc 420
caccccagcc tggacggccg cgaatgcgag cgtttgagac gcctgttccg cacgccgccg 480
ccccgaagca cggcattcca tctcgcggcg gatttcaccc cggacctgac cgtcagcgac 540
tatcgcgcag ccatcgagcg cattctcgcc tacattcagg caggcgactg ttaccaggtg 600
aacttcgccc agcgtttcca ggccccccttc cagggcgatc cctgggttgc ctaccaggct 660
ttgcgccagg tctgtccgac cccctcgcc ggataccagt ccctggatgg cggcggcgcc 720
attctcagcc tttcgccgga acgctttctg agcgtcacgg atggacaggt ggaaacccgt 780
ccgatcaagg gcacccgccc acgcggtcgc agtgccgcgg aagaccgact gtacgccgac 840
gagctgcggc tcagcgccaa ggatcgagcc gagaacctga tgatcgtcga cctgctgcgc 900
aacgacctga gccgcagttg ccggcccggc tcggtgcacg ttccgcaact gttcgccctg 960
gagagctatc cgaacgtgca tcatctggtc agttgcgtca ggggcgagct ggctcccggc 1020
aaggatgccc tggatctgct cgccggcagt tttccgggcg gctccatcac cggcgcaccg 1080
aagatccgcg ccatgcagat catcgaggaa ctggaaagca gacgccgcgc catctactgc 1140
ggttcgctgc tctatctgga tgccggcggc aggctggaca gctccatcgc cattcgcacc 1200
ctgctggccc gcaacgggcg catcacctgc tggggcggcg gcggaatagt cgccgactcc 1260
gactggcagg cggagtatca ggagtccatc accaaggtgc gaacactgct ggcgaccctt 1320
cgcgcactct ga 1332

<210> SEQ ID NO 157
<211> LENGTH: 1230
<212> TYPE: DNA
<213> ORGANISM: Acinetobacter baumannii

<400> SEQUENCE: 157
ttgccaaaaa attatttgat cgttcgaaat aaccaaaact ttttattcac taaaactgat 60
ttaaataaat ataagttttc atcttatata gaaaatcttt tagattttac acaattccaa 120
tctcaagaac taaaaaatag caatagagaa aaaataagtt ttaagggtgg atatattggt 180
tttattagtt atgacttttc tgcacatcaa tttataaata atcaatcaca taaacaaccg 240
tctttattta taggttccta ttattctttt attaaaaaaa taaataatga atggtatttt 300
tttagcgatg aaaataatgc ttttgaaatt tttaactatc tttcagctct actcaataaa 360
ccttctagca aactacaaaa aaataatttt aaactagaac aaaatattca tcctcgctgg 420
tctaagaata catacttaac tgcttttcac aaaatacaag aatatattaa ggcaggagat 480
tgttatcaaa ttaaccttac tcaagaattc aaagcgaatt ttactggttc attattaaat 540
aaagcagatg agctatggaa tttaaccaat gcaccatatt ctggttattt aaaattaaca 600

-continued gaatttgagt tgttaagttg ctctcctgaa ttatttattg aatttaatgt agataagcaa 660
attaaaacca gacccattaa aggtacaatg cctcgttatg agaataaaaa gcaggattta 720
ctttcaaaac aaactttaaa aaattctaaa aaagatcaag cagaaaatgt gatgatcgtt 780
gatctattac gtaatgattt gagcatttat gccaatacag gttcggtaaa aacaacaaaa 840
ctattcgaaa ttgagagctt caatcaagtt catcatatgg tgagtgagat tacggctaca 900
cttaaaaatg atattaatcc tatgcagatg ttactcactg cattaccagg aggttcaatt 960
acaggagctc ctaaaattcg ggcaatgcaa attattgaag agctagaagg cgcacctcgg 1020
ggagcatatt gcggcacttt aggatatttt aatttcgatg gtactggacg ctggaatatt 1080
ttaattcgta gttttcaaca atatcaaaac cagctctcta tttgggcagg cggcggtatt 1140
actattgctt cagaggctga ggctgaatat caggaaagcc ttgataaaat ctctgctatg 1200
ctgaacttga tgaacagcac agcagaataa 1230

<210> SEQ ID NO 158
<211> LENGTH: 1404
<212> TYPE: DNA
<213> ORGANISM: Shewanella woodyi

<400> SEQUENCE: 158
atgagttgtt cggcgtcgca tcaacttgca gttcgcaagt tgacttggga tcatacttct 60
acagcacttt tttcacattt ttcagatcag ccttgggcca tgctattaga ttcagccaac 120
gcccctcacg cagacgctaa acacgacatc atagtgtgtg agcctgtggc aacaatcgtg 180
actgagtctg gattaagtaa agttagccat tatgaaggca atcgcgttac cagagtcgat 240
actttaacgc ttgatccctt caaggttatc aagcaaagcc tcaatgatta cttccccact 300
cctttaacaa gtcagcttcc attctctggc ggcgctctgg gcagttttag ttacgatcta 360
ggtcggcaga ttgaaaagct accagatatt gctcaacggg atataggttt agcagagctc 420
aatataggac tctatatgtg ggccctaatc tatgactatc aatcagcgtg ctggctttta 480
gttcattacc aaggagagga agcgctacaa aaacaattaa ttaagcttga atctctgctt 540
aacaagaata acaatgaaaa taatcaaaca tttaccctca ccagtggttg gcataatcaa 600
atcagccaag agcaatacaa agagaaattt gctcaagtgc aacgttacct gcatagcggt 660
gattgctatc agataaattt gactcatagg ttcgaagccg attatcaagg tgatgagtgg 720
caggcatata ctgagctgag taaaaccaac aaggccccct tctctgcatt tatcagacta 780
gagaacgcag ccatattatc tatttcacca gagcgctttg tgcagttggt ggatagagat 840
atacaaacca agccgattaa gggaacccgt ccaagattca gctgccctgt acaggatagt 900
gagtctgcta tagcactttc actggccaca aaagatcgag cggaaaatct gatgattgtc 960
gatctgctgc gcaatgatat cggtaaggtg gcacaagcag gctcggtgaa tgtccctcac 1020
ctgtttagta ttgaaagctt tcccgctgta catcaccttg tgagcacagt cacagcaaag 1080
ttagcgcctc aatatcaggc aagtgatctg cttaaagcta ctttccctgg aggctcaatc 1140
acaggagctc ctaaaattcg tgctatggag atcattgagg aacttgaacc ttcaaggcgt 1200
agcctatact gtggttctat cggctatata agccaagatg gccaaatgga taccagtatc 1260
accattagaa ccttggtagc ccaatcaaat cggatctact gctgggccgg tggtggcatt 1320
gttgccgact cagtggcaga tgaagagtac caagaaacct atgacaaggt gagtaaaata 1380
ctgccgattc tggagaagat gtaa 1404

<210> SEQ ID NO 159
<211> LENGTH: 1464
<212> TYPE: DNA
<213> ORGANISM: Zymomonas mobilis

<400> SEQUENCE: 159
atggaagtct tccgcccgac tatcagcaat cctgataaat ttcagatcgg taaagcaatg 60
tggctacaaa aaattgatct taaagacccg ttggtcgccg cgaatatcct ttcttcccga 120
ccgtattttg cttttcttga tagtgcgatg catcaggata aattggggcg atattcttat 180
atcgcagttg atcctttttgc gagactgacg gtttgtggtg accaagccta ttggaattca 240
gttcccgaaa aaggtgatcc tttagagctt ttgcaacggc atttggcgca attcgctttt 300
gatgaaaaaa ttgaacggcg ctttcctttt caaggcggat gtattggtta tgtcggttat 360
gattatggcc gctgccttga ggtcatcaat ggctatcctg aaacagaaga caaagccgcc 420
gatatcaatt tttgttttta tgatgtggtt ctggcttttg accatatgac gggggaaagt 480
tacctttgct cttccggtta tcctgaaacc caacctgaca aaaaagaaag ccgagcaaaa 540
gcccgtttgg cacaattttc tgactggctt tcgatgcctt ctaaacaggc atctttggat 600
gaaaagccca acaggctttc attaaattgg caatcgaatt ttacgaaaga acattattgt 660
caggcgatcg aaacagttcg ggaatatatt cgaaaaggcg atatttatca ggcgaatatc 720
gcccagagtt tttccgctga attgccggat gattttcagc cttggccttt ttatcgccag 780
ttacgtcgca tcaatcctgc aacctttggg gcgtatcttg cttttggcga tcaggttatt 840
gcatcggctt cgccggaacg ttttgttctg ttgcaggata atcagattga gacgcgtccg 900
attaagggga ctgcccgccg gtcaccagat cttgagaaag atagagccgc cgctgaagaa 960
ttgcttcatt ccgaaaaaga ccgcgctgaa aatatcatga ttgtcgatct gttgcggaat 1020
gatttgtcac atgtgtcaac ggcggattct gtcgaagtaa ctgatttatg ccgcctagaa 1080
agctatgctg gtgtgcatca tttggtgtcc gtggtcaccg gaaaattacg gcctgaaaat 1140
tcttccgttg atcttttgaa agcctgcttc cccggtgggt cgattacagg cgcgcccaaa 1200
attcgggcga tggaaattat tgcagaaatc gaacaattgg cacgcggcgt ttattgtggg 1260
tcgattgggt atattgattt tggcggtaat ctcgatttca acattgcgat cagaaccgtc 1320
accctgagta aaaacaaagc ggtttttcag gtcggaggcg ggattaccct gctttccgat 1380
cccgaagcgg aatatgtcga gaccctgacc aaggcagcaa aaatctttga aagttttggc 1440
acatcggttt ctgaaatggc ttga 1464

<210> SEQ ID NO 160
<211> LENGTH: 1347
<212> TYPE: DNA
<213> ORGANISM: Clostridium perfringens

<400> SEQUENCE: 160
ttgaattttg aaattaagga aatagaaaat aagcttaagc cacatgaagt atattttta 60 tttaaagatg aaataaacag tatattttta gatagttcaa aggaagatag cgaattttct 120
ttatattcat tcataggatt aaatcctttt aaaaagttta tctctaaggg aaatgagatt 180
tttatagatg aaaaactagt cttaggagat ccttttaaaa aattagaaga gcttatttta 240
gaatataaaa taaattataa tagtgagata cctttttag gaggtgctat gggatatttt 300
tcttatgata taggaagagt tattgaagat atgcctaaaa gtgctaagga tgatgtgtgt 360
attccagata gttattttt attttatgat aatgtaataa tatttgattt gagaaatcaa 420
aaaacatata taacagccct aggaattaag gaagagtcag aaaaaagtat agctaatatt 480
tatgagagga taaaagataa ggatataaat ttaaatatca gcttagataa aaatactgag 540
tttagttcaa atttttcaag agaagaatac ataaattcag taaaaaaggt taaagagtac 600
ataaaagaag ggcatacata tattgcaaac ctaacacaga gattttcctg tgattttaat 660
tctgatcctt ttgatacata tataagtttg agaagtataa ataaagcccc tttttcctgt 720
tatttaaatt tagatggttt tcaaattata agttcttctc cagagaggtt tttaaaagtg 780
tttaataata aggttgaaac aagaccaatt aaaggcacaa gaccaagagg aaaagataaa 840
ttagaagatg aaaagaataa aaaagaactt ttaaatagtg aaaaggataa gtcagagctt 900
ttaatgattg ttgatttaga gagaaatgat ttaagtaagg tatgcaaacc tttttctgtg 960
aaggttacag aattatttaa attagaggaa tatgctacag tatttcactt agtttccaca 1020
gttataggag aactaaagga agatgttagt tctgtaaaat gtataagaga atgttttcca 1080
ggaggttcta taacaggcgc tcctaaaata agaagtatgg agataataga ggaactagaa 1140
ggcattagaa gagggatata tactgggtcc ataggttatt ttgatttaag aggaaattgt 1200
gattttaata tagtaataag aactatatta gcaaaagata ataaggctta ttttggagta 1260
ggtggaggca taactattga atcagaagaa gagatggaat atgaggaaac tttagataag 1320
gcaaaggctt taatgagagt attataa 1347

<210> SEQ ID NO 161
<211> LENGTH: 1326
<212> TYPE: DNA
<213> ORGANISM: Saccharopolyspora erythraea

<400> SEQUENCE: 161
gtgttgcggc ggctctcgga ccgcgcccgg caacgcgggc tgccgccgcc cgccgcgctg 60
accggcgact ggttcggggg cggcgccgtg ctggtcccgt cggtgtccat cggtccccag 120
gacgacccgt tcgccgtcct ggacgccttc gactccgagg atgccgcgtc caccgccgat 180
gtgccggagg gcgcggtcgg gggcggctgg atcggatacc tcggctacgg cctgaccgac 240
ccgggaaggc acgcccagcc ccgcaggctg ccgttgtcgg cttggggctg gaccgaccac 300
gtcctgcgcc gcgaccgcga gggccagtgg tggttcgagt cgctcggtcc cgccgacccc 360
gccctcgtcg acgagttgac cgccctcgtc tccgacgccg acctcggttc cccttccgcc 420
cccggttcgt cgaccgatct cgcttccccc cagcattccc agtggcaggt ggggcccgta 480
cgccagccgg acgccgacct gcaccgcaag gccgtgcggg gctgcgtcga gcagatcgcg 540
gccggcgaga tcttccaggc caacatctgc agccgtttcg ccgtgccgtt caccggcgat 600
ccgctggagg tgttcgcggc gggcagcgag cggttccgcc cggcgcgggc cgcctacgtg 660
gccggcgact ggggtgcggt ggcgtcgctc tcgcccgaac tcttcctggc acgcagtggc 720
gacgtcgtgc actccagccc gatcaagggc acgctgccgc gtcgtggacc gcaggacgac 780
gccaacgcgg agctgttgcg ggcttcggcg aaggatgtcg cggagaacgt gatgatcgtc 840
gacatggccc gcaacgacct tggccgcgtc gcgtcgaccg gtcgcgtcac cgtccccgaag 900 ctgctcgatg tgcagccgca cccgggtgtc tggcacctgg tctccgacgt gcgcgccgag 960
gtcccagccg ggctgtcgaa ctcgcgactg ctggaggcga ccttcccgcc ggcgtcggtg 1020
accggcgctc ccaaggtccg ggcgcttgag gtcatcggcg aactggagga cgtggcgcgc 1080
gacgtctact gcggtgcggt gggcatggtc tcccccgcgg ccggcctgga gctgaacgtc 1140

```
gcgatccgca ccctggagta ctccaacggc atgcttcacc tgggtgtcgg cggcggcatc   1200

accgccgact ccgacccgga gcgcgagtgg caggagtgcc tgaccaaggc cgcccctctg   1260

ctgtcgctgc tgcgcagcgg cacctcacaa cagtcgaccg acacggccac cgcctcaacc   1320

tgctga                                                              1326
```

```
<210> SEQ ID NO 162
<211> LENGTH: 1926
<212> TYPE: DNA
<213> ORGANISM: Cupriavidus taiwanensis

<400> SEQUENCE: 162

gtggtagcaa gcatccagcg ccccccctct cccccagccc ctctcccgca agcgggagag     60

gggggcacgc aagcgggcgg cgttgacgcc tacgtcctgc tcgacgacgc cacggcaccc    120

gccgggcaag ccgcatcccg tctctacacc ggcttcgtcc gagaagacct gctgccgccc    180

ggcagcgaca tcgcccggct cgacgccatg cttgccgaag gctggcgcca gggctggcac    240

gcgaccctgt tcgcgccgta tgaattcggc ggtgcgctgg tcggtgcccc ggtgcatacc    300

ggcaacgcca tgccgttcca cgacggcgcg ctgcgcctgc tgtggttccg ggagctgcaa    360

cggctcgatg ccgcggcggt gggggcgtgg ctgcaagccg aggcggaccc gcagccagcg    420

ggcctgatgc atatcgcttc cgatacgtcc cgcgcggcct tcgatgatgc gattgcccgc    480

atccaccagt ggatcgaagc cggcgacacc taccaggtca actacaccca gcgcctgcgc    540

tgcgatgcct tcggcgatcc ggtggcgctg tacgcggcgc tgcgtgccgc gcagccggtg    600

ccttacggcg tgctggcgcg gcttccgggt gacgccatgg tgctgtcgct gtcgcctgag    660

ctgttcgtgc gccacgacgg cgagggccat ctgctgacgc ggccgatgaa aggcaccgcg    720

ccgcgcgccg gcgatcccgc gcgcgatgcg caggcggccg ccgcgctggc tgccgacgcc    780

aagaaccggg ccgagaacgt gatgatcgtc gacctgctgc gcaacgacct gggccgcatc    840

gcgcagccgg gcagcgtggc ggtgccggag cgctttgcgg tgcagccgtt cggcgcggtg    900

ctgcagatga cttccaccgt gaccgcgacg gcgcggcccg gcaccagcct cggtgcgctg    960

atggcggcgc tgttcccctg cggctcgatc accggcgcgc ccaagcggcg gaccatgcag   1020

atcattgcgc agctggagcg cgcgccgcgc gggctctaca ccggcgcgat cggctggatc   1080

gacgcgccgt ccggggccat ggccggaccg ttcgcgctgt cggtagcgat ccgcacgctg   1140

gtgctggcgc cgcgcgccgc cagcggcttg cgcgcgggcg agatgggcgt gggtggcggc   1200

atcgtccatg acagcgtggc ggcggaggaa ttcgccgaat gcggctggaa ggcccgcttc   1260

ctgacccgcc acgatcccgg cttcacgctg ttcgagacct tgcgcgtgca ggacggggcc   1320

tgtccgcagt tgccgcgcca cctggcgcgc atcggcgcct cggcgcaggc gttcggcttt   1380

gccttcgatg ctgacgccgc gtgcgaagcc gtggccgcgg aggccgcccg actgggggcc   1440

ggcacctggc gcctgcgcct cagcgtggac aagtccggca cgctggcgtt ggccagcggc   1500

acgctggcgc cgttgcccgc gggaccggtt ggtgtcgaca tcgcgccgga cccgctgccg   1560

cttgccgacc cgctgcgccg ccacaagacc agtgcgcgcg cggtcttcga tgccggctgg   1620

caggcggccg agcgcgccgg cggcttcgac cggctgttct tcaacacccg cggcgaactg   1680

ctcgagggcg ggcgcagctc cgtgttcgtg cgcatcgatg gccgctggct gaccccgccg   1740

ctgtcggccg atatcctgcc aggcgtgatg cgggcggtgg tgctggaagc gggcggcgcg   1800

gcgctgggca cgccgggcga gcaggtcgaa gaagccgtag tcacgcgcgc gatgctggcg   1860

cgcgccgagg ccatcgtgct ggtcaacgcc ctgcgcggcg tgatgccggc caggttgcag   1920
```

gcctga 1926

<210> SEQ ID NO 163
<211> LENGTH: 1890
<212> TYPE: DNA
<213> ORGANISM: Chromohalobacter salexigens

<400> SEQUENCE: 163
atgcacaacc tcgaagaaca gcaggacgat aatatattca tactgctcga aaatacacgc 60
tgttcgaacg gcaaccgtac ctctttattg ttcgagaacc cggttttcga ggttatatgc 120
tatcgcaacg acgcgttgcg cgccgccttg cgggagatcg acgagctgcg tggacagggc 180
tattacctca gcggttacct cgcctacgaa gccggttatg cgctttccga caagcaggat 240
ttcgcctttt gccggcgccc ttcgagcgac acgccactgg tgcatttcta tgcgtttcgg 300
gacgtacggc gtttgtccca gcagcaagcg agccggttcc tcgagtcacg gactcccgat 360
gccacgccgt cggccattcg ccacctggca ctcaacgaaa ctcgcgaccg ctatctcaaa 420
aacatcgaaa agataaagtc ctacattcgt gaaggcgata cttatcaaat caactacaca 480
ctgaagtatc gtctcgaata tcagggatcg ccgatcacct tgtatagaaa acttcgtcat 540
cgacaaaaag tcgaattcgg cggcttcctg aactttccgg aatattcagt cctttctctg 600
tcgccggagc tgttcctgcg caaacaaggc accgcgctgg aatccaagcc catgaaaggc 660
actttcccgc gcggcgtcac gccgcaggaa gatgccggca ttctcgacac catgcgccat 720
gatgccaaga cacgctcgga aaacgtgatg atcgtcgatt tgctgcgcaa cgacatcagt 780
cgtattgcct caccagggtc ggtggccgtc aagaacctgt tcgagataca gacattcgag 840
acgctgcacc agatgatttc cacggtgacc ggcagtatcg cctccgatgc caggatcgag 900
catgtcttcc gcgaactgtt tccgtgcggt tcgatcaccg gagcccccaa gatacgcacg 960
atgcagatca tcgaggagct ggaacgcgag ccacgcggcg tctataccgg cgcgatcggg 1020
tatctcacgc cgcacaacga cttctgcttc aacgttccca ttcgcacctg catcgcacat 1080
gccgacggta cggctgagat gggcgtcggc ggcggtgtgc tcttcgagtc cgatgccgag 1140
gcggagtatg cggagtgcct gctcaaggca cgcttcctga cgggactcaa tcaggacctg 1200
caactgatcg agacgatgcg ctattccaac gccgaggcac gcatcgagca cctcgaggaa 1260
catctgcagc gcctggcgcg ttcggcgcac gatctgcagt tcgtcttcga tgggccacgc 1320
gtgcgtgacg ccctcggcga ggccatcgcg gatcttcgtc acgatgccaa ggtgcgcctg 1380
ttgatggcac acgacggtca gctcgaggtg accacggctc cgctgccggc catgcccgag 1440
agtacgcaga ccgcccgcct ggggatcagc gaccagcgta tcgaccgacg cgatttcctg 1500
ctgcagtaca agacgacgga gcgttcgctg tacgagcagg cttaccagca ccaccgcgag 1560
gccggcgact acgacgtcgc ttttctcaac gcggaaggac gcctgaccga ggcgagtcgc 1620
cacaacctgt tcatcgaaaa ggacggcctg ttgctgacgc cgccgctcga ggaaggcgta 1680
ttgcccggca tcgcccgacg catgctcatc gaaacgagtt gcgagcgttg ctgcgagcgc 1740
ccgctgaccc cgcaggatct gctggaggcc gatgccatct ggttgaccaa tgccgtgcgt 1800
ggcgtcgtgc cggtcacgct cggcaagcag gctcgccaaa ccctcatcgc cgtggccggt 1860
caggaggctg cacatgcttt gcttgattga 1890

<210> SEQ ID NO 164
<211> LENGTH: 1977
<212> TYPE: DNA

-continued

<213> ORGANISM: Pandoraea pnomenusa

<400> SEQUENCE: 164
atgcaaagtg aagcgccctt ggccgcgttc gcactgttgg acgacagcgc ggatccggcc 60
ggtggagcgc gtctgtatac cgggctcgtg cgcgaggtga cttgcgacga gcccggtgtg 120
ctttccgacg cgcttcgcga agtggaggaa gccacccgcg acggcctgca tgccgtgctg 180
ctggccgatt acgaattcgg cgtgcgcctg gccggcgtgc atacggtcgc gacgcgtcgc 240
gcacccgggc agttccgcgc cctgttgttc gccaccctgg cgcacctgag cgccgcgcag 300
acgcaagcct ggctggccgg ccgtgaggcc gcctgcgcgc aggcgagccc acgggacatc 360
gatcacgccg ccggcaccga cgatatcgcg ccgccgggcg tggcaggcgt tgccgcgttg 420
caggacgacg tgagcgatgc ggccttcgac gacgccatcg ctcgcattca agactggctc 480
gcgcaaggcg agtgctacca gatcaattac acctatcgcc tgaatttcga cgcattcggc 540
tcgcccgtgg cactgtaccg ccgcttgcgt gcgcgccagc ccgtgcctta cggggcgctg 600
gtgatgcttc ccggtgccgg atgcgtggca ggtcgggcga tactctcgct ctcgcccgag 660
ctgttcctgc gtcattcgcg cggacgggtc gaggcgcggc cgatgaaggg caccgccccc 720
gcgtgcggcg acgccgccgt cgacgccgag cgcagtgcgg cgcttgccgc cgacgagaag 780
aaccgcgccg agaacctgat gatcgtggac ctgctgcgca atgatctcgg gcgcgtcgcc 840
acaccggggt ccgtcaaggt gccgaaactc ttcgaggtca cccgcttcgc gagcgtgctg 900
cagatgacgt cgaccgttac ggccacgcta ccgccctcgg cctcgttggc tgacgtcatg 960
cgtgcgctgt atccctgtgg ctcgatcacc ggtgcgccga agtatcgtgc gatgcaactg 1020
atcggcgagc tcgaaacgtc gccgcgcggg ctctataccg gtgccatcgg ctggctcgat 1080
gcccgcgaag acgcgccggc agcgctcggc gacttctgcc tgtcggtcgc cattcgaacc 1140
ctcgaactcg atgcacccat ggccagcgga ttacgtcgcg gacgtctcgg tatcggtgcg 1200
ggcatcgtgc tcgacagccg tgcccgcgag gagcgcgagg aatgcaggct caaggcgcgt 1260
ttcctgagtg cgctcgaccc ggggttcgag atcttcgaga ccatgcgggc gacaccgttg 1320
tcgggcatcg accatctctc gcgccatctg gcgcgtctgg cggcgtcggc aaagtacttc 1380
ggctttcgtt tcgacgaggc gtcgttgcgg gcacaactcg acgcggtggt cgcaacactc 1440
gacgcgagcg agatccatcg cgtgcgcctc gccctctcgc acgacggcgc cgccacgatc 1500
acgcacggcg tgctcgaacc gctcgcgcag ccgagcgtga cggtgtggct cgcgaacatg 1560
agcgaggcga cgcgtgccga cgatctcttc ctgcgtcaca aaacgaccgt gcgcgagcgc 1620
tacgatacgg cgtggaaggc ggcgcaggcc cgtggcgcgt tcgacatgct gttcttcaac 1680
gagcgcggcg agctgaccga gggcgggcgc agcagtgtgt tcgtcaagcg cgacggtctc 1740
tgggtgacgc ccccgctgtc gtgcgggttg ttgccgggga tcatgcgcgg cgtgatgctc 1800
gacgacccgt cgtgggccgc cgtcgaggac gtgctgaccc gtgaagacgt cgagaacgcg 1860
caggccatcg tggtttgcaa cgcattgcgc ggcgcgctac ccgcgtcgct cagcttccct 1920
gacgcgacgc catctccggc acgaacagtt cgctccactt cgccggccgc gtcttga 1977

<210> SEQ ID NO 165
<211> LENGTH: 1887
<212> TYPE: DNA
<213> ORGANISM: Lactococcus lactis

<400> SEQUENCE: 165
ttgaaggaat ttataataaa aaatacggat atttggaaaa ttttcctaaa atattatcgg 60

-continued tcagatgaag aaattgtttt tttacatagt agtcaggtga ccgaaaatga gcattatagt 120
attttagctc ataaacctta taaaaaggtt tcaaaatata agggtcaagt gttttttaat 180
ggtgaaaaaa agaagttcaa ttttttagat gcggtagatt tgctgaagga tgagagagtt 240
gaacgaccta aaaattggcc tttttatcca gaattattgg gttttgtaag ttatgagcaa 300
gatccggctt gttttgcagc ttatgatgaa gttttacttt ttgaccatag aacaaaactg 360
ttacgtgtcg tgcaatttga acaaactgat ggccaatatt ggctgactga atcggaagaa 420
attgaagtgg attcagagat tgagttcgat ggtcagaatg gcataggggc tatttttatt 480
gaccaaacga ggcaagaata tattgcttca ataaaaaaat tacaagatta tatgaaggct 540
ggcgatatct atgttgccaa tttgacgcaa caatttgaaa tttggtccga tcaaaaacct 600
attgaagttt ttaagaaaac aaggaaacaa attccagctc ctttctcatc atttttacaa 660
tatcctgaat ggaaaatgac gcaaatttca agttcagtgg aacgctttgt ttctattcat 720
gatggagcat taatttcaaa accaattaaa ggaacaattg ccagaggaga agatgttgga 780
gctgatagat tacaaaagga aatactttcc gacagtagta aagaacggtc tgagttactg 840
atggtgacgg atttattgcg taatgatatt gtccgaatta gtcaaccttt ttctttgtct 900
gtccctaaat ttgcagaaat tgaaactttt tctcatgttc atcaactggt gacttcaata 960
aaaagtagaa ttaaagaaga tttgactttt tcagaattta tgacggcttt attcccggga 1020
gggtcaatca caggtacacc taagaagcgg gcaatggaga ttattaagga agttgaaaaa 1080
caacctagag gaatttatac agggatgcag ggttggttaa gtcgagaaat ggatttggat 1140
atgaacatcg tgattcggac attagttcat gacggtgagc attatcaact tggtgtaggc 1200
ggtggaatta cgttcgagag caaagcagaa gcagagtttt cagagatttt actaaaagca 1260 aaacccttttt tagatatttt aggtgtaaaa gatgttccaa gtattttatt tacaacaggc 1320
attattaaaa atggtgaatt gttaaattta gagggtcatg tcaatcgctt gaaaaaacaa 1380
taccatcatc cagatttgga agaaaaattg agaatatttg cccaaaatgt tactgacggc 1440
gttttacgta tcagtactga cggagattct ttgtcccctg ggattcgtca gctgacgcat 1500
tcaaatgagg cctatcgagt taaactgtcg tcaattaatg acaaacctag tcttttgtct 1560
aactttaaac tttcaggccc agattttcaa aaggtctttc gtcaggaagt cttagaagcg 1620
aaaaaagaag ggtttcaaga tattctattt catacagatg gtttgatcag tgaattatca 1680
atcggaaatt ttgtggcaaa aaaggggaat cagtacgaaa cgccagccaa atatgctcta 1740
aaaggaactt ttttagattt atttgcgaaa aatcatacgc taatatataa agatattgcc 1800
ctttctgatt tgaaaacata tgattgtttt tatatgacaa atgctgtcag aggattagtt 1860
gaaataaaaa ttgatggaat ttcctaa 1887

<210> SEQ ID NO 166
<211> LENGTH: 1722
<212> TYPE: DNA
<213> ORGANISM: Streptococcus pneumoniae

<400> SEQUENCE: 166
atgcatagaa aaacagtgat tgattttagg actttggggg agagatatac ctttacccag 60
cctattaaag agttgaaaac gagaaatgta gaagaagtgg cagatttgct ggcacaagtg 120
gaaagctacc aagagcaagg ttattatgtg gtggggtatg tcagctacga ggctgcacct 180
gcttttgagg aaaaattagc agttcacaag gatcccctac tgggagagta cctgctttac 240

-continued

```
tttactgttc atgatatcgt agaaacttcc cctattcctc tgacttatga ggatattgat     300

ttgccctcaa attggcagga agtaacgtct gcagcagact atgaaaaggc cattgcccaa     360

attcaccatc atttacggca gggagatacc tatcaggtca actacaccgt ccaacttaag     420

caaaagttaa atgccaatcc ttttgccatc tacaatcgta tggtggtaga gcaggaggcg     480

ggctacaatg cctatgtgga acatgacgag atgacagtga tttccatgag cccagagctc     540

ttttttgagc aaaatgatcg cgagttgaca acacgaccaa tgaaggggac gactcagcgt     600

ggggtaactg accaagaaga tcttgaacag gccagttggt tggaacagga tcccaaaaat     660

cgctctgaaa atatgatgat tgtggacctc ttgcgcaatg atatgaaccg tatttctgaa     720

gttgggagcg agcacgtgga gcgtctgtgt caggtagagc agtattcaac tgtttggcag     780

atgacttcga ccatcaagag tcagttgcga gaggatgtgg accttgttga aatcttccgc     840

tcactctttc cttgtggttc cataacgggt gcaccgaaaa ttgcgacaat ggagattatc     900

aaggacttgg agcctcaacc gcgtggagtc tactgtggaa cgattggtct cttgcttcca     960

aatggacgac ggatttttaa tgtggccatt cgtaccattc aacttcacaa aggtcaagcc    1020

atttatggag ttggcggagg gattacttgg gatagcacat gggaatctga ataccgagag    1080

gttcatcaaa aggcagcagt tctctatcgt aaacaagctc gcttccaatt aattacaact    1140

ggaaaaatca gccaaaaaca actgatgttt gaagaacaac atctggaaag gctgagaaaa    1200

gctagtcgtt attttgcttt tccttttgat gcagaagact tgggacacaa gattgaggaa    1260

gagtgtcagg attgtgaagc taatcgagat taccgcttgc gaatcagcct tagcaaatct    1320

ggagagatag aagtcaatcg tcaagtatta acccctctca gtacaagctt ttgtcaggcc    1380

caagtctgtc ttcaggaagc tgctttgaat caatccttta cctactttaa aaccactcac    1440

cgaccgcatt tgagcctagg agaacaagag aagatttacc acaataagtc aggagaactg    1500

cttgaaacct ctataggaaa tttggttctg aaaatcgctg gaaaactcta cacaccgcct    1560

atccgacttg gaatcttgcc aggaatttac cgtcagcatt tgctagaaac aggacaggta    1620

gaagagaaag tcttgacctt ggcagattta acccaagcag aagctattta cggctgtaat    1680

gcagtgagag gcttgtatga attaagcctt gaggagaact ag                      1722
```

```
<210> SEQ ID NO 167
<211> LENGTH: 1719
<212> TYPE: DNA
<213> ORGANISM: Streptococcus thermophilus

<400> SEQUENCE: 167

atgcataaga aaaccgttat tgattttaaa gaacttggcg tcagacaaat cttcactcac      60

gccataaaag agataaaaac caaagacatt aaggaagtta aatcacttat aaatcaaata     120

gaagcctatc aagaaaaagg ctattttgct gtaggctatg tagcctatga agcttctcag     180

gcctttgaac ctaaatttca aatttttgat agcccattaa tgtcagagta tcttctctat     240

tttactattc acgacactgt tcaaacagag tctatccctc ttgcttatga gcctgttccc     300

ttaccagaat cttggcaaga actaacttct gcagaggaat acaaggctgc tattgagcat     360

atacaccacc atattcgtca aggaaacacc taccaggtca attttaccgt ccaacttcaa     420

cagaacataa cagctgatcc atttgccatc tacaaccgat tggttgttga gcaaaatgca     480

cattacaatg cctttattca acatgatgat gtctccatca tttccataag tcctgaactc     540

ttctttaaaa aagatggtga tatattgacc acacgtccta tgaaagggac aacaaatcgt     600

ggcttgacaa ctgaaactga ccttaaacaa gcacaatggc ttgctcatga tcagaaaaat     660
```

cgctctgaaa atatgatgat tgtagatctt cttagaaatg acatgaatcg tatttcaaaa 720
atagggagtg aaaatgtaaa aagactttgc caggttgaac aatactctac tgtttggcaa 780
atgacttcaa ctattgagac gcaactccta ccaaacagtc gtttggatga catcttccaa 840 gcccttttc cttgtggatc tattacagga gcaccaaaaa tagctactat ggcaattatt 900
aaaaacgtcg aaaaacaagc tcgaggcgtc tattgtggag ccattggtat cttgctacct 960
aatggaccaa ctattttcaa cgtagccatc cgaacacttc aaatgcaggg aaacaaggct 1020
atatatggag taggcggtgg aatcacctgg gacagcaaat gggaagctga atatgaagaa 1080
acaaagcaaa aatcagctat tctataccgt caaaatccta gatttgatct tatctcaact 1140
ggacggattc atcaaggtaa actactccat cttaaagaac atctcaatcg tctacaagag 1200
tccagtcgct attttgctta tcctttcaat aaaaaagaag ttcaaaatca agtcgaagat 1260
ttgtgtcagt ccccttgattt tgacacagac taccgtctta aattgtccct tgcaaaagat 1320
ggtaaactta cttttgaaca tgctcaatta acagaattag acgatgattt ttgtcaagca 1380
agattagtta agcaaacaca tcctttgaat aacccctata cctactttaa aacaagttat 1440
cgaccacaca ttagtctagg acctcatgag caaatctact ataatcaaaa gaaagaactt 1500
ttagaaactt ctatcggtaa cctcgttctt aaaatcaagg accaactcta cactccacct 1560
gttcacctcg gtcttttaaa cggtatttac agacaaagcc tcattgctaa taatcaggtc 1620
acagagaaag ttttgactct ggaagattta aaacaggctc aagccatcta tggctgtaat 1680
gctgtgagag ggttgtatga attgagggta gatttctaa 1719

<210> SEQ ID NO 168
<211> LENGTH: 564
<212> TYPE: DNA
<213> ORGANISM: Escherichia coli

<400> SEQUENCE: 168
atgatcctgc ttatagataa ctacgattct tttacctgga acctctacca gtacttttgt 60
gaactggggg cggatgtgct ggttaagcgc aacgatgcgt tgacgctggc ggatatcgac 120
gcccttaaac cacaaaaaat tgtcatctca cctggcccct gtacgccaga tgaagccggg 180
atctcccttg acgttattcg ccactatgcc gggcgcttgc cgattcttgg cgtctgcctc 240
ggtcatcagg caatggcgca ggcatttggc ggtaaagttg tgcgcgccgc aaaggtcatg 300
cacggcaaaa cctcgccgat tacacataac ggtgagggcg tatttcgggg gctggcaaat 360
ccacttaccg tgacacgcta ccattcgctg gtggtggaac ctgactcatt accagcgtgc 420
tttgacgtga cggcctggag cgaaacccga gagattatgg ggattcgcca tcgccagtgg 480
gatctggaag gtgtgcagtt ccatccagaa agtattctta gcgaacaagg acatcaactg 540
ctggctaatt tcctgcatcg ctga 564

<210> SEQ ID NO 169
<211> LENGTH: 564
<212> TYPE: DNA
<213> ORGANISM: Escherichia fergusonii

<400> SEQUENCE: 169
atgatcctgc ttattgataa ctacgattct tttacctgga acctctacca gtacttttgt 60
gaactggggg cggatgtgtt ggttaagcgc aacgatgcgt taacgttggc ggatatcgac 120
acactcaaac cgcagaaaat tgttatctca cctggaccct gtacgccgga cgacgcaggg 180

-continued

```
atctcccttg acgttattcg ccactacgcc gggagtttgc cgattcttgg cgtctgcctc    240

ggtcatcagg caatggcgca ggcttttggt ggcaaagttg tgcgcgccgc aaaggtgatg    300

cacggcaaaa cctcgccgat cacacataac ggtgagggcg tatttaaggg gctggcaaat    360

ccactcaccg tgacacgcta ccattcgctg gtggtggagc ctgactcatt accggagtgc    420

tttgaagtga cggcctggag cgaaacccgc gagattatgg ggattcgcca tcgccagtgg    480

gatctggaag gcgtacagtt ccatccagaa agtattctca gcgaacaagg gcatcaactg    540

ctggctaatt tcctggagcg ctga                                           564
```

<210> SEQ ID NO 170
<211> LENGTH: 564
<212> TYPE: DNA
<213> ORGANISM: Salmonella enterica

<400> SEQUENCE: 170

```
atgatcctgc ttatcgataa ctatgattcc tttacctgga acctctacca gtatttttgt     60

gaactgggcg cggaagtgca ggttcggcgc aatgatgcgc tgacgctggc gcacattgac    120

gctttgaacc cgcaaaaaat cgttatctct cctggcccct gtacgccaaa tgacgctggc    180

atttcactgg cggtcatccg ccattatgcc ggacgtattc cgatgctggg cgtttgcctg    240

ggtcatcagg cgatggcgca ggcctttggc gcgtcggtgg tgcgggcagc gaaagtgatg    300

cacggtaaaa cgtcacctgt tacgcataat ggacagggcg tgtttcgggg attgcccagc    360

ccgttaaccg tgacacgtta ccactcgctg attgtcgacc ctgccacgtt gcctgagtgt    420

tttgagatca ccgcctggag cgaaacgcag gagattatgg gcattcgcca ccgcgagtgg    480

gatctggaag gcgtgcagtt ccacccggaa agtattctca gcgaacaagg acacgctctg    540

ctggaaaatt tcctccggcg ttga                                           564
```

<210> SEQ ID NO 171
<211> LENGTH: 564
<212> TYPE: DNA
<213> ORGANISM: Salmonella bongori

<400> SEQUENCE: 171

```
atgatcctgc ttattgacaa ctatgattcc tttacatgga acctctacca gtatttttgt     60

gaactgggcg cggaagtgca ggtcagacgc aatgatgcgt tgacgctgac gcagattgac    120

gccctgagtc cgcaaaaaat cgttatctct cccggaccct gtacgccaga tgaggccggt    180

atctctctgg cggtaatacg ccattatgcc ggacgtattc cgatgctggg cgtttgcctt    240

ggtcatcagg cgatagcgca ggcctttggc gcgtcggtgg tgcgggcagc gaaagtgatg    300

cacggcaaaa catcgcccat tgcgcataat ggtcagggcg tgtttcaggg ggtgcccagt    360

ccattaactg tgacacgtta ccactcgctg attgtcgatc ctgttacgct gcctgcttgc    420

tttgagatca cggcctggag cgaaacgcag gagatcatgg ggattcgcca tcgccagtgg    480

gatctggaag gcgtacagtt tcatccggaa agtattctta gcgaacaggg acacgcgtta    540

ctggaaaatt ttcttcaacg ttga                                           564
```

<210> SEQ ID NO 172
<211> LENGTH: 576
<212> TYPE: DNA
<213> ORGANISM: Yersinia pestis

<400> SEQUENCE: 172

```
atgctactgc tgatcgacaa ctacgattca tttacttaca acctgtacca gtatttttgt     60
```

-continued

```
gagctgggta ctgaggtgat ggttaagcgc aacgatgagt tgcaactgac ggatattgaa    120

caactggctc cctcacatgt ggtgatctct cccggccctt gtacccctaa cgaggctggg    180

atctcattgg cggttatccg ccactttgcc gataaactgc ctattctggg ggtctgcctt    240

ggtcatcagg ctctggggca ggcttttggt gcgcgcgtgg tgcgtgcgcg tcaggtgatg    300

cacggcaaaa cctcggcgat ttgccattct gggcaagggg tttttcgcgg gcttaatcag    360

ccattgacgg tgacccgtta ccactcttta gtcattgcca ccgactccct accgggccgt    420

tttgagctga ctgcctggac ggagcggggc ggtgagatgg atgagattat ggggattcgc    480

catcgcacat tgccactgga aggggtgcaa ttccatccag aaagtattct cagtgaacag    540

ggccatcaat tactggataa ttttcttaaa aattaa                              576
```

<210> SEQ ID NO 173
<211> LENGTH: 576
<212> TYPE: DNA
<213> ORGANISM: Yersinia pseudotuberculosis

<400> SEQUENCE: 173

```
atgctactgc tgatcgacaa ctacgattca tttacttaca acctgtacca gtatttttgt     60

gagctgggcg ctgaggtgat ggttaagcgc aacgatgagt tgcaactgac ggatattgaa    120

caactggccc cctcacatgt ggtgatctct cccggccctt gtacccctaa cgaggctggg    180

atctcattgg cggttatccg ccactttgcc gataaactgc ctattctggg ggtctgcctt    240

ggtcatcagg ctctggggca ggcttttggt gcgcgcgtgg tgcgtgcgcg tcaggtgatg    300

cacggcaaaa cttcggcgat ttgccattct gggcaagggg tttttcgtgg gcttaatcag    360

ccattgacgg tgacccgtta ccactcttta gtcattgcca ccgactccct accgggctgt    420

tttgagctga ctgcctggac ggagcggggc ggtgagatgg atgagattat ggggattcgc    480

catcgcacat tgccactgga aggggtgcaa ttccatccag aaagtattct cagtgaacag    540

ggccatcaat tactggataa ttttcttaaa aattaa                              576
```

<210> SEQ ID NO 174
<211> LENGTH: 564
<212> TYPE: DNA
<213> ORGANISM: Klebsiella pneumoniae

<400> SEQUENCE: 174

```
atgatcctgc ttatcgataa ctatgactct ttcacctgga atctgtatca gtacttctgc     60

gaactggggg cggaagtact ggtcaggcgc aacgatgcgt tgacgctgga ggagatagcg    120

gcgctggcgc cggagaaaat cgtgatctcg ccaggcccct gcacgccgga tgaggcgggg    180

atttccctcg cggttatccg ccactatgcc ggaaaaacgc cgctgctggg cgtctgtctc    240

gggcatcagg cgatcgccca ggcgtttggc gcgactatcg tgcgggcggc ccaggtgatg    300

catggcaaaa cctcgcttat cgagcataac ggcgaagggg tgtttcaggg gctgaataat    360

cccctgacgg tgacccgcta tcactcgctg gtgattgacc cgccgacgct cccgtccgag    420

tttaacgtca ctgcccgcag cgccagcggt gagattatgg ggatccgtca ccgcgaatgg    480

gatctcgagg gcgtgcagtt tcatccggaa agcatcctca gcgagcaggg ccatcaattg    540

ctggccaact tttgaaacg gtga                                           564
```

<210> SEQ ID NO 175
<211> LENGTH: 576
<212> TYPE: DNA

-continued

<213> ORGANISM: Xenorhabdus bovienii

<400> SEQUENCE: 175

```
atgctattaa taatagataa ctacgattct tttacattca atttatatca atatttttgc    60
gagttaggga caaatgtttt agttaagcgt aatgatgaat tacagcttga agatatcgag   120
aagttggcgc ccacacattt agtgatttcg ccggggcctt gtacgccaaa tgaagcaggg   180
atttcactag aggccattgc gcattttgcc ggcaaattgc caatcctcgg tgtgtgccta   240
gggcatcagg ctattgggca ggcttttggt gcgagtgtgg tcaaagcccg cgaggtgatg   300
cacggaaaaa acagcttgat ccaccataat caacaaggag tattcaaagg attgaaccgt   360
ccactgactg ttactcgtta tcattctctg gtgattgctg ctgaaaccct gccagcatcg   420
tttgaagtga ccgcatggag tcagcataac ggtaatgtag atgaaattat gggaatacgt   480
caccgtactt tgccattgga aggtgtgcaa tttcaccctg aaagcattct cagtgaacag   540
ggacatgatt tgttgaataa ttttctcaga tattaa                             576
```

<210> SEQ ID NO 176
<211> LENGTH: 576
<212> TYPE: DNA
<213> ORGANISM: Providencia stuartii

<400> SEQUENCE: 176

```
atgcttttac ttattgataa ttacgattca tttacttata acctatatca atacttctgt    60
gaattagggg cggaagtact cgttaaacgt aatgatgaaa tttctatcga agagatagag   120
ttgttagcgc ctacacacct agtgatctca ccaggccctt gtacgcctga tgaggcaggg   180
atctctcttg aagcaattaa gtattttgca gggaaaatcc ctatcttagg catttgtctt   240
ggtcatcaag cgatcggtca agcctttggt gcaacggttg tgaaggctag agaagtgatg   300
catggcaaaa catcggctat tcatcataac caccaagggg tatttaaagg tttaaatcgg   360
ccactaacag ttacacgtta tcattctctc gttattgctg cagaaacatt accagcgtct   420
tttgatgtct ccgcatggtc actgaataac ggtgacgtag atgaaattat gggaatacgt   480
cataaaactc tgccaattga gggggttcag tttcacccag aaagtattct gagtgaacaa   540
ggccatgaat tgctgaataa ttttttaaaa tattag                             576
```

<210> SEQ ID NO 177
<211> LENGTH: 573
<212> TYPE: DNA
<213> ORGANISM: Shewanella woodyi

<400> SEQUENCE: 177

```
atgcttttaa tgatcgacaa ttacgactca tttactttta acttagtgca atatttccag    60
cagctaggtc aagaggtcgt ggttaagcgt aatgatgaga tcactttagt agatatagag   120
aagctagcac caagccatat tattatttca ccaggtcccc gtagtcctaa tgaggcgggg   180
atatcgttag cggcgattga acattttgcg ggtaaattgc cgatcttagg cgtctgctta   240
ggtcatcagg ccatcgctca ggtgtttggg gcacaagtga tccgcgctaa acgtgtgatg   300
cacggtaaaa ccagctgtat taaccatctt ggtaagcgac tctttaaaga gctgaaagat   360
ccacttactg tgacccgcta tcattcactt ttggtcggct ctctgcctaa agacttcatt   420
ctcgatgcct ggttcgatga tgaacattgt ggtcgcgaga tcatggccat gagccataag   480
catcttccta tttatggggt tcagtttcac cccgagtcag tgctcactga gcaagggcat   540
gagctattgc aaaacttcct tagtttaagt tag                                573
```

<210> SEQ ID NO 178
<211> LENGTH: 612
<212> TYPE: DNA
<213> ORGANISM: Zymomonas mobilis

<400> SEQUENCE: 178
atgcttttga tgattgataa ttacgactct tttgtcgtta atctggcgcg ctattgcgaa 60
aggcttggcc gtaaagttag cttgtttcgc catgataaaa tcacccttga agagatcgag 120
gtgatgtcgc ccaaagcgat tatcctttct ccagggcctt gctcaccgga agaagccggt 180
atctctttgg atgttttacg gcaattttct ggcaagatac ctattttagg ggtttgcctt 240
ggacatcaag ccattggtgt tgcctttggt ggtgttattg cccgtgccag ctatccgctt 300
cacgggcgtg ccgtggaaat cagccatgtc gggaaaaggc tatttaaaga tattcccaat 360
ccttttaagg cggcacgcta taattcgctg attatccaga aaaccgaaga gatggaacag 420
catttgacgg ttgatgcgct gtcaccggaa ggcgagatca tggctttatc gcataaaagt 480
catccgacct atggtatcca gtttcatcct gaatcggttt tgaccgaata tggcgacgcg 540
cttttgtcgc gctttttga tttggaggaa gccttctatg ccgatatggc tgaacggtgt 600
attagccaat aa 612

<210> SEQ ID NO 179
<211> LENGTH: 585
<212> TYPE: DNA
<213> ORGANISM: Bacillus subtilis

<400> SEQUENCE: 179
atgattttaa tgattgataa ctacgattca ttcacgtaca acttggtaca gtatttgggc 60
gagcttgggg aagagctggt tgtgaaacgc aatgacagca tcacaatcga tgaaattgaa 120
gaactgtctc cggactttct gatgatatct cccggaccgt gcagccctga tgaggcggga 180
atcagcctcg aagcaattaa acatttcgca gggaaaattc ctattttcgg tgtatgtctc 240
ggacatcagt ccatcgcaca agtgttcggt ggtgatgttg ttagggcaga acggcttatg 300
cacgggaaaa cctcggatat cgagcatgac ggcaaaacca tttttgaagg gttgaaaaat 360
ccccttgttg cgacgcgata ccactcgctg atcgtaaaac ctgagacgct gccaagctgt 420
tttacagtaa cagcacaaac gaaagaagga gaaatcatgg ctattcgcca caatgacctc 480
ccgatagagg gtgtgcaatt tcacccagag tctattatga cctcctttgg gaaagaaatg 540
ctcagaaatt ttattgagac atatcgcaag gaagttattg cgtga 585

<210> SEQ ID NO 180
<211> LENGTH: 588
<212> TYPE: DNA
<213> ORGANISM: Bacillus thuringiensis

<400> SEQUENCE: 180
atgatattaa tgattgataa ttatgattct tttacattta atttagtgca gtttcttgga 60
gaacttggac aagagcttgt tgttaaacgt aacgatgaag tgactatttc agatattgag 120
aatatgaaac cagacttttt aatgatttcg ccaggcccat gtagtccgaa tgaggcaggg 180
attagtatgg atgttattcg atacttcgct gggaagattc cgatttttgg ggtttgtctt 240
gggcaccaat ctattgcgca agtgtttggc ggagaggttg tccgtgcaga gcgattaatg 300
catgggaaaa cgtcacctat gcatcatgat ggaaagacga ttttttcgga tatccctaat 360
ccatttactg cgacgcgcta tcattccctt attgttaaga aagagacgtt acctgattgc 420
ctagaggtaa catcttggac agaagaaggg gaaattatgg cgctccgtca tacaacatta 480
ccgattgaag gtgtacagtt ccatccggaa tctattatga cttctcacgg gaaagagttg 540
ttgcagaatt tcattcgtaa atacagtcca agtgtgacgt catgttaa 588

<210> SEQ ID NO 181
<211> LENGTH: 582
<212> TYPE: DNA
<213> ORGANISM: Lactococcus lactis

<400> SEQUENCE: 181
atgaaattgc tattaattga taattatgat tcttttactt atttgcttgc acagtatttt 60
gaggaattag attgtagtgt aacagtggtt aatgaccaag ataaaatgag tcagaaaatt 120
agaatttctc cggattttat ttgtgaaaat tatgatgcga ttatcatttc tccaggtcca 180
aaaacaccaa aagaagccgt ttttagtagg gatgtagttc aactatacgc tggaaaaatt 240
cctatgttag gaatttgctt gggtcagcaa gtcattgctg aatgttttgg aggaaatgtt 300
gttcttggtg agaggccaat gcatggaaaa atttctgtca ttcgtcataa ttgtcaagga 360
atttttaaag gacttccaca aaatttgaaa gttgcacgtt atcattcgtt gattgtcgat 420
aaactaccta atgattttga aattgatgcg cagagtgagg atggtgttat tcaggccatt 480
catcagccaa aattaaaatt gtgggcttta caatttcacc cagaaagttt agttactgaa 540
tatggtcatg aaatgttaaa taattttttg aaagtggtgt ag 582

<210> SEQ ID NO 182
<211> LENGTH: 699
<212> TYPE: DNA
<213> ORGANISM: Mycobacterium bovis

<400> SEQUENCE: 182
atgcggatcc tggtcgttga caactacgac agcttcgtgt tcaacctggt gcagtacctc 60
ggccagctcg gcatcgaggc cgaggtgtgg cgcaacgacg accaccggct atccgatgag 120
gccgccgtcg ccggccaatt cgacggtgtc ctgctcagtc ccggtccggg taccccggag 180
cgcgcgggcg cgtcggtgag tatggtgcac gcgtgtgcgg cagcacacac ccctttgctg 240
ggggtctgcc ttgggcacca agccatcggc gttgcgttcg gcgccaccgt ggaccgtgcg 300
cccgagctat tgcacggcaa gaccagcagc gtattccaca ccaatgtcgg tgtgctacaa 360
gggcttccgg atcccttcac ggccactcga taccattcgt tgacaattct gcctaagtcg 420
ctgccagcgg tgctgagggt cacggcccgc actagcagcg gtgtgatcat ggccgtgcag 480
cacaccgggc tgccgatcca cggtgtccag ttccatccgg agtcgattct caccgagggc 540
gggcaccgca tactggccaa ctggctcacc tgctgcggat ggacgcaaga cgacaccctg 600
gtacgtcggc tggaaaacga agtgctcacc gccatctcac cgcacttccc aacttcaacc 660
gctagcgcgg gcgaagctac tggccgaacc tcagcgtga 699

<210> SEQ ID NO 183
<211> LENGTH: 675
<212> TYPE: DNA
<213> ORGANISM: Mycobacterium smegmatis

<400> SEQUENCE: 183
atgcaggttt tggtggtcga caactatgac agcttcgtgt tcaacctggt ccagtacctg 60
ggccagctcg gtgtgcacgc gcaggtctgg cgcaacgacg acgcccggtt ggccaccgag 120
gacgcgatag cgcaggccgc cgccgacttc gacggtgtgc tgctcagccc cgggccgggc 180
acccccgaac gtgcgggagc ctccatcgcg ctggtgaagg cgtgcgccgc ggcgggcact 240
cccctgctgg gcgtgtgcct ggggcatcag gcgatcggcg tggcgttcgg cggcaccgtc 300
gaccgtgcgc ccgaactgct gcacggcaag accagcgtcg tgcaccacaa cgacagcggc 360
gtgctcaagg gtctgccgga tccgttcacc gcgacgcggt accactcgct gacgatcctg 420
cccgagacgc tgcccgccgc gctcgaggtc gtcggccaga ccgacaacgg catcatcatg 480
gccgtccggc acaccgagct gccgatccat ggcgtgcagt tccaccccga gtcgatcctc 540
acccagggcg gacaccgcat gctggccaac tggctcggct tctgcggcgc cgcaccggac 600
gagacgctcg tgcgccgcct cgaggacgag gtcgcccgcg cggtcgcggc cgctacgcag 660
cgaagctcag cgtga 675

<210> SEQ ID NO 184
<211> LENGTH: 687
<212> TYPE: DNA
<213> ORGANISM: Corynebacterium urealyticum

<400> SEQUENCE: 184
atgcgcatct tggtcgtcga taacttcgac agtttcgttt ataacctcgt ccagtacctc 60
gggcagctcg gctaccacga gcagaactgc gtggtgtggc gcaataacgc acccgagctc 120
ggcggtgagg caggtttcga cgacgccgac ctcgccgatg tgcttggtca gttcgatgcc 180
gtcctgctgt ccccggggcc gggcgaaccc accgccgccg ggcacctcat gcaggtcatc 240
cgcgtggccg tggatcaggg cattccactg ttcggcgtgt gcctcggcca ccaggccatc 300
ggcctgcact ttgggggcca agtcgtgcgc gcagacgagc tctaccacgg caaaacctcg 360
cccgtgaccc acgacggcac cggcgtgctg cagggcatcc cgagtccatt caccgtcacc 420
cgctaccact cgctgaccgt cgacccgggc tccgtgcccg aggagctggc ggtcaccggg 480
cgggtggatt ccggaatgat catggcgatg cggcacacca gcctgccggt gcactccgtg 540
cagttccacc cggagtccgt gatgacccaa tacggccacc gcatgctcgc gaactggctg 600
atcgaagccg gtttccccat cgatgaggac ctgctcggcc gcatcgagga agagcagctt 660
gccgtgaccg gtgcgctgag caagtag 687

<210> SEQ ID NO 185
<211> LENGTH: 669
<212> TYPE: DNA
<213> ORGANISM: Corynebacterium kroppenstedtii

<400> SEQUENCE: 185
atgcggattc tcgtcgtcga taattatgac agttttgtgt acaaccttgt gcagtacatc 60
gggcagctgg gggagacgtg cacggtgtgg cgtaacgacg acgaccgttt ggtggattcc 120
gcggaggatc gagccgcggg ccggtcggtt gttcaacgtt tcgacggcgt gttgatttcg 180
ccggggccgg ggactccgtc ggcggcaggt cagtcgattc cgctgatcaa agcatgtatc 240
cgtcatgagg tgccgatgtt gggtgtgtgt ttggggcatc aggcgttggc tgaggctttg 300
ggcggttcgg ttgtccgtgc ggacgagttg ttgcacggga agacgtcgcc ggtgtggcat 360
gacggtacgg gtgtgatgcg tggtttgccg gatcccgtga cggtgacgcg atatcactcg 420
ctgacggtgg atgaggcgtc gctgccggag gagttggtgg tgaccggtcg gtcggattcg 480
gggatggtga tgtccatgcg gcatgcgtcg ctgcctttgc atggtgtgca gttccacccg 540

```
gagtcgatca tgacgagctg cggccatcgg attgtggcga attggatggg atgcgctggt    600

ttccttgtcg acgaggaacg cgtgcgtgag ctggagaatc ggcataacgc cgtcttgtcg    660

ggcctgtag                                                            669
```

<210> SEQ ID NO 186
<211> LENGTH: 693
<212> TYPE: DNA
<213> ORGANISM: Corynebacterium resistens

<400> SEQUENCE: 186

```
atgcgcatcc tcgtcatcga taacttcgat agcttcgtct acaacttggt gcagtacatc     60

ggccagcttg gtttcacgga cgaggaatgc atcgtctggc gcaataatgc cccggaactt    120

ggtacctcca ccgatgaact gcgggatgcc ctttctttgt ttgacgccat cctcgtctcc    180

cccggccccg gtgaacctag ggcagcggga cgcacgttag aggtcattga gctagccgct    240

gagttgcgca aaccactgtt cggcgtgtgt ctcggacacc aagccattgg gcaacacttt    300

ggcgccaaag tcgttcgggc cgaggaattg ttccacggta agacttcgcc ggtaacccat    360

gatggtaccg gcgtattacg cgatatcccc agcccgttcc gcgtgacgcg ctaccactcg    420

ctcacggtag atccggcgac ggtccccgac gacctcatca tcactgcgca ttcggattct    480

gggatgatca tggcgatgcg gcaccgtgag ctaccaatcc atagcgtgca gtttcatccc    540

gaatcggtga tgacgcagta cgggcaccgc atgttggcga actggctggc ggaagtcgaa    600

ggtgccgcaa tcgacgagac gcatgtcgag cgtctcgtca gggaccagct gcaggtcacc    660

ggcgctatca gcgctgaatc ccacatgctg tag                                 693
```

<210> SEQ ID NO 187
<211> LENGTH: 708
<212> TYPE: DNA
<213> ORGANISM: Corynebacterium variabile

<400> SEQUENCE: 187

```
atgcgcatcc tcgtcatcga caactacgac agcttcgtct acaacctcgt ccagtacctg     60

ggggagctcg gcgaggactg caccgtgtgg cgcaacgacg ctcctgaact gggcgatccg    120

gcggacggag tggcgggtct ggacgctccg ctcggcgggt tcgacgccat cctcctctcc    180

ccggggccgg gcgaacctgc cacggcagga cgcatgctcg atgtcatcac ctgggccgag    240

gctcaccgga cgccactgtt cggtgtctgc ctgggtcatc aggcgattgc cctgcacttc    300

ggtggggatg tggtgcgggc cggcgagctg ttccacggca agacgagccc cgtcttccac    360

aacggtgtcg gtgtactcac cgacgtaccg tcacccttca ccgtggcgcg gtaccactcc    420

ctgaccgtcg atccggagac cgtgccggag tgcctcgagg tcaccgccaa ggtggactcc    480

gggatgatca tggcgatgcg gcacaggacg ctgcccatcc attccgtcca gttccacccg    540

gagtccgtca tgacgcagca cggtcaccgg atcctctcca actggctggc ggacgccggg    600

cgcccagtgg acgagcgaca gctgtccgtg gtggaggctc ggcatgctga ggcgcaggag    660

gcctcggcgg cggtcatcga aggggcacac ggttctgtgc tggcctga              708
```

<210> SEQ ID NO 188
<211> LENGTH: 690
<212> TYPE: DNA
<213> ORGANISM: Corynebacterium falsenii

<400> SEQUENCE: 188

```
atgcgcatcc tggtgataga taactacgac agctttgtct acaacctcgt ccaatacatc     60
```

-continued

```
ggacaactgg ggttttccgg cgacagctgc accgtgtggc gcaacaccga tagccgcctc    120

ggcaccacca gggaccaact cgccgaggtg ctttccacct tcgacgccat cctcatctcc    180

cccggtcccg gagaacccag ccaggctggc aagacgatgg aggtcatcga ggtcgctgcc    240

gagctgcgca tcccgctgtt cggcgtgtgc ctgggccacc aggccatcgg caagcacttc    300

ggcggggacg tggtgcgggc cgacgagctg ttccatggca agacctcgcc ggtggaacac    360

gacggaaccg gggtgctcgt ggacgtgccc agcccgttcc gcgtgacgcg ctaccactcc    420

ctgacggtgg atccggagac tctacctgac gagctcgttg tcacggcgcg cagtgactcc    480

gggatgatca tggcgatgcg gcatgtcgaa ctgccgatcc actccgtgca gtaccacccg    540

gagagcgtga tgacgcaata cgggcaccgg atgctcgcca actggttgaa cctggcgggg    600

gcagaggtac cggagcgcct ggtggaggag ctggagcggg aacagctggc cgtgacgggg    660

ctgatcagcg ccgaagcgtc gatgctgtag                                     690
```

<210> SEQ ID NO 189
<211> LENGTH: 654
<212> TYPE: DNA
<213> ORGANISM: Rhodococcus jostii

<400> SEQUENCE: 189

```
atgaggattc tcgtcgtcga caactacgac agcttcgtgt tcaacctggt ccagtacctc     60

ggacagctgg gaacgcgggc cgtggtctgg cgcaacgacg atccgaacct caccgggccc    120

gacgccgtcg cggcggcggc ggccgagttc gacggcattc tgctgagccc gggcccgggc    180

acaccgcagc gggcaggcgc gacgatggac ctggtcacgg cgtgtgccgc cgccaggacg    240

ccgctcctcg ggtgtgcct cggacaccag gcgatcgggg ccgcgttcgg cgccaccgtc    300

gaccgggcac ccgaactcct gcacggcaag accagcgtcg tccaccacac cggcgggggc    360

gttctcacgg gtctgcccga cccgttcacc gccacccgct accactcact gaccgtcctg    420

gaagacacca tcccggacga actcgaggtc accgcccaca ccgacagcgg catcgtgatg    480

gcgatgcggc accgcgaact gccgatccac ggcgtccagt tccacccgga gtccgtgctc    540

accgaaggcg ggcaccgcat gctcgccaac tggctcaccg tctgcggcga agccccgaag    600

gaatccctcg tcgccaccct cgagaccgag gtcgcgcaag cattgggcgc gtag          654
```

<210> SEQ ID NO 190
<211> LENGTH: 666
<212> TYPE: DNA
<213> ORGANISM: Rhodococcus erythropolis

<400> SEQUENCE: 190

```
atgaggattc tcgtcgtcga caactacgac agctttgtgt tcaacctggt gcagtacctc     60

ggccagctcg gaaccgaagc cgtggtctgg cgcaacgacg atccacaact gacggcagac    120

ctcgagggtg ccgtagctca gttcgacggc attctcctga gccctggccc cggaactccg    180

cagcgcgcgg gagcgacgat ggatctggtg aaggtctgcg ccgacaccaa gaccccgctg    240

ctcggcgtct gcctcggaca tcaggcgatc ggtgcggctt tcggcggaac cgtcgaccgc    300

gcgcccgaac tgcttcacgg caagacgagt ctggttcacc acaaggacgt cggcgtcctg    360

gccgggctgc ccgatccgtt caccgctacc cgctaccact cgctgacggt tctcgaggac    420

accattcccg aggaactcga ggtgaccgca cacaccgaga gcggcgtcgt gatggcgatg    480

cgtcaccgcg aactgccgat tcacggcgtc cagttccacc cagagtccgt actcactcaa    540
```

```
ggtgggcacc ggatgctcgc gaactggctc gcagtctgcg gtgaggcgcc cccggaaggg    600

ctcgtcgcag ccctcgaggc cgaggtcgcg tcggcgctcg gtggcgcatt gcccgcaatt    660

ctctga                                                               666


<210> SEQ ID NO 191
<211> LENGTH: 654
<212> TYPE: DNA
<213> ORGANISM: Rhodococcus opacus

<400> SEQUENCE: 191

atgaggattc tcgtcgtcga caactacgac agcttcgtgt tcaacctggt ccagtacctc     60

ggacagctgg gaacacgggc cgtggtctgg cgcaacgacg atccgaacct caccgggccc    120

gacgcgatcg cggccgcggc ggccgacttc gacggcatcc tcctgagccc cggccccggc    180

acaccgcagc gcgcaggcgc gacgatggac ctggtcacgg catgtgccgc ggccggcacg    240

ccgctcctcg gcgtgtgcct cggacaccag gcgatcggtg ccgcgttcgg cgcgaccgtc    300

gaccgggcgc ccgaactcct gcacggcaag accagcgtcg tccaccaccg cggcgagggt    360

gtcctcgcgg gtctgcccga cccgttcacc gccacgcggt accactcgct gaccgtcctg    420

gaagacacca tcccggacga actcgaggtc accgcgcaca ccgacagcgg catcgtcatg    480

gcgatgcggc accgcgaact gccgatccac ggcgtgcagt tccatccgga gtccgtgctc    540

accgagggcg ggcaccgcat gctcgccaac tggctcaccg tctgcggcga cgccccgaag    600

gaatccctcg tcgccacgct cgaagccgag gtcgcgcagg cactgggcgc gtag          654


<210> SEQ ID NO 192
<211> LENGTH: 639
<212> TYPE: DNA
<213> ORGANISM: Streptomyces coelicolor

<400> SEQUENCE: 192

gtgagcgcgc gcatcctcgt cgtcgacaac tacgacagct tcgtcttcaa cctggtccag     60

tacctctacc aactcggcgc cgagtgcgag gtgctgcgca acgacgaggt gtcgacggcc    120

cacgcccagg acggtttcga cggcgtcctg ctctcgcccg gcccgggcac gccggagcag    180

gcgggcgtct gcgtcgacat ggtccggcac tgcgcggcga ccggggtgcc ggtcttcggc    240

gtgtgcctgg gcatgcagtc gatgcaggtc gcgtacggcg gtgtggtgga ccgcgcgccg    300

gagctgctgc acggcaagac ctcgccggtg gagcacaccg gccggggcgt cttcgcgggg    360

ctgccctcgc cgttcacggc gacgcggtac cactcgctgg cggcggagcc ggccacggtg    420

ccggccgagc tggaggtgac ggcccgtacg ccggacggga tcgtgatggg cctgcgccac    480

cgggaactgc tcgtcgaggg cgtgcagttc cacccggagt cggtgctgac cgagcacggg    540

caccggatgc tggccaactg gctggtggag tgcggcgacc aggacgcggt ggcgaggtcg    600

gcggggctcg ccccggtggt gggcagggcc acggcgtga                           639


<210> SEQ ID NO 193
<211> LENGTH: 639
<212> TYPE: DNA
<213> ORGANISM: Streptomyces avermitilis

<400> SEQUENCE: 193

gtgagtacgc gcattctcgt tgtcgacaac tacgacagct tcgtcttcaa cctcgtccag     60

tacctgtacc agctgggtgc ggagtgcgag gtgctgcgca acgacgaggt gtcgaccgcg    120

cacgcccagg acggcttcgc cggcgtcctg ctctcgcccg gccccggtgc ccccgagcag    180
```

```
gcaggtgtct gcatcgacat ggtccggcac tgcgcggcga ccggcgtgcc cgtcttcggg    240

gtctgcctcg gcatgcagtc catgcaggtg gcgtacgggg gtgtggtgga ccgggcgccc    300

gagctgctgc acggcaagac ctcactcgtg gagcacacgg gcaagggcgt cttctcgggg    360

cttccctcgc ccttcacggc gacgcgctac cactcgctgg cggccgagcc ccggaccgtg    420

ccggacgagc tggaggtcac ggcccgcacg cacgacggga tcatcatggg gctccggcac    480

cgtgaactcc cggtcgaggg cgtgcagttc caccccgagt cggtgctgac cgagcacggt    540

caccggatgc tggccaactg gctggtggag tgcggcgaca cggatgccgt ggcgaggtcg    600

gcggggctcg ccccggtggt gggcagggcc acggcgtga                            639
```

```
<210> SEQ ID NO 194
<211> LENGTH: 639
<212> TYPE: DNA
<213> ORGANISM: Streptomyces griseus

<400> SEQUENCE: 194

gtgagcgcac gcgtcctcgt cgtggacaac tacgacagct tcgtcttcaa cctcgtccag     60

tacctctacc agctcggcgc cgagtgcgag gtgctgcgca acgacgaggt gacgcccgcc    120

cacgcgcagg acggcttcga cggggtcctc ctctccccgg ggcccggcac gcccgagcag    180

gccggcgtct gcgtcgagat ggtgcgccac tgcgcggaca ccggcgtccc ggtcttcggc    240

gtctgcctgg gcatgcagtc gatggcggtc gcgtacggcg gcgtcgtcga ccgggccccc    300

gaactgctgc acggcaagac ctccgccgtc acccacgagg gcaagggcgt cttcgccgga    360

ctgccctccc ccttcaccgc gacgcgctac cactcgctcg cggccgagcc cggcgcgctg    420

cccccggagc tggaggtcac cgcccgcacg gcggacggca tcatcatggg gctgcgccac    480

cgtgaccggg cggtggaggg cgtgcagttc caccccgagt ccgtgctcac cgagcacggc    540

cacctgatgc tcgccaactg gctggagcag tgcggagacc agggggccgt cgcgcggtcg    600

gcggggctcg cgccggtggt gggcaaggcc gccgcgtga                            639
```

```
<210> SEQ ID NO 195
<211> LENGTH: 639
<212> TYPE: DNA
<213> ORGANISM: Streptomyces lividans

<400> SEQUENCE: 195

gtgagcgcgc gcatcctcgt cgtcgacaac tacgacagct tcgtcttcaa cctggtccag     60

tacctctacc aactcggcgc cgagtgcgag gtgctgcgca acgacgaggt gtcgacggcc    120

cacgcccagg acggtttcga cggcgtcctg ctctcgcccg gcccgggcac gccggagcag    180

gcgggcgtct gcgtcgacat ggtccggcac tgcgcggcga ccggggtgcc ggtcttcggc    240

gtgtgcctgg gcatgcagtc gatgcaggtc gcgtacggcg gtgtggtgga ccgggcgccg    300

gagctgctgc acggcaagac ctcgccggtg gagcacaccg gccggggcgt cttcgcgggg    360

ctgccctcgc cgttcacggc gacgcggtac cactcgctgg cggcggagcc ggccacggtg    420

cgggccgagc tggaggtgac ggcccgtacg ccggacggga tcgtgatggg cctgcgtcac    480

cgggaactgc tcgtcgaggg agtgcagttc cacccggagt cggtgctgac cgagcacggg    540

caccggatgc tggccaactg gctggtggag tgcggcgacc aggacgcggt ggcgaggtcg    600

gcggggctcg ccccggtggt gggcagggcc acggcgtga                            639
```

```
<210> SEQ ID NO 196
```

<211> LENGTH: 642
<212> TYPE: DNA
<213> ORGANISM: Arthrobacter phenanthrenivorans

<400> SEQUENCE: 196

```
atgaccacaa ccaagatcct cgtggtggat aactacgaca gcttcgtcta caccctggtg     60

ggctacctcc aggaactcgg cgcggaaacc accgtggtcc gcaatgacga cgtcaccctg    120

gcggaagcca ttgaactggc gagtacccgg gatggcgtcc tcatctctcc cggtccggga    180

aaccccgcgg aggccggggt gtgcattgac ctgatcaggt ggtgcggcga gaacagcgtg    240

cccatgttcg gagtctgcct ggggcaccag gccctggcgg aggccttcgg cggcaaggtg    300

acgcacgcgc cggaactcat gcacggcaag acctcgcagg tccagcacat tggcacgagt    360

gtcttcgccg ggcttccctc cccgtcacc gccacgaggt atcactcgct ggccgccgtc    420

cgggaatcga tcccggacgt cctggaagtc acggcagaga ctgcatccgg tgtggtgatg    480

ggactccagc accgcactgc accactgtgc ggcgtgcagt tccaccccga gtccgtgctg    540

accgagggcg gctaccagat gctcggcaac tggcttgagt cgctgggcat gaagggcgcg    600

gcagcccgcg ctgccaagct gagcccgctc atccagcact ga                       642
```

<210> SEQ ID NO 197
<211> LENGTH: 639
<212> TYPE: DNA
<213> ORGANISM: Renibacterium salmoninarum

<400> SEQUENCE: 197

```
atgagtactc gcattttagt tattgataac tacgactctt tcgtctacac cttggtgggc     60

tacctgcagc agctaggggc cgagaccact gttatccgaa atgatgacgt cacccttgat    120

gaagctgtgg cactcgcgga agtccgggat ggggttttgc tttcgcccgg cccggggaat    180

ccagcggagg cgggcgtctg tatcgagcta attcgttggt gcgcgcagaa tagcaagcca    240

atgttcggtg tttgccttgg gcatcaggca ttagctgaag cattcggggg cgttgttgcg    300

cacgcgcctg aactaatgca cggcaagact tcacccgtgg agcacaatgg ggctgcgatg    360

tttgacggcg tgccgtctcc gttcaccgcg actcgatacc actccttggc ggcggttcgc    420

gagacaatcc cggacgagct tgagattact gcgcagacgg caagcggcgt cgtgatgggc    480

ctagcccatc ggaccgcccc actggtgggc gttcagttcc atcctgaatc ggtcctcacc    540

gaaggtggtt accggatgtt gggcaactgg ctggagtcct tgggcatggt gggagtggct    600

gaagcttcct cagaactcag cccactcatc caccgctga                            639
```

<210> SEQ ID NO 198
<211> LENGTH: 645
<212> TYPE: DNA
<213> ORGANISM: Bifidobacterium longum

<400> SEQUENCE: 198

```
atgaccgatt ccgcgcatat tttggtggtg gataactacg attccttcgt ctacacgatc     60

gtaggctatc tgcaaaccct tggcgccact gttgatgtgg tgcgtaacga cgctatcgac    120

ccagccgcgc cgggtgtact ggacggttac gatggcgtgc tgatttctcc cggccctggc    180

gctccggccg aatccggtgc cagtgaggat atgattcgcc tgtgcgcggc cagcggcgtg    240

ccgatgtttg gtgtgtgcct gggcttgcag gcgctcgctg aggtgtacgg ctgcactgtg    300

gaccatgcgc ccaccatcat gcatggcaag accagcttgg tggaacatat cgatgacgag    360

attttcgagg gcgtggccaa ccccatgacc gccacccgct accattcgtt ggccgtcgag    420
```

cccgattcgg tgccggatac gctggtggtt accgcgtgga cgcaaggcga ccacattatt 480
cagggcgtgc gtgtcaaggg caagccgatg tacgccgtgc aattccatcc cgaatccgtg 540
atgacccagg acggctaccg tctgctggcc aactggctca aggtctgcgg ccaagacaac 600
gccgtggcca agtccgccgg cctccagccc aaagttacga agtag 645

<210> SEQ ID NO 199
<211> LENGTH: 648
<212> TYPE: DNA
<213> ORGANISM: Bifidobacterium animalis

<400> SEQUENCE: 199
atgaccgatt ccgcgcgcat tctggtgata gacaactacg attccttcgt gtacacgatt 60
gtgggatatt tgaagacgct cggcgccacc gtgaccgtgg tgcgcaatga cgcgctcgac 120
ccgcacgaag atggtgtgct cgacgactac gacggcgtgc tcatctcacc cggaccgggg 180
gcgccgagcg agtcaggcgt gagcgaggac gtgattcgcc tgtgtgcaca gaccggcacg 240
cccatgttcg gtgtctgcct cggcatgcag gcgctcgccg aggtgtacgg ctgcaccgtg 300
agccacgcgc cgacgatcat gcatggcaag accagtctgg tagagcatgt ggatgatgag 360
atcttcgccg gcgtcgcgaa cccgatgact gcgacgcgct atcattcgct cgccgcggag 420
ccggattccg tgcccgacga gctgcaggtg accgcatgga ccgtggacga ccacattgtg 480
cagggtattc gccatcgcga actgccgttg ttcgccgtgc agttccaccc cgagtcggtg 540
ctcacgcagg atggctacag attgtttgcg aactggctgg ccgtgtgcgg tcaggagtct 600
gcggtcgaga agagcctcgg cctgcagccg aagctcgcgg ccgagtag 648

<210> SEQ ID NO 200
<211> LENGTH: 645
<212> TYPE: DNA
<213> ORGANISM: Bifidobacterium bifidum

<400> SEQUENCE: 200
atgacggatt cggcacgcat tgtggtggtg gacaattacg attcgttcgt atacaccatc 60
gttggatatc tgaaaacctt gggagcgacg gtcgatgtgg tgcgcaacga cgcaatagac 120
ccctcagatg cctctgtgct ggacgaatat gacggtgtgc ttatttcccc cggtccgggc 180
gctccggcgg attctggggc cagcgaggac gttattcggc tatgtgccaa gctcggcaag 240
cccatgttcg gtgtgtgcct cggcctgcag gcgctcgccg aggtgttcgg ctgcacggtc 300
agccacgcgc ccaccatcat gcacggcaaa accagtctcg tcgagcatat cgatgatgag 360
atcttcgccg gtgtcgccaa tccgatgacc gcgacccgat atcattcgct ggccgtcgag 420
cccgacaccg tgcctgatga cctggtcgtg acggcgtgga cgaaggatga ccatatcgtt 480
cagggcatca agcaccggtc gttgccgatg tatgcggtgc agttccatcc tgaatcggtg 540
atgacgcagg acggctaccg gctgctcgcc aactggctcg ccgtctgcgg gcagaccaac 600
gccgtggcca agtccatcgg tctgcagccc aaggtcaacc gctga 645

<210> SEQ ID NO 201
<211> LENGTH: 603
<212> TYPE: DNA
<213> ORGANISM: Synechococcus sp.

<400> SEQUENCE: 201
atgctgctgg tcatcgacaa ctacgacagc ttcaccttca acctggtgca gtacctcggt 60

-continued

```
gagctggctc cccattaccc catcgctgcg gatctccagg tgcaccgcaa cgacgccctc    120

accctggcgc agatccgaga actgaagccg gacgccatcc tgctctcgcc tggtccgggc    180

gatccggacc agtccggggt ctgcctggag gtgctccagg atctgtcccc caccactcca    240

acccttgggg tttgtctagg acatcaggcc atcgcccagg tgcatggcgg ccgcgtcgtg    300

cgtgccagcc aacaaatgca tggcaaaacc tcccccgtgc tgcacaacgg cgaaggggtg    360

ttcgccgggc tacctcagcc cctcacagcc acccgctacc actccctgat cgccgaacgc    420

agctcactgc cggactgctt ggaggtgacg gcctggctgg aggacggcac gatcatgggc    480

ctgcgccacc gtgaacatcg ccatcttcag gggtgcagt ttcatcccga gagtgtgttg    540

accgacgccg gccaccaact gctggccaac tttttgaagg aagccaacgg agaacgctgt    600

tag                                                                  603
```

<210> SEQ ID NO 202
<211> LENGTH: 576
<212> TYPE: DNA
<213> ORGANISM: Pantoea ananatis

<400> SEQUENCE: 202

```
atgttgctgc ttattgataa ctacgactcg tttacctgga acctctacca gtatttttgc     60

caactgggtg ctcaggttcg ggtagtaaga aatgatgcta ttacccttga tgagatgcgc    120

acgctgccgc tgactcattt ggtgatttct cccggcccct gcacgcccga tcagagcggt    180

atttccttgc aggccatccg ccattacgct ggccgtcttc ctgtactggg cgtttgcctg    240

ggccatcagg cgatagccca ggtttttggg gcgcagatcg ttcgcgctcg cgaggtaatg    300

cacggtaaaa cctcggcggt gcagcacaat ggttgtggcg tcttccgcgg tctgaatcag    360

ccgttgaccg ttacgcgcta ccattcactt attgtcaaaa cggaaacctt acctgatgcg    420

ttcgaggtga ccgcatggag cctgcgtaac ggccagccgg atgagattat ggggattcgc    480

cataaaacgc tcgcactgga aggcgtgcag tttcatccag agagcatcct cagtgaacag    540

ggacaccagc tgttggctaa tttcctgcac cagtaa                              576
```

<210> SEQ ID NO 203
<211> LENGTH: 1101
<212> TYPE: DNA
<213> ORGANISM: Corynebacterium glutamicum

<400> SEQUENCE: 203

```
atgagttctc cagtctcact cgaaaacgcg gcgtcaacca gcaacaagcg cgtcgtggct     60

ttccacgagc tgcctagccc tacagatctc atcgccgcaa acccactgac accaaagcag    120

gcttccaagg tggagcagga tcgccaggac atcgctgata tcttcgctgg cgacgatgac    180

cgcctcgttg tcgttgtggg accttgctca gttcacgatc ctgaagcagc catcgattac    240

gcaaaccgcc tggctccgct ggcaaagcgc cttgaccagg acctcaagat tgtcatgcgc    300

gtgtacttcg agaagcctcg caccaccgtc ggttggaagg gattgatcaa cgatcctcac    360

ctcaacgaaa cctacgacat cccagagggc ttgcgcattg cgcgcaaagt gcttatcgac    420

gttgtgaacc ttgatctccc agtcggctgc gaattcctcg aaccaaacag ccctcagtac    480

tacgccgaca ctgtcgcatg gggagcaatc ggcgctcgta ccaccgaatc tcaggtgcac    540

cgccagctgg cttctgggat gtctatgcca attggtttca agaacggaac tgacggaaac    600

atccaggttg cagtcgacgc ggtacaggct gcccagaacc cacacttctt cttcggaacc    660

tccgacgacg gcgcgctgag cgtcgtggag accgcaggca atagcaactc ccacatcatt    720
```

-continued

```
ttgcgcggcg gtacctccgg cccgaatcat gatgcagctt cggtggaggc cgtcgtcgag    780

aagcttggtg aaaacgctcg tctcatgatc gatgcttccc atgctaactc cggcaaggat    840

catatccgac aggttgaggt tgttcgtgaa atcgcagagc agatttctgg cggttctgaa    900

gctgtggctg gaatcatgat tgagtccttc ctcgttggtg gcgcacagaa ccttgatcct    960

gcgaaattgc gcatcaatgg cggtgaaggc ctggtgtacg gacagtctgt gaccgataag   1020

tgcatcgata ttgacaccac catcgatttg ctcgctgagc tggccgcagc agtaagggaa   1080

cgccgagcag cagccaagta a                                             1101
```

<210> SEQ ID NO 204
<211> LENGTH: 1233
<212> TYPE: DNA
<213> ORGANISM: Corynebacterium glutamicum

<400> SEQUENCE: 204

```
atgctaggca tgcttcgatg gactacagca ggtgaatccc acggccaggc gcttatcgcc     60

acggttgaac acatgccagc aggcgtgccc gtgactaaag atgaggtctc gtatcaattg    120

gcgcgccgac gccttggata tggtcgcggc gctcgcatga agtttgagca agacgcgttg    180

accttcctga ccggcatccg ccacggcctc actttgggta gccccatctc aatcatgatc    240

ggcaacactg agtgggataa gtggaccacc atcatgtcct ctgacgcttt ggacatggaa    300

gacccagaca acgttgcggc gatgtcttcg ggtcgcggtg caaaactgac tcgtccgcgt    360

ccaggccacg cagattacgc aggcatgctc aagtacggat tcgatgatgc ccgcaacgtg    420

ctggagcgtt cttcagcccg tgagacggca gctcgcgtgg cagcagcaac cgttgcgcgt    480

tccttcctcc gtgaaacctt gggcgtggag gtgctctctc acgtaatttc cattggtgcg    540

tccgagcctt acgtcggcgc ggagccaacc tttgcagata ttcaagcaat cgatgattcc    600

ccagttcgtg cattcggtaa agacgctgaa aaatccatga tcgcggaaat cgaggccgca    660

aagaaagccg gcgataccct cggtggcatc gtggaagtga ttgttgaagg cctacccatc    720

ggtttgggct cacacatttc tggcgaagat cgcctcgatg cgcagatcgc agctgcactc    780

atgggcattc aggccatcaa gggcgtggaa atcggtgacg gtttcgaaga agctcgtcga    840

cgtggctccg aagcccacga tgaagtgttc ctggatgaca acggcgtata ccgcaacacc    900

aaccgtgcag gtggcctcga aggcggcatg accaacggtg aaaccctgcg cgttcgtgct    960

ggcatgaagc caatttctac tgtgcctcgc gccctgaaaa ccattgatat ggaaaacggc   1020

aaggcagcaa ccggaatcca ccagcgttcc gacgtgtgcg ctgttccagc cgccggtgtc   1080

gttgcagaag caatggtcac cctggttctc gcccgcgcag tcctgcagaa attcggcggt   1140

gactccctga gtgaaaccaa gagcaacatt gacacctacc tcaaaaacat tgaggaacga   1200

atgaaattcg aaggtttaga ggatggagcg taa                                1233
```

<210> SEQ ID NO 205
<211> LENGTH: 573
<212> TYPE: DNA
<213> ORGANISM: Corynebacterium glutamicum

<400> SEQUENCE: 205

```
atggagcgta atgaagtgaa tgatcaaatt cacttagatc atcaatcaga tgacacctct     60

gaatgctcct gcccgatcgt ggttcttgtg ggtttgccag gagctggaaa atccaccatt    120

ggacgtcgat tagcgcgcgc cttaaacact gaactcgtcg actccgacga actcattgag    180
```

-continued

```
cgcgccaccg gaaaagcctg cggcgccgtg ttcagcgagc tcggcgagcc agccttccgc    240

gagctcgagg ccatccacgt ggccgaagca ctgaaatcct ccggagtggt gagcttggga    300

ggcggatctg tgctgacaga atccacccgt gaactgctca aaggccacga cgtggtctgg    360

atcgacgtgc cagtagaaga aggcatcagg cgcaccgcaa acgagcgttc ccgcccgtg    420

ctgcaagccg ccgaccccgc cgagcactac cgcaacctgg tgaaagtgcg caccccgttg    480

tacgaagagg tggcaaccta ccgacttcgc accaacaacc gcagccccca gcaagtggtg    540

gcagcagtgt tgcatcatct agaaatcgat taa                                573
```

<210> SEQ ID NO 206
<211> LENGTH: 1098
<212> TYPE: DNA
<213> ORGANISM: Corynebacterium glutamicum

<400> SEQUENCE: 206

```
atgagcgcag cgcagatttt caacaccgtc cacgtcaatg gatcttcccc ctatgatgtc     60

cacattggtt ccggcctcaa cgagctcatt gttcagcgcg cagcggaatc aggcgcggag    120

caggtagcga ttttgcacca gcccagcatg gatgacattg catccgagtt ggatgcagca    180

ctagtcgctg ctggtttgaa ggtcctgcac cttaatgttc ccgatgcgga aaacggcaag    240

tccttggaag tagcggggca gtgctgggat gaattgggtg gcgcagcatt cggccgccgc    300

gatatcgtca tcggacttgg tggcggtgct gccacagatc tcgcgggatt cgtcgctgct    360

gcgtggatgc gtggcgtgcg cgtcattcag gttccaacca ccttgttggc catggtggac    420

gctgcggtgg gcggcaagac tggcatcaat accgccgcag gcaagaacct tgtgggcgcg    480

ttccacgagc ctgacgcagt attcattgac accgaacgcc tagccaccct gcctgacgcg    540

gaaatcatcg cgggatccgc cgaaatcatc aaaactggtt tcatcgccga cccagaaatc    600

ctgcgccttt acgaaactga tcccgcagcc tgcctgaaga aagaagtcga aggctcccac    660

ctacctgaac tgatttggcg ctccgtcacc gtcaagggct ccgtggtcgg ccaagacctc    720

aaagaatcta gcctgcgcga aatcctcaac tacggacaca cctttgccca cgccgtcgaa    780

ctccgcgaaa acttccgctg gcgccacggc aatgccgttg cagtgggcat gatgttcatc    840

gctaacctct cccacaagct cgggcttatc gacgcgcccc tcctcgagcg ccaccgctca    900

atcctggcgg ccatcggtct gcccacttcc tacgaaggcg gagccttcga cgagctttac    960

gacggcatga cccgcgacaa gaaaaaccgc gacggcaaca tccgcttcgt cgcactgacc   1020

gccgtgggcg aggttacccg cattgagggg ccctcaaaac aagatttaca gagtgcttat   1080

gaggcaatca gccactaa                                                 1098
```

<210> SEQ ID NO 207
<211> LENGTH: 32
<212> TYPE: DNA
<213> ORGANISM: Artificial sequence
<220> FEATURE:
<223> OTHER INFORMATION: PCR primer

<400> SEQUENCE: 207

```
ctctctgcag tcgctcgtct cataaaaacg ac                                   32
```

<210> SEQ ID NO 208
<211> LENGTH: 52
<212> TYPE: DNA
<213> ORGANISM: Artificial sequence
<220> FEATURE:
<223> OTHER INFORMATION: PCR primer

<400> SEQUENCE: 208
ctctaagctt gtcgacggat ccgcatgctg tgtctcctct aaagattgta gg 52

<210> SEQ ID NO 209
<211> LENGTH: 30
<212> TYPE: DNA
<213> ORGANISM: Artificial sequence
<220> FEATURE:
<223> OTHER INFORMATION: PCR primer

<400> SEQUENCE: 209
ctctgcatgc ctgttttggc ggatgagaga 30

<210> SEQ ID NO 210
<211> LENGTH: 47
<212> TYPE: DNA
<213> ORGANISM: Artificial Sequence
<220> FEATURE:
<223> OTHER INFORMATION: PCR primer

<400> SEQUENCE: 210
ctctaagctt gtcgacggat ccaagagttt gtagaaacgc aaaaagg 47

<210> SEQ ID NO 211
<211> LENGTH: 1053
<212> TYPE: DNA
<213> ORGANISM: Corynebacterium kroppenstedtii

<400> SEQUENCE: 211
atgaattatc agaacgacga tttacgcatc aaagaaatca aagagttact tcctcctgtc 60
gcattgctgg aaaaattccc cgctactgaa aatgccgcga atacggttgc ccatgcccga 120
aaagcgatcc ataagatcct gaaaggtaat gatgatcgcc tgttggttgt gattggccca 180
tgctcaattc atgatcctgt cgcggcaaaa gagtatgcca ctcgcttgct ggcgctgcgt 240
gaagagctga aagatgagct ggaaatcgta atgcgcgtct attttgaaaa gccgcgtacc 300
acggtgggct ggaaagggct gattaacgat ccgcatatgg ataatagctt ccagatcaac 360
gacggtctgc gtatagcccg taaattgctg cttgatatta acgacagcgg tctgccagcg 420
gcaggtgagt ttctcgatat gatcacccca caatatctcg ctgacctgat gagctggggc 480
gcaattggcg cacgtaccac cgaatcgcag gtgcaccgcg aactggcatc agggcttttt 540
tgtccggtcg gcttcaaaaa tggcaccgac ggtacgatta aagtggctat cgatgccatt 600
aatgccgccg gtgcgccgca ctgcttcctg tccgtaacga aatgggggca ttcggcgatt 660
gtgaatacca gcggtaacgg cgattgccat atcattctgc gcggcggtaa agagcctaac 720
tacagcgcga agcacgttgc tgaagtgaaa gaagggctga acaaagcagg cctgccagca 780
caggtgatga tcgatttcag ccatgctaac tcgtccaaac aattcaaaaa gcagatggat 840
gtttgtgctg acgtttgcca gcagattgcc ggtggcgaaa aggccattat tggcgtgatg 900
gtggaaagcc atctggtgga aggcaatcag agcctcgaga gcggggagcc gctggcctac 960
ggtaagagca tcaccgatgc ctgcatcggc tgggaagata ccgatgctct gttacgtcaa 1020
ctggcgaatg cagtaaaagc gcgtcgcggg taa 1053

CORYNEFORM BACTERIAL TRANSFORMANT AND METHOD FOR PRODUCING 4-AMINOBENZOIC ACID OR SALT THEREOF USING SAME

TECHNICAL FIELD

The present invention relates a transformant of a coryneform bacterium that is subjected to a particular gene operation so that an ability of producing 4-aminobenzoic acid (this is also referred to as "para-aminobenzoic acid"; hereinafter it may be abbreviated as "4-ABA") or a salt of the same is imparted thereto, and to a process of efficiently producing 4-ABA using this transformant.

BACKGROUND ART

Against the backdrop of global warming and exhaustion of fossil resources, production of chemical products using renewable resources has been recognized to be an important measure with view to realizing a low-carbon society, as new industrial biorefinery, along with biofuel, and has attracted attention.

4-ABA has an amino group and a carboxyl group in the molecule, and as a polymer raw material, it is expected to have a great demand. Further, it has been widely used as a raw material for ultraviolet absorbers and pharmaceutical products.

Conventionally, 4-ABA has been synthesized through multi-phase reactions using petroleum as a raw material. More specifically, it is a pathway to synthesize p-nitrotoluene from toluene derived from petroleum, and synthesize 4-ABA via p-nitrobenzoic acid or p-toluidine. As strong acids are used and high temperature conditions are required in these reactions, massive energy is needed. From the viewpoint of breaking out of the dependence on fossil resources and reducing discharge of carbon dioxide, a 4-ABA producing process in which a biorefinery technique as an environmentally compatible process is used is earnestly desired.

On the other hand, many microorganisms have a pathway for production of 4-ABA as a precursor of folate. More specifically, it is a pathway that bacteria, yeasts, plants and the like have, for generating chorismate through an aromatic compound biosynthesis path, i.e., a so-called shikimate pathway, and thereafter, via 4-amino-4-deoxychorismate, synthesizing 4-ABA.

The conversion from chorismate to 4-amino-4-deoxychorismate is performed through a two-step reaction actually. A para-aminobenzoate synthase component II (PabA) extricates an ammonium group from glutamine, and a para-aminobenzoate synthase component I (PabB) synthesizes 4-amino-4-deoxychorismate from the ammonium group and chorismate. Further, 4-amino-4-deoxychorismate is converted to 4-ABA by a 4-amino-4-deoxychorismate lyase (PabC). *Escherichia coli* has a gene pabA, a gene pabB, and a gene pabC at different positions on the chromosome, whereas some microorganisms have pabAB, and others microorganisms have pabBC, as two-component protein.

Here, Non-patent Document 1 teaches the production of 4-ABA by using a transformant of yeast in which a gene abz1 (a homologous gene of pabAB) is excessively expressed. The 4-ABA productivity of this transformant, however, is 250 μM per 160 hours, which is extremely low, and is not practical.

Further, Patent Document 1 and Non-patent Document 2 report the production of 4-ABA by using a transformant obtained by introducing pabAB derived from *Corynebacterium efficiens* into the chromosome of *Escherichia coli*. The 4-ABA productivity thereof, however, is 35 mM (4.8 g/L) per 48 hours, which is low, and is unsatisfactory for the industrial production. Still further, Patent Document 1 reports the production of 4-ABA by using a transformant obtained by introducing pabAB derived from *Saccharopolyspora erythraea* into *Streptomyces lividans*, but the 4-ABA productivity was 1 mM or less per nine days.

Still further, Patent Document 2 discloses that pabA, pabB, and pabC can be excessively expressed in *Saccharomyces cerevisae, Kluyveromyces lactis, Aspergillus niger, Synechocystis*, or *Escherichia coli*, and thereby the conversion of 4-ABA from chorismate can be increased. Patent Document 2, however, only mentions the producibility of 4-ABA, but does not disclose an actual example of 4-ABA production.

PRIOR ART DOCUMENT

Patent Document

Patent Document 1: JP-A-2015-15
Patent Document 2: US 2014/0371418A1

Non-Patent Document

Non-patent Document 1: J Biotechnol (2013) 163:184-193
Non-patent Document 2: Biosci Biotechnol Biochem; 2014, Vol. 78, No. 2, 350-357

SUMMARY OF THE INVENTION

Problem to be Solved by the Invention

It is an object of the present invention to provide a microorganism that efficiently produces 4-ABA or a salt thereof using saccharides as a raw material, and a process of efficiently producing 4-ABA or a salt thereof using this microorganism.

Means to Solve the Problem

The present inventors have wholeheartedly carried out investigations in order to achieve the object described above and found the following:

(i) Regarding hosts for several transformants that have been reported to produce 4-ABA, the influences of 4-ABA on the growth of the same were compared, and it was found that *Corynebacterium glutamicum* had the highest resistance against 4-ABA, among *Corynebacterium glutamicum, Escherichia coli, Streptomyces lividans, Pseudomonas putida*, and *Saccharomyces cerevisae*. More specifically, *Corynebacterium glutamicum* can grow even under the presence of 4-ABA at a high concentration on the order of several hundred mM, and further, can consume saccharides at the same level as that in the case where 4-ABA is not present. In this way, *Corynebacterium glutamicum* has a high resistance against 4-ABA, and hence it is suitable for the production of 4-ABA or a salt of the same.

(ii) A transformant obtained by introducing, into a coryneform bacterium, a gene (pabC) that encodes a 4-amino-4-deoxychorismate lyase, a gene (pabB) that encodes a para-aminobenzoate synthase component I, and a gene (pabA) that encodes a para-aminobenzoate synthase component II can efficiently produce 4-ABA or a salt of the same, from saccharides.

(iii) A transformant obtained by introducing, into coryneform bacterium, a gene (pabB) that encodes a para-aminobenzoate synthase component I can efficiently produce 4-ABA or a salt of the same from saccharides in a medium that contains ammonium or an ammonium salt.

(iv) These transformants exhibit high 4-ABA production efficiency particularly in a case where it is subjected to aerobic reaction under conditions that are aerobic and under which the transformant substantially does not grow.

The present invention, which has been completed based on the above-described findings, provides a transformant, and a process of producing 4-ABA or a salt of the same, which are described below:

Item 1. A transformant having para-aminobenzoic acid producing ability, obtained by introducing a gene that encodes an enzyme having para-aminobenzoate synthase component I activity, into a coryneform bacterium as a host.

Item 2. The transformant according to Item 1, wherein the gene that encodes an enzyme having para-aminobenzoate synthase component I activity is a gene pabB.

Item 3. The transformant according to Item 1, wherein a gene that encodes an enzyme having para-aminobenzoate synthase component II activity is further introduced into the coryneform bacterium as a host.

Item 4. The transformant according to Item 3, wherein one of the following (i) and (ii) is introduced into the coryneform bacterium as a host: (i) the gene that encodes an enzyme having para-aminobenzoate synthase component I activity, which is a gene pabB, and the gene that encodes an enzyme having para-aminobenzoate synthase component II activity, which is a gene pabA; and (ii) a gene that encodes two-component enzyme having para-aminobenzoate synthase component I activity and para-aminobenzoate synthase component II activity, which is a gene pabAB.

Item 5. The transformant according to Item 1, wherein a gene that encodes an enzyme having 4-amino-4-deoxychorismate lyase activity is further introduced into the coryneform bacterium as a host.

Item 6. The transformant according to Item 5, wherein one of the following (i) and (ii) is introduced into the coryneform bacterium as a host: (i) the gene that encodes an enzyme having para-aminobenzoate synthase component I activity, which is a gene pabB, and the gene that encodes an enzyme having 4-amino-4-deoxychorismate lyase activity, which is a gene pabC; or (ii) a gene that encodes a two-component enzyme having para-aminobenzoate synthase component I activity and 4-amino-4-deoxychorismate lyase activity, which is a gene pabBC.

Item 7. The transformant according to Item 3, wherein a gene that encodes an enzyme having 4-amino-4-deoxychorismate lyase activity is further introduced into the coryneform bacterium as a host.

Item 8. The transformant according to Item 7, wherein one of the following (i) to (iv) is introduced into the coryneform bacterium as a host: (i) the gene that encodes an enzyme having para-aminobenzoate synthase component I activity, which is a gene pabB, the gene that encodes an enzyme having para-aminobenzoate synthase component II activity, which is a gene pabA, and the gene that encodes an enzyme having 4-amino-4-deoxychorismate lyase activity, which is a gene pabC; (ii) a gene that encodes a two-component enzyme having para-aminobenzoate synthase component I activity and 4-amino-4-deoxychorismate lyase activity, which is a gene pabBC, and the gene that encodes an enzyme having para-aminobenzoate synthase component II activity, which is a gene pabA; (iii) a gene that encodes two-component enzyme having para-aminobenzoate synthase component I activity and para-aminobenzoate synthase component II activity, which is a gene pabAB, and a gene that encodes an enzyme having 4-amino-4-deoxychorismate lyase activity, which is a gene pabC; and (iv) a gene that encodes two-component enzyme having para-aminobenzoate synthase component I activity and para-aminobenzoate synthase component II activity, which is a gene pabAB, and a gene that encodes a two-component enzyme having para-aminobenzoate synthase component I activity and 4-amino-4-deoxychorismate lyase activity, which is a gene pabBC.

Item 9. The transformant according to Item 4 or 8, wherein the gene pabAB is a gene of bacteria of the genus *Corynebacterium*, bacteria of the genus *Neuospora*, or bacteria of the genus *Rhodococcus.*

Item 10. The transformant according to Item 9, wherein the gene pabAB is a gene of *Corynebacterium callunae, Corynebacterium efficiens, Corynebacterium casei, Corynebacterium glutamicum, Corynebacterium ureicelerivorans, Corynebacterium argentoratense, Corynebacterium terpenotabidum, Neurospora crassa, Rhodococcus opacus*, or *Rhodococcus erythropolis.*

Item 11. The transformant according to Item 6 or 8, wherein the gene pabC is a gene of *Escherichia coli, Escherichia fergusonii, Saccharophagus degradans, Shewanella woodyi, Arthrobacter phenanthrenivorans, Anabaena variabilis, Azotobacter vinelandii, Ochrobactrum anthropi, Clostridium beijerinckii, Xenorhabdus bovienii, Bacillus pseudofirmus, Caulobacter crescentus, Synechococcus* sp., *Bacteroides thetaiotaomicron*, or *Ferrimonas balearica.*

Item 12. The transformant according to Item 6 or 8, wherein the gene pabBC is a gene of bacteria of the genus *Ralstonia*, the genus *Cupriavidus*, or the genus *Chromohalobacter.*

Item 13. The transformant according to Item 12, wherein the gene pabBC is a gene of bacteria of *Ralstonia eutropha, Cupriavidus taiwanensis*, or *Chromohalobacter* salexigens.

Item 14. The transformant according to Item 4 or 8, wherein the gene pabA is a gene of bacteria of the genus *Enterobacter.*

Item 15. The transformant according to Item 14, wherein the gene pabA is a gene of *Enterobacter cloacae.*

Item 16. The transformant according to any one of Items 1 to 15, wherein the coryneform bacterium as a host is a bacterium of the genus *Corynebacterium.*

Item 17. The transformant according to Item 16, wherein the bacterium of the genus *Corynebacterium* as a host is *Corynebacterium glutamicum.*

Item 18. The transformant according to Item 17, wherein *Corynebacterium glutamicum* as a host is *Corynebacterium glutamicum* R (FERM BP-18976), ATCC13032, or ATCC 13869.

Item 19. A *Corynebacterium glutamicum* transformant ANI198 (NITE BP-02188).

Item 20. A method for producing 4-aminobenzoic acid or a salt thereof, the process including the step of culturing the transformant according to any one of Items 1 to 19 in a reaction solution containing a saccharide so that the transformant produces 4-aminobenzoic acid or a salt thereof.

Item 21. The method according to Item 20, wherein the transformant is cultured under conditions that are aerobic and where the transformant does not grow.

Effect of the Invention

A transformant obtained by introducing, into a coryneform bacterium, a gene that encodes a para-aminobenzoate synthase component I, a gene that encodes a para-aminobenzoate synthase component II, and a gene that encodes a 4-amino-4-deoxychorismate lyase, can produce 4-ABA at a high concentration and at a high yield from saccharides such as glucose.

Further, in a case where 4-ABA is produced by culturing a transformant in a culture solution containing ammonium or an ammonium salt, it is not necessary to introduce a gene that encodes a para-aminobenzoate synthase component II, and a transformant obtained by introducing a gene that encodes a para-aminobenzoate synthase component I, or further introducing a gene that encodes a 4-amino-4-deoxychorismate lyase, into a coryneform bacterium, can produce 4-ABA at a high concentration and at a high yield from saccharides such as glucose.

Wth the present invention, therefore, 4-ABA, which is useful as a raw material for polymers, pharmaceutical products, ultraviolet absorbers and the like, can be mass-produced at a low cost, with environmental loads being reduced.

In the present invention, it is important to use a coryneform bacterium as a host, in terms of the efficiency of the production of 4-ABA or salts thereof. It can be therefore considered that in the present invention, the combination of a coryneform bacterium as a host and a particular transgene described above is important.

Generally, since the growth of a microorganism is inhibited by cytotoxicity of an aromatic compound such as 4-ABA, it was difficult to manufacture 4-ABA by using microorganisms. A coryneform bacterium, however, has a significantly high resistance against 4-ABA, and by using a transformant of the present invention, it is possible to produce 4-ABA or a salt thereof at a high concentration. Further, a coryneform bacterium, unlike *Escherichia coli*, does not generate endotoxin, which makes it unnecessary to worry about residues of endotoxin in products. Still further, in the case of the coryneform bacterium, the reaction of generating 4-ABA or a salt thereof proceeds even under conditions where the growth of the coryneform bacteria is limited. Saccharides as raw materials therefore are not consumed for growth of the same, and this makes the yield of 4-ABA or a salt thereof higher, and makes it unnecessary to add, to a culture solution, substances that are generally required in growth of microorganisms, such as aromatic amino acids or 4-hydroxybenzoic acid. Thereby, the production costs can be reduced accordingly.

MODE FOR CARRYING OUT THE INVENTION

Figure 1:
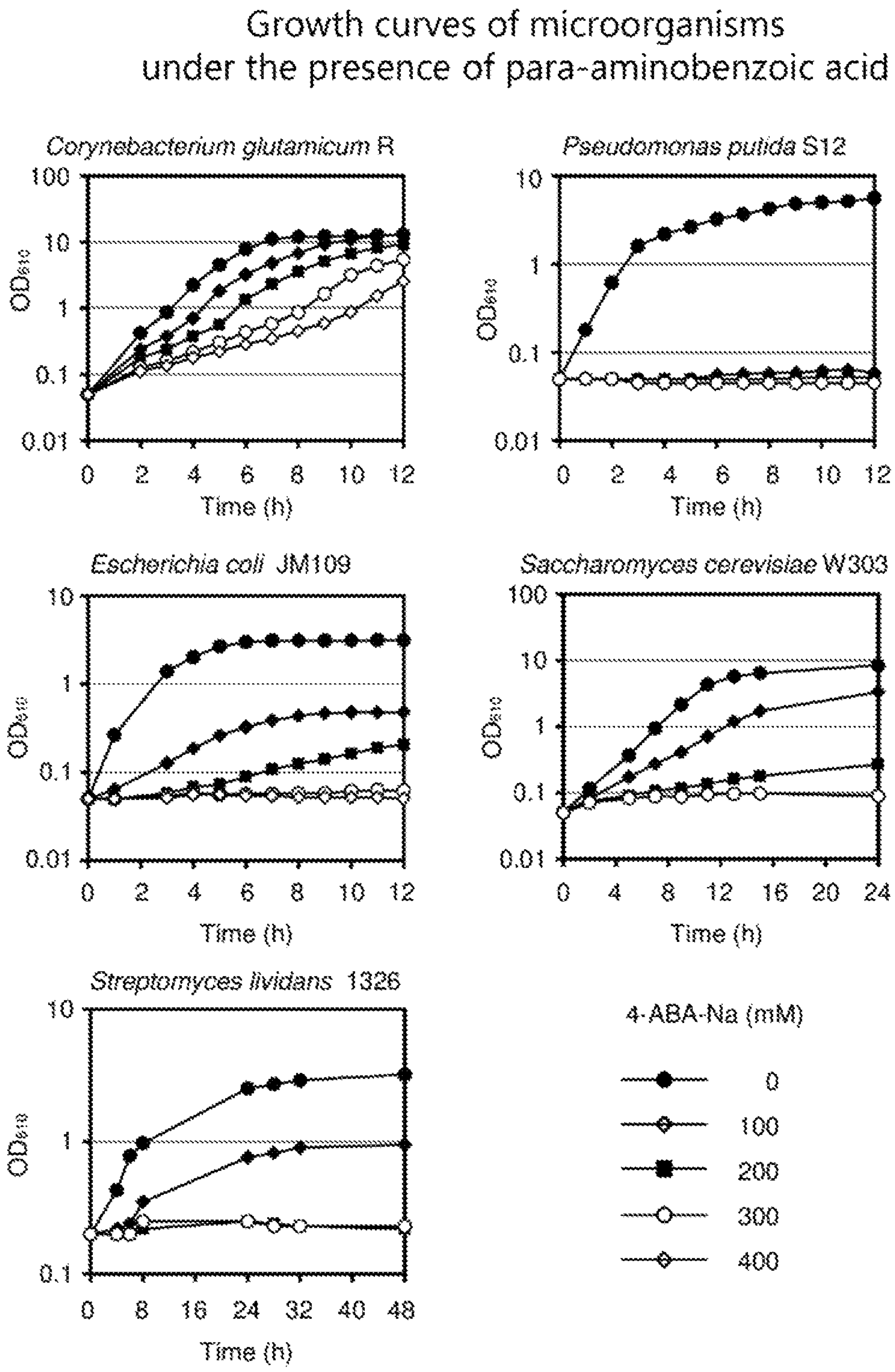
FIG. 1 illustrates growth curves of microorganisms of various types including *Corynebacterium glutamicum* under the presence of para-aminobenzoic acid.

The following describes the present invention in detail.

(1) Transformant Having 4-ABA Producing Ability

Host

In the present invention, a coryneform bacterium is used as a host.

The coryneform bacteria are a group of microorganisms defined in Bergey's Manual of Determinative Bacteriology, Vol. 8, 599 (1974), and are not particularly limited as long as they grow under normal aerobic conditions. The specific examples include the genus *Corynebacterium*, the genus *Brevibacterium*, the genus *Arthrobacter*, the genus *Mycobacterium* and the genus *Micrococcus*. Among the coryneform bacteria, the genus *Corynebacterium* is preferred.

Examples of the genus *Corynebacterium* include *Corynebacterium glutamicum, Corynebacterium efficiens, Corynebacterium ammoniagenes, Corynebacterium halotolerance*, and *Corynebacterium alkanolyticum.*

Among them, *Corynebacterium glutamicum* is preferred for safety and high 4-ABA production. Examples of preferred strains include *Corynebacterium glutamicum* R (FERM BP-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233(FERM BP-1497), MJ-233AB-41(FERM BP-1498). These strains are internationally deposited under the Budapest Treaty, and available to the public.

Among them, strains R (FERM BP-18976), ATCC13032, and ATCC13869 are preferred.

According to molecular biological classification, names of some species of coryneform bacteria, such as *Brevibacterium flavum, Brevibacterium lactofermentum, Brevibacterium divaricatum*, and *Corynebacterium lilium* are standardized to *Corynebacterium glutamicum* [Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int J Syst Bacteriol. 41:255-260. (1991), Kazuo Komagata et al., "Classification of the coryneform group of bacteria", Fermentation and Industry, 45:944-963 (1987)].

Examples of the genus *Brevibacterium* include *Brevibacterium ammoniagenes* (for example, ATCC6872).

Examples of the genus *Arthrobacter* include *Arthrobacter globiformis* (for example, ATCC8010, ATCC4336, ATCC21056, ATCC31250, ATCC31738, ATCC35698).

Examples of the genus *Mycobacterium* include *Mycobacterium bovis* (for example, ATCC19210, ATCC27289).

Examples of the genus *Micrococcus* include *Micrococcus freudenreichii* (for example, Strain No. 239 (FERM P-13221)), *Micrococcus leuteus* (for example, Strain No. 240 (FERM P-13222)), *Micrococcus ureae* (for example, IAM1010), and *Micrococcus roseus* (for example, IF03764).

These strains are internationally deposited under the Budapest Treaty, and available to the public.

The coryneform bacteria may be, let alone a wild type, a mutant thereof or an artificial recombinant thereof. Examples thereof include strain in which a gene such as lactate dehydrogenase (LDH), phosphoenolpyruvate carboxylase, or malate dehydrogenase is disrupted. Among them, preferred is a disruptant in which a lactate dehydrogenase gene is disrupted. In the disruptant, the lactate dehydrogenase gene is disrupted and the metabolic pathway from pyruvic acid to lactic acid is blocked. Particularly preferred is a disruptant of *Corynebacterium glutamicum*, especially the strain R (FERM BP-18976) in which the lactate dehydrogenase gene is disrupted.

Such a disruptant can be prepared based on a conventional gene engineering process. Such a lactate dehydrogenase disruptant and the preparation process thereof are described in WO 2005/010182A1, for example.

Figure 2:
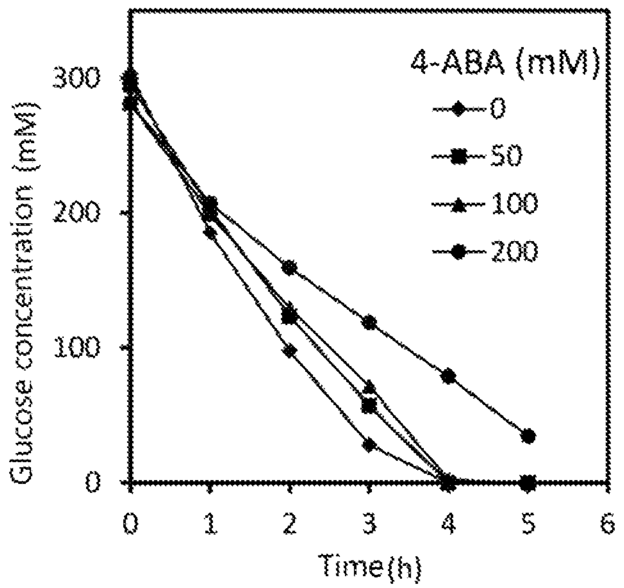
FIG. 2 illustrates changes with time of glucose concentration in reaction solution of a wild strain of *Corynebacterium glutamicum* under the presence of para-aminobenzoic acid.

The inventors found that, as shown in FIG. 2, coryneform bacteria have extremely higher 4-ABA resistance compared with other bacteria. In this regard, coryneform bacteria are suitable for the 4-ABA production by the process of the present invention.

Transgene

In one aspect of the present invention, a gene that encodes an enzyme having a para-aminobenzoate synthase component I activity, a gene that encodes an enzyme having a para-aminobenzoate synthase component II activity, and a gene that encodes an enzyme having a 4-amino-4-deoxychorismate lyase activity, are introduced into a coryneform bacterium.

The para-aminobenzoate synthase component I catalyzes a reaction of generating 4-amino-4-deoxychorismate from chorismate and ammonium. Further, the para-aminobenzoate synthase component II catalyzes a reaction of generating glutamic acid and ammonium from glutamine. Further, the 4-amino-4-deoxychorismate lyase catalyzes a reaction of generating 4-aminobenzoic acid (4-ABA or a salt thereof) and pyruvate from 4-amino-4-deoxychorismate.

By introducing the three genes described above into a coryneform bacterium, therefore, a transformant that efficiently generates 4-ABA or a salt thereof from chorismate is obtained.

In a case where ammonium or an ammonium salt is contained in the reaction solution or the culture solution, however, it is not necessary to introduce the gene that encodes an enzyme having para-aminobenzoate synthase component II activity. In such a case, the para-aminobenzoate synthase component I uses ammonium or an ammonium salt in the reaction solution or the culture solution to generate 4-amino-4-deoxychorismate from chorismate.

Further, since a coryneform bacterium has a 4-amino-4-deoxychorismate lyase gene on its chromosome, the gene that encodes an enzyme having a 4-amino-4-deoxychorismate lyase activity may not necessarily be introduced. It is however better to introduce the gene that encodes an enzyme having a 4-amino-4-deoxychorismate lyase activity so that a transformant that produces 4-ABA or a salt thereof more efficiently.

The transformant of another aspect of the present invention is obtained by introducing the gene that encodes an enzyme having para-aminobenzoate synthase component I activity into a coryneform bacterium. Further, it is possible to introduce the gene that encodes an enzyme having 4-amino-4-deoxychorismate lyase activity in addition to the gene that encodes an enzyme having para-aminobenzoate synthase component I activity. Still further, it is possible to introduce the gene that encodes an enzyme having para-aminobenzoate synthase component II activity in addition to the gene that encodes an enzyme having para-aminobenzoate synthase component I activity.

Examples of the gene that encodes an enzyme having para-aminobenzoate synthase component I activity include pabB, examples of the gene that encodes an enzyme having para-aminobenzoate synthase component II activity include pabA, and examples of the gene that encodes an enzyme having a 4-amino-4-deoxychorismate lyase activity include pabC.

There are also two-component enzymes or two-function enzymes that have two activities among the activities of the para-aminobenzoate synthase component I, the para-aminobenzoate synthase component II, and the 4-amino-4-deoxychorismate lyase. Examples of the two-component enzyme include a two-component enzyme (PabAB) having the para-aminobenzoate synthase component I activity and the para-aminobenzoate synthase component II activity; and a two-component enzyme (PabBC) having the para-aminobenzoate synthase component I activity and the 4-amino-4-deoxychorismate lyase activity.

Examples of the gene introduced into a coryneform bacterium, or the combination of such genes, include the following:

(i) pabB
(ii) pabB and pabC
(iii) pabBC
(iv) pabB and pabA
(v) pabAB
(vi) pabB, pabA, and pabC
(vii) pabAB and pabC
(viii) pabA and pabBC
(ix) pabAB and pabBC Though the origin of each gene is not limited particularly, examples of the gene include genes of the following microorganisms:

Examples of pabB include genes of bacteria of the genus *Corynebacterium* (in particular, *Corynebacterium kroppenstedtii, Corynebacterium resistens, Corynebacterium falsenii*), bacteria of the genus *Bacillus* (in particular, *Bacillus subtilis, Bacillus amyloliquefaciens, Bacillus thuringiensis*), bacteria of the genus *Escherichia* (in particular, *Escherichia coli, Escherichia fergusonii*), bacteria of the genus *Streptomyces* (in particular, *Streptomyces coelicolor, Streptomyces griseus, Streptomyces lividans*), bacteria of the genus *Salmonella* (in particular, *Salmonella enterica, Salmonella bongori*), bacteria of the genus *Pseudomonas* (in particular, *Pseudomonas aeruginosa, Pseudomonas putida, Pseudomonas fluorescens*), bacteria of the genus *Yersinia* (in particular, *Yersinia pestis, Yersinia pseudotuberculosis*), bacteria of the genus *Enterobacter* (in particular, *Enterobacter* sp., *Enterobacter cloacae*), *Mycobacterium smegmatis, Klebsiella pneumoniae, Xenorhabdus bovienii, Pantoea ananatis, Providencia stuartii, Azotobacter vinelandii, Acinetobacter baumannii, Shewanella woodyi, Zymomonas mobilis, Clostridium perfringens*, and *Saccharopolyspora erythraea.*

In particular, genes of *Bacillus subtilis, Escherichia coli, Streptomyces coelicolor, Enterobacter cloacae, Mycobacterium smegmatis, Klebsiella pneumoniae, Xenorhabdus bovienii, Pantoea ananatis*, and *Providencia stuartii* are preferable, among which genes of *Escherichia coli, Enterobacter cloacae, Pantoea ananatis*, and *Providencia stuartii* are more preferable.

Examples of pabB of *Corynebacterium kroppenstedtii, Corynebacterium resistens, Corynebacterium falsenii, Bacillus subtilis, Bacillus amyloliquefaciens, Bacillus thuringiensis, Escherichia coli, Escherichia fergusonii, Streptomyces coelicolor, Streptomyces griseus, Streptomyces lividans, Salmonella enterica, Salmonella bongori, Pseudomonas aeruginosa, Pseudomonas putida, Pseudomonas fluorescens, Yersinia pestis, Yersinia pseudotuberculosis, Enterobacter* sp., *Enterobacter cloacae, Mycobacterium smegmatis, Klebsiella pneumoniae, Xenorhabdus bovienii, Pantoea ananatis, Providencia stuartii, Azotobacter vinelandii, Acinetobacter baumannii, Shewanella woodyi, Zymomonas mobilis, Clostridium perfringens, Saccharopolyspora erythraea* include genes consisting of base sequences represented by SEQ ID NO. 1, SEQ ID NO. 132, SEQ ID NO. 133, SEQ ID NO. 134, SEQ ID NO. 135, SEQ ID NO. 136, SEQ ID NO. 137, SEQ ID NO. 138, SEQ ID NO. 139, SEQ ID NO. 140, SEQ ID NO. 141, SEQ ID NO.

142, SEQ ID NO. 143, SEQ ID NO. 144, SEQ ID NO. 145, SEQ ID NO. 146, SEQ ID NO. 147, SEQ ID NO. 148, SEQ ID NO. 149, SEQ ID NO. 150, SEQ ID NO. 151, SEQ ID NO. 152, SEQ ID NO. 153, SEQ ID NO. 154, SEQ ID NO. 155, SEQ ID NO. 156, SEQ ID NO. 157, SEQ ID NO. 158, SEQ ID NO. 159, SEQ ID NO. 160, or SEQ ID NO. 161.

Examples of pabC include genes of *Escherichia coli, Escherichia fergusonii, Saccharophagus degradans, Shewanella woodyi, Arthrobacter phenanthrenivorans, Anabaena variabilis, Azotobacter vinelandii, Ochrobactrum anthropi, Clostridium beijerinckii, Xenorhabdus bovienii, Bacillus pseudofirmus, Caulobacter crescentus, Synechococcus* sp., *Bacteroides thetaiotaomicron*, and *Ferrimonas balearica*. In particular, genes of *Xenorhabdus bovienii, Anabaena variabilis, Bacillus pseudofirmus, Escherichia coli*, and *Ochrobactrum anthropi* are preferable, among which genes of *Xenorhabdus bovienii, Anabaena variabilis*, and *Escherichia coli* are more preferable.

Examples of pabC of *Escherichia coli, Escherichia fergusonii, Saccharophagus degradans, Shewanella woodyi, Arthrobacter phenanthrenivorans, Anabaena variabilis, Azotobacter vinelandii, Ochrobactrum anthropi, Clostridium beijerinckii, Xenorhabdus bovienii, Bacillus pseudofirmus, Caulobacter crescentus, Synechococcus* sp., *Bacteroides thetaiotaomicron*, and *Ferrimonas balearica* are genes consisting of base sequences represented by SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, or SEQ ID NO. 16, respectively.

Examples of pabA include genes of bacteria of the genus *Escherichia* (in particular, *Escherichia coli, Escherichia fergusonii*), bacteria of the genus *Salmonella* (in particular, *Salmonella enterica, Salmonella bongori*), bacteria of the genus *Yersinia* (in particular, *Yersinia pestis, Yersinia pseudotuberculosis*), bacteria of the genus *Enterobacter* (in particular, *Enterobacter cloacae*), bacteria of the genus *Klebsiella* (in particular, *Klebsiella pneumoniae*), bacteria of the genus *Xenorhabdus* (in particular, *Xenorhabdus bovienii*), bacteria of the genus *Providencia* (in particular, *Providencia stuartii*), bacteria of the genus *Shewanella* (in particular, *Shewanella woodyi*), bacteria of the genus *Zymomonas* (in particular, *Zymomonas mobilis*), bacteria of the genus *Bacillus* (in particular, *Bacillus subtilis, Bacillus thuringiensis*), bacteria of the genus *Lactococcus* (in particular, *Lactococcus lactis*), bacteria of the genus *Mycobacterium* (in particular, *Mycobacterium bovis, Mycobacterium smegmatis*), bacteria of the genus *Corynebacterium* (in particular, *Corynebacterium urealyticum, Corynebacterium kroppenstedtii, Corynebacterium resistens, Corynebacterium variabile, Corynebacterium falsenii*), bacteria of the genus *Rhodococcus* (in particular, *Rhodococcus jostii, Rhodococcus erythropolis, Rhodococcus opacus*), bacteria of the genus *Streptomyces* (in particular, *Streptomyces coelicolor, Streptomyces avermitilis, Streptomyces griseus, Streptomyces lividans*), bacteria of the genus *Arthrobacter* (in particular, *Arthrobacter phenanthrenivorans*), bacteria of the genus *Renibacterium* (in particular, *Renibacterium salmoninarum*), bacteria of the genus *Bifidobacterium* (in particular, *Bifidobacterium longum, Bifidobacterium animalis, Bifidobacterium bifidum*), *Synechococcus* sp., and bacteria of the genus *Pantoea* (in particular, *Pantoea ananatis*). In particular, genes of *Escherichia coli, Providencia stuartii, Enterobacter cloacae*, and *Pantoea ananatis* are preferable, among which genes of *Enterobacter cloacae*, and *Escherichia coli* are more preferable.

Examples of pabA of *Escherichia coli, Escherichia fergusonii, Salmonella enterica, Salmonella bongori, Yersinia pestis, Yersinia pseudotuberculosis, Enterobacter cloacae, Klebsiella pneumoniae, Xenorhabdus bovienii, Providencia stuartii, Shewanella woodyi, Zymomonas mobilis, Bacillus subtilis, Bacillus thuringiensis, Lactococcus lactis, Mycobacterium bovis, Mycobacterium smegmatis, Corynebacterium urealyticum, Corynebacterium kroppenstedtii, Corynebacterium resistens, Corynebacterium variabile, Corynebacterium falsenii, Rhodococcus jostii, Rhodococcus erythropolis, Rhodococcus opacus, Streptomyces coelicolor, Streptomyces avermitilis, Streptomyces griseus, Streptomyces lividans, Arthrobacter phenanthrenivorans, Renibacterium salmoninarum, Bifidobacterium longum, Bifidobacterium animalis, Bifidobacterium bifidum, Synechococcus* sp., and *Pantoea ananatis* include genes consisting of base sequences represented by SEQ ID NO. 168, SEQ ID NO. 169, SEQ ID NO. 170, SEQ ID NO. 171, SEQ ID NO. 172, SEQ ID NO. 173, SEQ ID NO. 17, SEQ ID NO. 174, SEQ ID NO. 175, SEQ ID NO. 176, SEQ ID NO. 177, SEQ ID NO. 178, SEQ ID NO. 179, SEQ ID NO. 180, SEQ ID NO. 181, SEQ ID NO. 182, SEQ ID NO. 183, SEQ ID NO. 184, SEQ ID NO. 185, SEQ ID NO. 186, SEQ ID NO. 187, SEQ ID NO. 188, SEQ ID NO. 189, SEQ ID NO. 190, SEQ ID NO. 191, SEQ ID NO. 192, SEQ ID NO. 193, SEQ ID NO. 194, SEQ ID NO. 195, SEQ ID NO. 196, SEQ ID NO. 197, SEQ ID NO. 198, SEQ ID NO. 199, SEQ ID NO. 200, SEQ ID NO. 201, or SEQ ID NO. 202.

Examples of pabBC include genes of the genus *Ralstonia* (preferably, *Ralstonia eutropha*), the genus *Cupriavidus* (preferably, *Cupriavidus taiwanensis*), the genus *Chromohalobacter* (preferably, *Chromohalobacter salexigens*), the genus *Pandoraea* (preferably, *Pandoraea pnomenusa*), the genus *Lactococcus* (preferably, *Lactococcus lactis*), or the genus *Streptococcus* (preferably, *Streptococcus pneumoniae, Streptococcus thermophilus*).

In particular, genes of *Ralstonia eutropha, Cupriavidus taiwanensis*, and *Chromohalobacter salexigens* are preferable, among which genes of *Ralstonia eutropha* are more preferable.

Examples of pabBC of *Ralstonia eutropha, Cupriavidus taiwanensis, Chromohalobacter salexigens, Pandoraea pnomenusa, Lactococcus lactis, Streptococcus pneumoniae*, and *Streptococcus thermophilus* include genes consisting of base sequences represented by SEQ ID NO. 129, SEQ ID NO. 162, SEQ ID NO. 163, SEQ ID NO. 164, SEQ ID NO. 165, SEQ ID NO. 166, or SEQ ID NO. 167.

Examples of pabAB include genes of bacteria of the genus *Corynebacterium* (in particular, *Corynebacterium callunae, Corynebacterium efficiens, Corynebacterium casei, Corynebacterium glutamicum, Corynebacterium ureicelerivorans, Corynebacterium argentoratense, Corynebacterium terpenotabidum*), bacteria of the genus *Neuospora* (in particular, *Neurospora crassa*), or bacteria of the genus *Rhodococcus* (in particular, *Rhodococcus opacus*, and *Rhodococcus erythropolis*).

In particular, genes of *Corynebacterium callunae, Corynebacterium efficiens, Corynebacterium casei, Corynebacterium glutamicum, Rhodococcus opacus*, and *Neurospora crassa* are preferable, among which genes of *Corynebacterium callunae* and *Corynebacterium efficiens* are more preferable.

Examples of pabAB of *Corynebacterium callunae, Corynebacterium efficiens, Corynebacterium casei, Corynebacterium glutamicum, Corynebacterium ureicelerivorans, Corynebacterium argentoratense, Corynebacterium terpenotabidum, Neurospora crassa, Rhodococcus opacus*, and

*Rhodococcus erythropolis* include genes consisting of base sequences represented by SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, and SEQ ID NO. 27.

Regarding an analog of pabB, a DNA that hybridizes to a DNA which consists of a base sequence complementary to any one of SEQ ID NOs: 1, 132 to 161 under stringent conditions, and encodes a polypeptide having para-aminobenzoate synthase component I activity, can be used as well.

Regarding an analog of pabC, a DNA that hybridizes to a DNA which consists of a base sequence complementary to any one of SEQ ID NOs: 2 to 16 under stringent conditions, and encodes a polypeptide having 4-amino-4-deoxychorismate lyase activity, can be used as well.

Regarding an analog of pabA, a DNA that hybridizes to a DNA which consists of a base sequence complementary to any one of SEQ ID NOs: 17, 168 to 202 under stringent conditions, and encodes a polypeptide having para-aminobenzoate synthase component II activity, can be used as well.

Regarding an analog of pabBC, a DNA that hybridizes to a DNA which consists of a base sequence complementary to any one of SEQ ID NOs: 129, 162 to 167 under stringent conditions, and encodes a polypeptide having para-aminobenzoate synthase component I activity and 4-amino-4-deoxychorismate lyase activity, can be used as well.

Regarding an analog of pabAB, a DNA that hybridizes to a DNA which consists of a base sequence complementary to any one of SEQ ID NOs: 18 to 27 under stringent conditions, and encodes a polypeptide having para-aminobenzoate synthase component I activity and para-aminobenzoate synthase component II activity, can be used as well.

In the present invention, "stringent conditions" means conditions in which hybridization is performed in a hybridization solution at a salt concentration of 6×SSC at 50 to 60° C. for 16 hours and then washing with a solution at a salt concentration of 0.1×SSC is performed.

Further, regarding an analog of pabB, a DNA which consists of a base sequence having 90% or more, preferably 95% or more, more preferably 98% or more of identity with any one of SEQ ID NOs: 1, 132 to 161, and encodes a polypeptide having para-aminobenzoate synthase component I activity can be used as well.

Further, regarding an analog of pabC, a DNA which consists of a base sequence having 90% or more, preferably 95% or more, more preferably 98% or more of identity with any one of SEQ ID NOs: 2 to 16, and encodes a polypeptide having 4-amino-4-deoxychorismate lyase activity can be used as well.

Regarding an analog of pabA, a DNA which consists of a base sequence having 90% or more, preferably 95% or more, more preferably 98% or more of identity with any one of SEQ ID NOs: 17, 168 to 202, and encodes a polypeptide having para-aminobenzoate synthase component II activity can be used as well.

Regarding an analog of pabBC, a DNA which consists of a base sequence having 90% or more, preferably 95% or more, more preferably 98% or more of identity with any one of SEQ ID NOs: 129, 162 to 167, and encodes a polypeptide having para-aminobenzoate synthase component I activity and 4-amino-4-deoxychorismate lyase activity can be used as well.

Regarding an analog of pabAB, a DNA which consists of a base sequence having 90% or more, preferably 95% or more, more preferably 98% or more of identity with any one of SEQ ID NOs: 18 to 27, and encodes a polypeptide having para-aminobenzoate synthase component I activity and para-aminobenzoate synthase component II activity can be used as well.

In the present invention, the identities of base sequences were calculated using GENETYX Ver. 8 (made by Genetyx Corporation).

The para-aminobenzoate synthase component I activity can be measured in the following manner.

50 mM triethanolamine (pH 8.5), 5% glycerol, 5 mM dithiothreitol (DTT), 5 mM $MgCl_2$, 250 mM $NH_4Cl$, 0.1 mM chorismic acid barium salt, PabB (20U) are prepared, and a total liquid amount of 3 ml of the same is subjected to reaction. After the reaction starts at 33° C., 0.5 ml of the same is sampled at every 2 minutes, and 0.1 ml of 1N HCl is added so that the reaction is stopped. 4-aminodeoxychorismate (ADC) thus produced is separated by using HPLC (Prominence) manufactured by Shimadzu Corporation, and as a column, Cosmosil packed column 5C18-AR-II (4.6×250 mm, manufactured by Nacalai Tesque). The detection of the same is performed with a wavelength of 270 nm, so that the enzyme activity is calculated from an initial rate.

Further, in a case where PabA is present together, 20 U of PabA is added and caused to react in the same manner.

The para-aminobenzoate synthase component II activity can be measured in the following manner.

50 mM Tris-HCl (pH 7.5), 5% glycerol, 5 mM DTT, 5 mM $MgCl_2$, 250 mM $NH_4Cl$, 10 mM L-glutamine, PabA (20U) are prepared, and a total liquid amount of 3 ml of the same is subjected to reaction. After the reaction starts at 33° C., 0.5 ml of the same is sampled at every 2 minutes, and 0.1 ml of 1N HCl is added so that the reaction is stopped. After L-glutamic acid as a reaction product is separated by using HPLC (Prominence) manufactured by Shimadzu Corporation, and as a column, Shim-Pack Amino-Na, 6.0×100 mm, manufactured by Shimadzu Corporation, it is labeled with O-phthalaldehyde, subjected to fluorescence detection, and quantitatively determined, so that the enzyme activity is calculated from an initial rate.

Further, in a case where it is coupled with PabB and measured, the following method is used. 50 mM Tris-HCl (pH 7.5), 5% glycerol, 5 mM DTT, 5 mM $MgCl_2$, 250 mM $NH_4Cl$, 0.1 mM chorismic acid barium salt, 10 mM L-glutamine, PabA (20U), and PabB (20U) are prepared, and a total liquid amount of 3 ml of the same is subjected to reaction. After the reaction starts at 33° C., 0.5 ml of the same is sampled at every 2 minutes, and 0.1 ml of 1N HCl is added so that the reaction is stopped. ADC thus produced is separated by using HPLC (Prominence) manufactured by Shimadzu Corporation, and as a column, Cosmosil packed column 5C18-AR-II (4.6×250 mm, manufactured by Nacalai Tesque), and the detection of ADC is performed with a wavelength of 270 nm, so that the enzyme activity is calculated from an initial rate.

The 4-amino-4-deoxychorismate lyase activity is measured by utilizing the coupling reaction with PabB in the following manner. 50 mM Tris-HCl (pH 7.5), 5% glycerol, 5 mM DTT, 5 mM $MgCl_2$, 250 mM $NH_4Cl$, 0.1 mM chorismic acid barium salt, PabB (200U), and PabC (20U) are prepared, and a total liquid amount of 3 ml of the same is subjected to reaction. After the reaction starts at 33° C., 0.5 ml of the same is sampled at every 2 minutes, and 0.1 ml of 1N HCl is added so that the reaction is stopped. Para-aminobenzoic acid thus produced is separated by using HPLC (Prominence) manufactured by Shimadzu Corporation, and as a column, Cosmosil packed column 5C18-AR-11 (4.6×250 mm, manufactured by Nacalai Tesque). The detection of the same is performed with a wavelength of 254 nm, so that the enzyme activity is calculated from an initial rate.

An analog of a DNA which consists of any one of base sequences of SEQ ID NOs 1 to 27, 129, 132 to 202 can be selected from, for example, DNA libraries of other biological species by PCR or hybridization using a primer or a probe that is designed in the usual way based on these base sequences.

Enhancement of DAHP Synthase Activity

The coryneform bacterium as a host desirably has enhanced activity of a 3-deoxy-D-arabi no-heptulosonate-7-phosphate (DAHP) synthase, as compared with a wild-type coryneform bacterium.

The DAHP synthase is an enzyme that generates DAHP as an initial metabolic product of an aromatic compound biosynthesis common pathway from erythrose-4-phosphate (E4P) and phosphoenolpyruvate (PEP).

The DAHP synthase activity can be enhanced by introducing a DAHP synthase gene, or mutation transfer or sequence substitution with respect to a regulatory sequence or a gene coding region of a DAHP synthase gene on a chromosome of a coryneform bacterium, which increases the amount of gene expression thereof, or alternatively, increases activity of a product of this gene.

Among these, enhancing DAHP synthase activity by introducing a DAHP synthase gene is simple and efficient.

Though the origin of a DAHP synthase gene to be introduced is not limited particularly, the DAHP synthase gene of *Corynebacterium* is preferable in that it has good 4-ABA production efficiency. Examples of the DAHP synthase gene of *Corynebacterium* include DAHP synthase gene aroG of *Corynebacterium glutamicum* (SEQ ID NO. 203).

Further, in particular, genes derived from *Escherichia coli* are also preferable.

Among the DAHP synthase genes derived from *Escherichia coli*, a DNA ($aroG^{S180F}$) which consists of a base sequence represented by SEQ ID NO. 211 is further more preferable. This gene is aroG, which is a DAHP synthase gene derived from *Escherichia coli*, into which a mutation (S180F) that changes the serine at position 180 to phenylalanine, and a gene product of this exhibits high resistance against feedback inhibition by an aromatic compound containing an aromatic amino acid, and high DAHP synthase activity. This was found by the inventors of the present invention by comparative investigation (unpublished).

A DNA which consists of a base sequence having 90% or more, preferably 95% or more, more preferably 98% or more of identity with SEQ ID NO: 203, and encodes a polypeptide having DAHP synthase activity, or a DNA that hybridizes to a DNA which consists of a base sequence complementary to SEQ ID NO: 203 under stringent conditions, and encodes a polypeptide having DAHP synthase activity, can be used as well.

The presence/absence of the DAHP synthase activity can be detected by causing phosphoenolpyruvate and erythrose-4-phosphate as substrates to react with each other, and quantitatively determining the generated 3-deoxy-D-arabino-heptulosonate-7-phosphate (DAHP) by the color development method using thiobarbituric acid (Appl. Environ. Microbiol., 74; 5497-5530 (2008)).

Enhancement of Chorismate Synthase Activity

The transformant of the present invention is preferably a coryneform bacterium as a host into which a gene that encodes chorismate synthase is further introduced. The chorismate synthase is an enzyme that catalyzes the conversion from 5-enolpyruvylshikimate-3-phosphate to chorismate.

Though the origin of a chorismate synthase gene to be introduced is not limited particularly, the chorismate synthase gene of bacteria of the genus *Corynebacterium*, in particular, *Corynebacterium glutamicum*, is preferable in that it has good 4-ABA production efficiency.

As the chorismate synthase gene of *Corynebacterium glutamicum*, aroC (for example, SEQ ID NO. 204) is known.

A DNA which consists of a base sequence having 90% or more, preferably 95% or more, more preferably 98% or more of identity with SEQ ID NO: 204, and encodes a polypeptide having chorismate synthase activity, or a DNA that hybridizes to a DNA which consists of a base sequence complementary to SEQ ID NO: 204 under stringent conditions, and encodes a polypeptide having chorismate synthase activity, can be used as well.

The chorismate synthase activity is measured by a known method (Kitzing, K. et al., Spectroscopic and Kinetic Characterization of the Bifunctional Chorismate Synthase from *Neurospora crassa*. J. Biol. Chem. 276: 42658-42666 (2001)). More specifically, the measurement is performed as follows: at 37° C., a test enzyme solution is added to a reaction solution composed of 100 mM potassium phosphate buffer (pH 7.6), 4 mM $MgSO_4$, 10 mM glutamine, 30 mM ammonium sulfate, 1 mM DTT, 0.01 mM FMN, 0.08 mM EPSP, and a crude enzyme solution of anthranilate synthase, so that the reaction starts; fluorescence of 390 nm, which indicates the generation of anthranilate, which is generated by a coupling reaction with anthranilate synthase, is monitored by F-2500 Fluorescence Spectrophotometer (manufactured by Hitachi, Ltd.), so that the enzyme activity is calculated from an initial rate. The reduction of FMN is performed by adding 1 mM NADPH. When the activity is detected, it is determined that chorismate synthase activity is exhibited.

Enhancement of Shikimate Kinase Activity

The transformant of the present invention is preferably a coryneform bacterium as a host into which a gene that encodes shikimate kinase is further introduced. The shikimate kinase is an enzyme that catalyzes the conversion from shikimate to shikimate-3-phosphate.

Though the origin of a shikimate kinase gene to be introduced is not limited particularly, the shikimate kinase gene of bacteria of the genus *Corynebacterium*, in particular, *Corynebacterium glutamicum*, is preferable in that it has good 4-ABA production efficiency.

As the shikimate kinase gene of *Corynebacterium glutamicum*, aroK (for example, SEQ ID NO. 205) is known.

A DNA which consists of a base sequence having 90% or more, preferably 95% or more, more preferably 98% or more of identity with SEQ ID NO: 205, and encodes a polypeptide having shikimate kinase activity, or a DNA that hybridizes to a DNA which consists of a base sequence complementary to SEQ ID NO: 205 under stringent conditions, and encodes a polypeptide having shikimate kinase activity, can be used as well.

The shikimate kinase activity is measured by a known method (Cheng, W C. et al., Structures of *Helicobacter pylori* shikimate kinase reveal a selective inhibitor-induced-fit mechanism. PLoS ONE. 7: e33481 (2012)). More specifically, the measurement is performed as follows: at 25° C., a test enzyme solution is added to a reaction solution composed of 100 mM tris-hydrochloric acid buffer (pH 7.5), 50 mM KCl, 5 mM $MgCl_2$, 1.6 mM shikimate, 2.5 mM ATP, 1 mM phosphoenolpyruvate, 0.1 mM NADH, a crude enzyme solution of pyruvate kinase, and a crude enzyme solution of lactate dehydrogenase, so that the reaction starts; 340 nm absorption of NADH, which decreases due to a coupling reaction between pyruviate kinase and lactate dehydrogenase is monitored by Beckman DU800 spectrophotometer (manufactured by Beckman Coulter, Inc.), so that the enzyme activity is calculated from an initial rate. When the activity is detected, it is determined that the shikimate kinase activity is exhibited.

Enhancement of 3-Dehydroquinate Synthase Activity

The transformant of the present invention is preferably a coryneform bacterium as a host into which a gene that encodes 3-dehydroquinate (DHQ) synthase is further introduced. The dehydroquinate synthase is an enzyme that catalyzes the conversion of DAHP into 3-dehydroquinate.

Though the origin of a 3-dehydroquinate synthase gene to be introduced is not limited particularly, a 3-dehydroquinate synthase gene of bacteria of the genus *Corynebacterium*, in particular, *Corynebacterium glutamicum*, is preferable in that it has good 4-ABA production efficiency.

As the 3-dehydroquinate synthase gene of *Corynebacterium glutamicum*, aroB (for example, SEQ ID NO. 206) is known.

A DNA which consists of a base sequence having 90% or more, preferably 95% or more, more preferably 98% or more of identity with SEQ ID NO: 206, and encodes a polypeptide having dehydroquinate synthase activity, or a DNA that hybridizes to a DNA which consists of a base sequence complementary to SEQ ID NO: 206 under stringent conditions, and encodes a polypeptide having dehydroquinate synthase activity, can be used as well.

The dehydroquinate synthase activity is measured by a known method (Meudi, S. et al., Dehydroquinate synthase from *Escherichia coli*, and its substrate 3-deoxy-D-arabino-heptulosonic acid 7-phosphate. Methods. Enzymol. 142: 306-314 (1987)). More specifically, at 33° C., a test enzyme solution is added to a reaction solution composed of 50 mM potassium phosphate buffer (pH 7.0), 0.2 mM DAHP, 0.2 mM $NAD^+$, 1 mM Cobalt(II) chloride.$6H_2O$, and a crude enzyme solution of 3-DHQ dehydratase, so that the reaction starts; 234 nm absorption (=12000/M·cm), which exhibits the generation of 3-DHS, which is generated by a coupling reaction with 3-DHQ dehydratase, is monitored by Beckman DU800 spectrophotometer (manufactured by Beckman Coulter, Inc.). Activity of generating 1 μmol of 3-DHQ per one minute at 33° C. is assumed to be one unit of dehydroquinate synthase activity, and when the activity is detected, it is determined that the dehydroquinate synthase activity is exhibited.

Construction of Vector for Transformation

The transgene described above may be amplified by PCR and then cloned into a suitable vector which can be amplified in a Coryneform bacterium.

The plasmid vector may be any plasmid vector as long as it includes a gene responsible for autonomously replicating function in a coryneform bacterium. Specific examples of the plasmid vector include pAM330 derived from *Brevibacterium lactofermentum* 2256 [JP-A-58-67699], [Miwa, K. et al., Cryptic plasmids in glutamic acid-producing bacteria. Agric. Biol. Chem. 48:2901-2903 (1984)] and [Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)], pHM1519 derived from *Corynebacterium glutamicum* ATCC3058 [Miwa, K. et al., Cryptic plasmids in glutamic acid-producing bacteria. Agric. Biol. Chem. 48:2901-2903 (1984)] and pCRY30 derived from the same [Kurusu, Y. et al., Identification of plasmid partition function in coryneform bacteria. Appl. Environ. Microbiol. 57:759-764 (1991)], pCG4 derived from *Corynebacterium glutamicum* T250 [JP-A-57-183799], [Katsumata, R. et al., Protoplast transformation of glutamate-producing bacteria with plasmid DNA. J. Bacteriol., 159:306-311 (1984)], pAG1, pAG3, pAG14, pAG50 [JP-A-62-166890], and pEK0, pEC5, pEKEx1 [Eikmanns, B. J. et al., A family of *Corynebacterium glutamicum/Escherichia coli* shuttle vectors for cloning, controlled gene expression, and promoter probing. Gene, 102:93-98 (1991)]; etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PIdhA as a promoter of lactate dehydrogenase A gene (IdhA), all of which are derived from *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and the electric pulse method. Inter alia, preferred for a coryneform bacterium is the electric pulse method, which can be performed by a known method (Kurusu, Y. et al., Electroporation-transformation system for Coryneform bacteria by auxotrophic complementation. Agric. Biol. Chem. 54: 443-447 (1990)).

The transformant may be cultured using a culture medium usually used for culture of microorganisms. The culture medium may be a natural or synthetic medium containing a carbon source, a nitrogen source, inorganic salts, other nutritional substances, etc.

Examples of the carbon source include saccharides and saccharide alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. These carbon sources may be used alone or as a mixture of two or more thereof. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 10 w/v %.

Examples of the inorganic salts include potassium dihydrogen phosphate, dipotassium hydrogen phosphate, magnesium sulfate, sodium chloride, iron (II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.1 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration thereof is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc. The pH of the culture medium is preferably about 5 to 9.

Examples of the preferable microbial culture medium include A medium [Inui, M. et al., Metabolic analysis of *Corynebacterium glutamicum* during lactate and succinate productions under oxygen deprivation conditions. J. Mol. Microbiol. Biotechnol. 7:182-196 (2004)], BT-medium [Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)], etc. The culture temperature may be about 15 to 45° C., and the culture period may be about 1 to 7 days.

(2) Process of Producing 4-ABA or a Salt Thereof

4-ABA or a salt thereof can be produced by a process that includes a step of culturing, or causing reaction of, the above-described transformant of the present invention in a reaction solution containing a saccharide, so as to cause the transformant to produce the 4-ABA or the salt thereof.

Glucose is preferred as the saccharide, but other saccharides that are metabolized into glucose can also be used. Such saccharides include oligosaccharides and polysaccharides that have a glucose unit. Examples of such saccharides include monosaccharides, such as fructose, mannose, arabinose, xylose, and galactose; disaccharides, such as cellobiose, sucrose, lactose, maltose, trehalose, cellobiose, and xylobiose; polysaccharides, such as dextrin and soluble starch; etc.

Also, molasses, which contains these starting compounds, can also be used, for example. In addition, a saccharified solution which is obtainable by saccharifying, using a diastatic enzyme, non-edible agricultural waste including straw (rice straw, barley straw, wheat straw, rye straw, oat straw, etc.), bagasse, and corn stover; energy crops including switchgrass, napier grass, and *Miscanthus*; wood waste; waste paper; etc. and which contains a plurality of kinds of saccharides, including glucose, can also be used.

Growth of Microorganism

Before the culture in a medium containing a saccharide, that is, the reaction, the transformant is preferably cultured and grown under aerobic conditions at about 25 to 38° C. for about 12 to 48 hours.

Culture Medium

The culture medium used for aerobic culture of the transformant before the reaction may be a natural medium or a synthetic medium containing a carbon source, a nitrogen source, inorganic salts, other nutritional substances, etc.

Examples of the carbon source that can be used include saccharides (monosaccharides such as glucose, fructose, mannose, xylose, arabinose, and galactose; disaccharides such as sucrose, maltose, lactose, cellobiose, xylobiose, and trehalose; polysaccharides such as starch; and molasses); saccharide alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

One kind of these carbon sources or a mixture of two or more kinds of the same may be used.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. One kind of these nitrogen sources or a mixture of two or more kinds of the same may be used. The concentration of these nitrogen sources in the culture medium varies depending on the kind of the nitrogen compound, but is usually about 0.1 to 10 w/v %.

Examples of the inorganic salts include potassium dihydrogenphosphate, dipotassium hydrogenphosphate, magnesium sulfate, sodium chloride, iron (II) nitrate, manganese sulfate, zinc sulfate, cobalt sulfate, and calcium carbonate. One kind of these inorganic salts or a mixture of two or more kinds of the same may be used. The concentration of the inorganic salts in the culture medium varies depending on the kind of the inorganic salts, but is usually about 0.01 to 1 w/v %.

Examples of the nutritional substances include meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins maybe added as needed. Examples of the vitamins include biotin, thiamine (vitamin B1), pyridoxine (vitamin B6), pantothenic acid, inositol, nicotinic acid, etc.

The pH of the culture medium is preferably about 5 to 9.

Specific examples of the preferable culture medium for coryneform bacteria include A medium [Inui, M. et al., Metabolic analysis of *Corynebacterium glutamicum* during lactate and succinate productions under oxygen deprivation conditions. J. Mol. Microbiol. Biotechnol. 7:182-196 (2004)], BT-medium [Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)], etc. Such a culture medium can be used after prepared so as to contain a saccharide at a concentration in the above-mentioned range.

Culture Solution or Reaction Solution

The culture solution or reaction solution used may be a natural or synthetic reaction solution containing a carbon source, a nitrogen source, inorganic salts, etc.

The carbon source used may be saccharide described above, or a molasses or a saccharified solution containing such compounds. As the carbon source, besides saccharides, saccharide alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin can also be used.

One kind of these carbon sources or a mixture of two or more kinds of the same may be used.

The concentration of saccharides as the starting compound in the reaction solution is preferably about 1 to 20 w/v %, more preferably about 2 to 10 w/v %, and still more preferably about 2 to 5 w/v %.

The total concentration of the carbon sources including saccharides as the starting compound in the reaction solution may be usually about 2 to 5 w/v %.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. One kind of these nitrogen sources or a mixture of two or more kinds of the same may be used. The concentration of these nitrogen sources in the reaction solution varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron (II) nitrate, manganese sulfate, zinc sulfate, cobalt sulfate, and calcium carbonate. One kind of these inorganic salts or a mixture of two or more kinds of the same may be used. The concentration of the inorganic salts in the reaction solution varies depending on the kind of the inorganic salts, but is usually about 0.01 to 1 w/v %.

Further, vitamins maybe added as needed. Examples of the vitamins include biotin, thiamine (vitamin B1), pyridoxine (vitamin B6), pantothenic acid, inositol, nicotinic acid, etc.

The pH of the reaction solution is preferably about 5 to 9.

Specific examples of the preferable reaction solution for coryneform bacteria include the above-mentioned BT-medium, etc. Such a culture medium can be used after prepared so as to contain a saccharide at a concentration in the above-mentioned range.

Culturing Conditions or Reaction Conditions

The culture temperature or the reaction temperature, that is, the temperature for keeping the transformant alive during the reaction is preferably about 20 to 50° C., and more preferably about 25 to 47° C. When the temperature is in the above range, 4-ABA can be efficiently produced.

The culture period or the reaction period is preferably about 1 to 7 days, and more preferably about 1 to 3 days.

The culture may be a batch process, a fed-batch process, or a continuous process. Among them, a batch process is preferred.

The reaction may be performed under aerobic conditions or reducing conditions. The 4-ABA production ability of the transformant of the present invention itself is higher under aerobic conditions. However, aerobic conditions favor the growth of the transformant and the starting compound is consumed for the growth. Accordingly, the 4-ABA production efficiency is lowered.

It is therefore preferred that the reaction is performed under conditions that are aerobic and under which the transformant does not grow. In the present invention, “does not grow” includes “substantially does not grow” and “hardly grows”. For example, growth of the transformant can be avoided or inhibited by the use of a reaction solution in which one or more of compounds essential for the growth of the microorganism, for example, vitamins, such as biotin and thiamine, nitrogen sources, etc. is depleted or limited.

Under reducing conditions, coryneform bacteria substantially do not grow, and therefore, the starting compound is not consumed for the growth, which leads to a higher 4-ABA production efficiency.

The “reducing conditions” is defined based on the oxidation-reduction potential of the reaction solution. The oxidation-reduction potential of the reaction solution is preferably about −200 mV to −500 mV, and more preferably about −150 mV to −500 mV.

The reducing conditions of the reaction solution can be simply estimated using resazurin indicator (in reducing conditions, decolorization from blue to colorless is observed). However, for precise measurement, a redox-potential meter (for example, ORP Electrodes made by BROADLEY JAMES) is used.

As a method of preparing a reaction solution under reducing conditions, any publicly known method can be used without limitation. For example, as a liquid medium for preparation of the reaction solution, an aqueous solution for a reaction solution may be used instead of distilled water or the like. As reference for preparation of the aqueous solution for a reaction solution, for example, the method for preparing a culture medium for strictly anaerobic microorganisms, such as sulfate-reducing microorganisms (Pfennig, N. et al.: “The dissimilatory sulfate-reducing bacteria, in The Prokaryotes, A Handbook on Habitats, Isolation and Identification of Bacteria”, Ed. by Starr, M. P. et al. Berlin, Springer Verlag, 926-940, 1981, and “Nogeikagaku Jikkensho” Ed. by Kyoto Daigaku Hogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction solution under reducing conditions can be obtained. In this case, for removal of dissolved gases, especially dissolved oxygen, distillated water or the like may be treated under reduced pressure of about 10 mmHg or less, preferably about 5 mmHg or less, more preferably about 3 mmHg or less, for about 1 to 60 minutes, preferably for about 5 to 40 minutes, whereby an aqueous solution for a reaction solution under reducing conditions can be obtained.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction solution under reducing conditions can be prepared.

These methods may be suitably combined to prepare an effective aqueous solution for a reaction solution under reducing conditions.

In the case of a reaction under reducing conditions, it is preferred to maintain the reducing conditions of the reaction solution during the reaction. For maintenance of reducing conditions, it is preferred that oxygen from the outside of the reaction system is prevented to the utmost extent from entering the system. Specific examples of the method employed for this purpose include a method that includes encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Through the culture performed in the above manner, 4-ABA or a salt of the same is produced in the culture solution or the reaction solution.

Examples of the salt of 4-ABA, which varies depending on the components of the culture medium or the reaction solution, include alkali metal salts (sodium salt, potassium salt, etc.), and alkali earth metal salts (magnesium salt, calcium salt, etc.).

EXAMPLE

Reference Example 1

Verification that Coryneform Bacterium Exhibits Higher Resistance Under the Presence of a Product Thereof, as Compared with Other Microorganisms Experiments about growth inhibition by para-aminobenzoic acid in aerobic culture were carried out, regarding *Corynebacterium glutamicum, Escherichia coli, Streptomyces lividans, Pseudomonas putida*, and *Saccharomyces cerevisiae*. No example of *Pseudomonas putida* S12 used in the present experiment has been reported to be a para-aminobenzoic acid producing host, but it was used as a comparative example, since it has been reported to be a solvent resistant bacterium and could be considered to have excellent resistance to para-aminobenzoic acid.

*Corynebacterium glutamicum* strain R was applied to an A-agar plate containing glucose at 4%, and was incubated at 33° C. for 15 hours in a dark place. One platinum loop of *Corynebacterium glutamicum* grown on the plate described above was inoculated in a test tube having therein 10 ml of the A-liquid medium containing of glucose at 4%, and was subjected to aerobic shaking culture at 33° C. for 15 hours. *Corynebacterium glutamicum* grown under the above-described conditions was inoculated in 10 ml of the A-liquid medium containing glucose at 4% so that the initial bacterial cell concentration $OD_{610}$=0.05. Simultaneously, para-aminobenzoic acid was added so that the final concentrations thereof became 0, 100, 200, 300, and 400 mM, and aerobic shaking culture was carried out at 33° C. The growth of bacterial cells was determined by measuring $OD_{610}$.

*Escherichia coli* JM109 was applied to LB-agar plate [containing 1% polypeptone, 0.5% yeast extract, 0.5% sodium chloride, and 1.5% agar], and was incubated at 37° C. for 15 hours in a dark place. *Escherichia coli* grown on the plate described above was inoculated in LB-liquid medium [containing 1% polypeptone, 0.5% yeast extract, and 0.5% sodium chloride], and was subjected to aerobic shaking culture at 37° C. for 13 hours. *Escherichia coli* grown under the above-described conditions was inoculated in 100 ml of LB-liquid medium so that the initial bacterial cell concentration $OD_{610}$=0.05. Simultaneously, para-aminobenzoic acid was added so that the final concentrations thereof became 0, 100, 200, 300, and 400 mM, and aerobic shaking culture was carried out at 37° C. The growth of bacterial cells was determined by measuring $OD_{610}$.

*Streptomyces lividans* 1326 was applied to LB-agar plate, and was incubated at 28° C. for 24 hours in a dark place. *Streptomyces lividans* grown on the plate described above was inoculated in LB-liquid medium with a coil spring, and aerobic shaking culture was carried out at 28° C. for 24 hours. *Streptomyces lividans* grown under the above-described conditions was inoculated in 10 ml of LB-liquid medium with a coil spring so that the initial bacterial cell concentration $OD_{610}$=0.2. Simultaneously, para-aminobenzoic acid was added so that the final concentrations thereof became 0, 100, 200, 300 mM, and aerobic shaking culture was carried out at 28° C. The growth of bacterial cells was determined by measuring $OD_{610}$.

*Pseudomonas putida* S12 was applied to the LB-agar plate, and was incubated at 30° C. for 15 hours in a dark place. *Pseudomonas putida* grown on the plate described above was inoculated in the LB-liquid medium, and aerobic shaking culture was carried out at 30° C. for 13 hours. *Pseudomonas putida* grown under the above-described conditions was inoculated in 100 ml of LB-liquid medium so that the initial bacterial cell concentration $OD_{610}$=0.05, simultaneously, para-aminobenzoic acid was added so that the final concentrations thereof became 0, 100, 200, 300 mM, and aerobic shaking culture was carried out at 30° C. The growth of bacterial cells was determined by measuring absorbance of $OD_{610}$.

*Saccharomyces cerevisiae* W303 was applied to YEPD-agar plate [containing 2% polypeptone, 1% yeast extract, 2% glucose, and 1.5% agar] and was incubated at 30° C. for 20 hours in a dark place. *Saccharomyces cerevisiae* grown on the plate described above was inoculated in the YEPD-liquid medium [containing 2% polypeptone, 1% yeast extract, and 2% glucose], and aerobic shaking culture was carried out at 30° C. for 13 hours. *Saccharomyces cerevisiae* grown under the above-described conditions was inoculated in 100 ml of YEPD-liquid medium so that the initial bacterial cell concentration $OD_{610}$=0.05. Simultaneously, para-aminobenzoic acid was added so that the final concentrations thereof became 0, 100, 200, 300 mM, and aerobic shaking culture was carried out at 30° C. The growth of bacterial cells was determined by measuring $OD_{610}$.

How the addition of para-aminobenzoic acid to medium influenced aerobic growth was analyzed, and the results are shown in FIG. 1.

The growth of *Escherichia coli* JM109 was significantly inhibited under the presence of 100 mM para-aminobenzoic acid, and the growth thereof was substantially completely inhibited under the presence of 300 mM para-aminobenzoic acid.

The growth of *Streptomyces lividans* 1326 was significantly inhibited under the presence of 100 mM para-aminobenzoic acid, and the growth thereof was substantially completely inhibited under the presence of 200 mM para-aminobenzoic acid.

Surprisingly, the growth of *Pseudomonas putida* S12 (strain that was reported to be solvent-resistant) was substantially completely inhibited under the presence of 100 mM para-aminobenzoic acid, which was very low concentration.

The growth of *Saccharomyces cerevisiae* W303 was strongly inhibited by 200 mM para-aminobenzoic acid, and was extremely strongly inhibited by 300 mM para-aminobenzoic acid.

In contrast, *Corynebacterium glutamicum* strain R was able to grow under the presence of 300 mM para-aminobenzoic acid, under which the growth of *Escherichia coli, Streptomyces lividans, Pseudomonas putida*, and *Saccharomyces cerevisiae* was substantially completely inhibited. Further, *Corynebacterium glutamicum* was also able to grow under the presence of 400 mM para-aminobenzoic acid, and grew to the same level as that of the growth under the presence of 200 mM para-aminobenzoic acid 24 hours after the start of the culture, though it is not shown herein.

In this way, it was indicated that *Corynebacterium glutamicum* has high resistance against para-aminobenzoic acid as compared with other microorganisms that are reported to be para-aminobenzoic acid producing hosts and typical solvent-resistant bacteria, and therefore, *Corynebacterium glutamicum* is highly suitable as a host for producing para-aminobenzoic acid.

Reference Example 2

Verification that Coryneform Bacterium is Suitable as a Host Under the Presence of a Product Thereof (Influence of Para-Aminobenzoic Acid on Saccharide Consumption Rate)

As indicated by Reference Example 1, *Corynebacterium glutamicum* can grow under the presence of high-concentration para-aminobenzoic acid. Here, in addition, it is proved by experiments described below that the influence to the glucose consumption rate is extremely small even under the presence of high-concentration para-aminobenzoic acid.

Influences of para-aminobenzoic acid on the glucose consumption rate were examined by a method described below, using *Corynebacterium glutamicum* strain R.

After a wild strain of *Corynebacterium glutamicum* was inoculated in 10 ml of the A-liquid medium containing 2% glucose, aerobic shaking culture was carried out at 33° C. for 18 hours. After the same strain was inoculated in 100 ml of the A-liquid medium containing 2% glucose, aerobic shaking culture was carried out at 33° C. for 12 hours.

Bacterial cells of the strain grown under the above-described conditions were collected by centrifugation (4° C., 3000×g, 10 minutes), and bacterial cells thus obtained were suspended in 600 ml of a culture solution [obtained by dissolving the following in in 1 L of distilled water: $(NH_4)_2SO_4$ 21 g, $KH_2PO_4$ 0.5 g, $K_2HPO_4$ 0.5 g, $MgSO_4.7H_2O$ 0.5 g, 0.06% (w/v) $FeSO_4.7H_2O$+0.042% (w/v) $MnSO_4.2H_2O$ 1 mL, 0.02% (w/v) biotin solution 25 μL, 0.01% (w/v) thiamine solution 2 mL, yeast extract 2 g, and vitamin assay casamino acid 7 g] containing 6% glucose and 5 g/L of an antifoam agent (DISFOAM CB-442) in a jar fermenter culture vessel having a capacity of 1000 ml so that $OD_{610}$=0.5, and aeration agitation culture was carried out by the 1000 ml capacity jar fermenter under the conditions of 33° C., pH 7.0 (controlled by adding 5.0 N ammonium hydroxide), aeration amount of 0.6 L/min (air, 1 vvm), DO 10%, for 18 hours.

Bacterial cells of the strain grown under the above-described conditions were collected by centrifugation (4° C., 5000×g, 10 minutes), and the bacterial cells thus obtained were washed with 0.9% sodium chloride aqueous solution once. The bacterial cells were suspended in 250 ml of a reaction solution [obtained by dissolving $(NH_4)_2SO_4$ 7 g, $KH_2PO_4$ 0.5 g, $K_2HPO_4$ 0.5 g, $MgSO_4.7H_2O$ 0.5 g, 0.06% (w/v) $Fe_2SO_4.7H_2O$+0.042% (w/v) $MnSO_4.2H_2O$ 1 ml, 0.01% (w/v) thiamine solution 2 ml in 1 L of distilled water] containing 5% glucose, and 0 mM, 50 mM, 100 mM or 200 mM of para-aminobenzoic acid, so that 100 g of wet bacterial cells per liter were contained (10% of the medium volume in terms of weight of wet bacterial cells). The glucose consumption rates were compared under the conditions of 33° C., pH 7.0 (controlled by adding 5.0 N ammonium hydroxide), aeration amount of 0.25 L/min (air, 1 vvm), DO (dissolved oxygen) 5%, by using the 1000 ml capacity jar fermenter. The glucose concentration in the reaction solution was monitored by using a glucose sensor. The results are shown in FIG. 2.

In this way, *Corynebacterium glutamicum* exhibited no substantial decrease in the saccharide consumption rate even under the presence of para-aminobenzoic acid at a high concentration. The combination of Reference Examples 1 and 2 could prove that *Corynebacterium glutamicum* is remarkably useful as a host in the production of para-aminobenzoic acid.

Example 1

Construction of 4-ABA Producing Strain (1) Preparation/Obtainment of Chromosome DNA To obtain a gene encoding 4-ABA-production-related enzyme, a chromosome DNA was prepared or obtained from the following strains:

Bacteria of *Corynebacterium glutamicum* (*Corynebacterium glutamicum*) R (FERM P-18976), *Escherichia coli* (*Escherichia coli* K-12 MG1655), *Escherichia fergusonii* (*Escherichia fergusonii* NBRC 102419), *Saccharophagus degradans* (*Saccharophagus degradans* ATCC 43961), *Shewanella woodyi* (*Shewanella woodyi* ATCC 51908), *Arthrobacter phenanthrenivorans* (*Arthrobacter phenanthrenivorans* JCM 16027), *Azotobacter vinelandii* (*Azotobacter vinelandii* ATCC 9104), *Ochrobactrum anthropi* (*Ochrobactrum* anthropic NBRC 15819), *Clostridium beijerinckii* (*Clostridium beijerinckii* NCIMB 8052), *Xenorhabdus bovienii* (*Xenorhabdus bovienii* ATCC 35271), *Bacillus pseudofirmus* (*Bacillus pseudofirmus* JCM 9141), *Bacteroides thetaiotaomicron* (*Bacteroides thetaiotaomicron* JCM 5827), *Ferrimonas balearica* (*Ferrimonas balearica* NBRC 104245), *Enterobacter cloacae* (*Enterobacter cloacae* NBRC 13535), *Corynebacterium callunae* (*Corynebacterium callunae* JCM 9489), *Corynebacterium efficiens* (*Corynebacterium efficiens* NBRC 100395), *Corynebacterium casei* (*Corynebacterium casei* JCM 12072), *Corynebacterium ureicelerivorans*(*Corynebacterium ureicelerivorans* JCM 15295), *Corynebacterium argentoratense* (*Corynebacterium argentoratense* JCM 10392), *Corynebacterium terpenotabidum* (*Corynebacterium terpenotabidum* JCM 10555)), *Neurospora crassa* (*Neurospora crassa* ATCC 36373), *Rhodococcus opacus* (*Rhodococcus opacus* ATCC 51881), *Rhodococcus opacus* (*Rhodococcus erythropolis* ATCC 27854), *Ralstonia eutropha* (*Ralstonia eutropha* IAM 12368) were cultured according to information obtained from organizations from which the strains are available, and chromosome DNAs thereof were prepared by using DNA genome extraction kit (trade name: "GenomicPrep Cells and Tissue DNA Isolation Kit", manufactured by Amersham plc).

Chromosome DNAs of *Anabaena variabilis* (*Anabaena variabilis* ATCC 29413D-5), *Caulobacter crescentus* (*Caulobacter crescentus* ATCC 19089D-5), and *Synechococcus* sp. (*Synechococcus* sp. ATCC 27264D-5) were availed from ATCC.

(2) Construction of Plasmid Expressing 4-ABA-Production-Related Gene

Primer sequences used for isolating target enzyme genes are shown in Table 1. In PCR, Veriti Thermal Cycler (manufactured by Applied Biosystems Inc.) was used, and PrimeSTAR HS DNA Polymerase (manufactured by Takara Bio Inc.) was used as a reaction reagent.

DNA fragments obtained were introduced into cloning vectors containing PgapA promoter (pCRB207 [Hasegawa S et al., Improvement of the redox balance increases L-valine production by *Corynebacterium glutamicum* under oxygen deprivation conditions. Appl Environ Microbiol. 78(3):865-875 (2012)], pCRB209 [WO2012/033112], pCRB210 [WO2012/033112], pCRB240).

TABLE 1

4-ABA-production-related gene isolating primers

| Gene source | Enzyme gene | Forward | Reverse |
|---|---|---|---|
| *Escherichia coli* | pabC | SEQ ID NO. 28 | SEQ ID NO. 29 |
| *Escherichia fergusonii* | pabC | SEQ ID NO. 30 | SEQ ID NO. 31 |
| *Saccharophagus degradans* | pabC | SEQ ID NO. 32 | SEQ ID NO. 33 |
| *Shewanella woodyi* | pabC | SEQ ID NO. 34 | SEQ ID NO. 35 |
| *Arthrobacter phenanthrenivorans* | pabC | SEQ ID NO. 36 | SEQ ID NO. 37 |
| *Anabaena variabilis* | pabC | SEQ ID NO. 38 | SEQ ID NO. 39 |
| *Azotobacter vinelandii* | pabC | SEQ ID NO. 40 | SEQ ID NO. 41 |
| *Ochrobactrum anthropi* | pabC | SEQ ID NO. 42 | SEQ ID NO. 43 |
| *Clostridium beijerinckii* | pabC | SEQ ID NO. 44 | SEQ ID NO. 45 |
| *Xenorhabdus bovienii* | pabC | SEQ ID NO. 46 | SEQ ID NO. 47 |
| *Bacillus pseudofirmus* | pabC | SEQ ID NO. 48 | SEQ ID NO. 49 |
| *Caulobacter crescentus* | pabC | SEQ ID NO. 50 | SEQ ID NO. 51 |
| *Synechococcus* sp. | pabC | SEQ ID NO. 52 | SEQ ID NO. 53 |
| *Bacteroides thraiotaomicron* | pabC | SEQ ID NO. 54 | SEQ ID NO. 55 |
| *Ferrimonas balearica* | pabC | SEQ ID NO. 56 | SEQ ID NO. 57 |
| *Enterobacter cloacae* | pabA | SEQ ID NO. 58 | SEQ ID NO. 59 |
| *Corynebacterium callunae* | pabAB | SEQ ID NO. 60 | SEQ ID NO. 61 |
| *Corynebacterium efficiens* | pabAB | SEQ ID NO. 62 | SEQ ID NO. 63 |
| *Corynebacterium casei* | pabAB | SEQ ID NO. 64 | SEQ ID NO. 65 |
| *Corynebacterium glutamicum* | pabAB | SEQ ID NO. 66 | SEQ ID NO. 67 |
| *Corynebacterium ureicelerivorans* | pabAB | SEQ ID NO. 68 | SEQ ID NO. 69 |
| *Corynebacterium argentoratense* | pabAB | SEQ ID NO. 70 | SEQ ID NO. 71 |
| *Corynebacterium terpenotabidum* | pabAB | SEQ ID NO. 72 | SEQ ID NO. 73 |
| *Neurospora crassa* | pabAB | SEQ ID NO. 74 | SEQ ID NO. 75 |
| *Rhodococcus opacus* | pabAB | SEQ ID NO. 76 | SEQ ID NO. 77 |
| *Rhodococcus erythropolis* | pabAB | SEQ ID NO. 78 | SEQ ID NO. 79 |
| *Ralstonia eutropha* | pabBC | SEQ ID NO. 130 | SEQ ID NO. 131 |
| *Escherichia coli* | aroG | SEQ ID NO. 117 | SEQ ID NO. 118 |
| *Escherichia coli* | aroG(S180F) | SEQ ID NO. 119 | SEQ ID NO. 120 |
| *Corynebacterium glutamicum* | aroC, aroK, aroB | SEQ ID NO. 121 | SEQ ID NO. 122 |
| *Corynebacterium glutamicum* | aroA | SEQ ID NO. 123 | SEQ ID NO. 124 |
| *Corynebacterium glutamicum* | aroD | SEQ ID NO. 125 | SEQ ID NO. 126 |
| *Corynebacterium glutamicum* | aroE | SEQ ID NO. 127 | SEQ ID NO. 128 |

<Construction of pCRB240 Cloning Vector>

The promoter sequence of the gapA gene encoding glyceraldehyde-3-phosphate dehydrogenase derived from *Corynebacterium glutamicum* strain R, and the rrnB T1T2 bidirectional terminator sequence derived from the cloning vector pKK223-3 (manufactured by Pharmacia) were introduced into the vector pCRB1 including the pBL1 ori sequence [J Mol Microbiol Biotechnol. 8(4):243-254 (2004)]. Primers of SEQ ID NOs. 207 and 208 were used for amplifying the PgapA sequence, and primers of SEQ ID NOs. 209 and 210 were used for amplifying the terminator sequence. The cloning vector including the PgapA promoter thus obtained was named pCRB240. The primer sequences used for constructing pCRB240 were SEQ ID NOs. 207, 208, 209 and 210.

The names of the cloning vectors introduced and the plasmids obtained are shown in Table 2. Since aroC, aroK, and aroB were arranged continuously in the same orientation on the chromosome, they were cloned altogether (SEQ ID NO. 113).

TABLE 2

4-ABA-production-related gene expression plasmids

| Gene source | Enzyme gene | Introduced vector | Plasmid |
|---|---|---|---|
| *Escherichia coli* | pabC | pCRB209 | Pani151 |
| *Escherichia fergusonii* | pabC | pCRB209 | Pani159 |
| *Saccharophagus degradans* | pabC | pCRB209 | Pani161 |
| *Shewanella woodyi* | pabC | pCRB209 | Pani231 |
| *Arthrobacter phenanthrenivorans* | pabC | pCRB209 | Pani237 |
| *Anabaena variabilis* | pabC | pCRB209 | Pani240 |
| *Azotobacter vinelandii* | pabC | pCRB207 | Pani241 |
| *Ochrobactrum anthropi* | pabC | pCRB207 | Pani243 |
| *Clostridium beijerinckii* | pabC | pCRB209 | Pani245 |
| *Xenorhabdus bovienii* | pabC | pCRB209 | Pani246 |
| *Bacillus pseudofirmus* | pabC | pCRB207 | Pani247 |
| *Caulobacter crescentus* | pabC | pCRB207 | Pani248 |
| *Synechococcus* sp. | pabC | pCRB209 | Pani249 |
| *Bacteroides thraiotaomicron* | pabC | pCRB209 | Pani250 |
| *Ferrimonas balearica* | pabC | pCRB207 | Pani242 |
| *Enterobacter cloacae* | pabA | pCRB209 | Pani178 |
| *Corynebacterium callunae* | pabAB | pCRB209 | Pani198 |
| *Corynebacterium efficiens* | pabAB | pCRB209 | Pani190 |
| *Corynebacterium casei* | pabAB | pCRB209 | Pani206 |
| *Corynebacterium glutamicum* | pabAB | pCRB240 | Pani1 |
| *Corynebacterium ureicelerivorans* | pabAB | pCRB209 | Pani251 |
| *Corynebacterium argentoratense* | pabAB | pCRB209 | Pani214 |
| *Corynebacterium terpenotabidum* | pabAB | pCRB209 | Pani213 |
| *Neurospora crassa* | pabAB | pCRB209 | Pani199 |
| *Rhodococcus opacus* | pabAB | pCRB209 | Pani212 |
| *Rhodococcus erythropolis* | pabAB | pCRB209 | Pani211 |
| *Ralstonia eutropha* | pabBC | pCRB209 | Pani171 |
| *Escherichia coli* | aroG | pCRB210 | pSKM1 |
| *Escherichia coli* | aroG(S180F) | | pCRB237 |
| *Corynebacterium glutamicum* | aroC, aroK, aroB | pCRB209 | pCRB270 |
| *Corynebacterium glutamicum* | aroA | pCRB207 | pCRB271 |
| *Corynebacterium glutamicum* | aroD | pCRB209 | pCRB272 |
| *Corynebacterium glutamicum* | aroE | pCRB209 | pCRB273 |

PgapA promoter fusion enzyme gene fragments were obtained from 4-ABA-production-related gene expression plasmids shown in Tables 1 and 2 described above, and were introduced into plasmids (pCRB1 [NCBI GenBank: AB444682], pCRB15 [NCBI GenBank: AB444683]) that can coexist in *Corynebacterium glutamicum.* 4-ABA-production-related gene plasmids obtained are shown in Table 3.

TABLE 3

4-ABA-production-related gene expression plasmids (Coexistent in *Corynebacterium glutamicum*)

| Gene source | Enzyme gene | Introduced vector | Plasmid |
|---|---|---|---|
| *Enterobacter cloacae* | pabA | pCRB15 | Pani187 |
| *Neurospora crassa* | pabAB | pCRB1 | Pani219 |
| *Escherichia coli* | pabC | pCRB1 | Pani191 |

PgapA promoter fusion enzyme gene fragments were obtained from 4-ABA-production-related gene expression plasmids shown in Table 2 described above, and were introduced into plasmids (pSTV28 [manufactured by Takara Bio Inc.]) that can coexist in *Escherichia coli.* 4-ABA-production-related gene plasmids obtained are shown in Table 4.

TABLE 4

4-ABA-production-related gene expression plasmids (Coexistent in *Escherichia coli*)

| Gene source | Enzyme gene | Introduced vector | Plasmid |
|---|---|---|---|
| *Escherichia coli* | pabC | pSTV28 | Pani269 |

(3) Construction of PABA-Production-Related Gene Chromosome Introduced Strain

A DNA region necessary for markerless introduction of a PABA-production-related gene into chromosome of *Corynebacterium glutamicum* strain R was determined based on a sequence that was reported not to be essential for the growth of *Corynebacterium glutamicum* strain R [Appl. Environ. Microbiol. 71:3369-3372 (2005)] (SSI region). This DNA region was amplified by the PCR method. The DNA fragment thus obtained was introduced into the markerless gene transfer plasmid pCRA725 [J. Mol. Microbiol. Biotechnol. 8:243-254 (2004), (JP-A-2006-124440)]. To pCRB260, pCRB263, pCRB265, pCRB266 and pCRB267, a restriction enzyme site (unique site) for incorporating a gene in the SSI region was introduced by the inverse PCR method. The primer sequences used for isolation and Inverse PCR of the SSI regions and chromosome transfer vectors obtained are shown in Table 5.

TABLE 5

The primer sequences used for isolating SSI regions and chromosome transfer vectors obtained

| Chromosome transfer vector | SSI region | Forward | Reverse |
|---|---|---|---|
| pCRB259 | SSI 2-2 | SEQ ID NO. 80 | SEQ ID NO. 81 |
| pCRB260 | SSI 2-3 | SEQ ID NO. 82 | SEQ ID NO. 83 |
| | | SEQ ID NO. 84* | SEQ ID NO. 85* |
| pCRB261 | SSI 2-4 | SEQ ID NO. 86 | SEQ ID NO. 87 |
| pCRB262 | SSI 3-3 | SEQ ID NO. 88 | SEQ ID NO. 89 |
| pCRB263 | SSI 4-7 | SEQ ID NO. 90 | SEQ ID NO. 91 |
| | | SEQ ID NO. 92* | SEQ ID NO. 93* |
| pCRB264 | SSI 6-2 | SEQ ID NO. 94 | SEQ ID NO. 95 |
| pCRB265 | SSI 7 | SEQ ID NO. 96 | SEQ ID NO. 97 |
| | | SEQ ID NO. 98* | SEQ ID NO. 99* |
| pCRB266 | SSI 8 | SEQ ID NO. 100 | SEQ ID NO. 101 |
| | | SEQ ID NO. 102* | SEQ ID NO. 103* |
| pCRB267 | SSI 9-4 | SEQ ID NO. 104 | SEQ ID NO. 105 |
| | | SEQ ID NO. 106* | SEQ ID NO. 107* |
| pCRB268 | SSI 10-2 | SEQ ID NO. 108 | SEQ ID NO. 109 |
| pCRB269 | SSI 10-3 | SEQ ID NO. 110 | SEQ ID NO. 111 |

*Primer used in Inverse PCR

PgapA promoter fusion enzyme gene fragments were obtained from the 4-ABA-production-related gene expression plasmids constructed as shown in Table 2, and were introduced into the chromosome transfer plasmids described above. The 4-ABA-production-related gene chromosome transfer plasmids obtained are shown in Table 6.

TABLE 6

4-ABA-production-related gene chromosome transfer plasmids

| Gene source | Enzyme gene | SSI region | Chromosome transfer plasmid |
|---|---|---|---|
| *Escherichia coli* | pabC | SSI 2-2 | LKSani16 |
| *Escherichia coli* | pabC | SSI 3-3 | LKSani15 |
| *Corynebacterium callunae* | pabAB | SSI 7 | LKSani44 |
| *Corynebacterium callunae* | pabAB | SSI 8 | LKSani45 |
| *Corynebacterium callunae* | pabAB | SSI 10-2 | LKSani47 |
| *Corynebacterium callunae* | pabAB | SSI 6-2 | LKSani46 |
| *Escherichia coli* | aroG(S180F) | SSI 2-3 | LKSani21 |
| *Corynebacterium glutamicum* | aroC, aroK, aroB | SSI 9-4 | LKSani48 |
| *Corynebacterium glutamicum* | aroA | SSI 4-7 | LKSani22 |
| *Corynebacterium glutamicum* | aroD | SSI 10-3 | LKSani2 |
| *Corynebacterium glutamicum* | aroE | SSI 2-4 | LKSani3 |

(4) Construction of 4-ABA Producing Strains by Chromosome Gene Recombination

The markerless chromosome gene transfer vector pCRA725 is a plasmid that cannot be replicated in *Corynebacterium glutamicum* R. In a case of a single crossover strain in which crossover occurs at the SSI region introduced into the plasmid pCRA725 and the homologous region on the chromosome, the strain exhibits the kanamycin resistance due to the expression of the kanamycin-resistant gene on pCRA725, and the lethality in a sucrose-containing medium due to the expression of the sacR-sacB gene of the *Bacillus subtilis*. In contrast, in a case of a double crossover strain, the strain exhibits the kanamycin sensitivity due to the loss of the kanamycin-resistant gene on pCRA725, and the viability in a sucrose-containing medium due to the loss of the sacR-sacB gene. A markerless chromosome gene introduced strain, therefore, exhibits the kanamycin sensitivity and the viability in the sucrose-containing medium.

By the above-described method, the 4-ABA-production-related gene chromosome introduced strains were constructed by using the above-described 4-ABA-production-related gene chromosome transfer plasmids. This chromosome gene recombination is outlined in Table 7.

TABLE 7

| Construction of 4-ABA-production-related gene introduced strains by chromosome gene recombination | | | | |
|---|---|---|---|---|
| Constructed strain | Host strain | Recombinant plasmid | Chromosome transfer gene | Chromosome destroying gene |
| ESani12 | R | LKSani16 | pabC | |
| ESani29 | R | LKSani44 | pabAB | |
| ESani32 | ESani29 | LKSani45 | pabAB × 2 | |
| ESani34 | ESani32 | LKSani47 | pabAB × 3 | |
| ESani41 | ESani34 | LKSani46 | pabAB × 4 | |
| ESani13 | ESani12 | LKSani15 | pabC × 2 | |
| ESani16 | ESani13 | LKSphe21 | pabC × 2, aroG(S180F) | |
| ESani19 | ESani16 | LKSphe48 | pabC × 2, aroG(S180F), aroC, aroK, aroB | |
| ESani24 | ESani19 | LKSphe22 | pabC × 2, aroG(S180F), aroC, aroK, aroB, aroA | |
| ESani27 | ESani24 | LKSphe2 | pabC × 2, aroG(S180F), aroC, aroK, aroB, aroA, aroD | |
| ESani31 | ESani27 | LKSani3 | pabC × 2, aroG(S180F), aroC, aroK, aroB, aroA, aroD, aroE | |
| ESani33 | ESani31 | pCRA728 | pabC × 2, aroG(S180F), aroC, aroK, aroB, aroA, aroD, aroE | IdhA |

aroG: 3-deoxy-D-arabino-heptulosonate-7-phosphate (DAHP) synthase gene derived from *Escherichia coli* (here, SEQ ID NO. 112) in which the 180th serine was substituted with phenylalanine.

aroC: chorismiate synthase gene derived from *Corynebacterium glutamicum* aroK: shikimate kinase gene derived from *Corynebacterium glutamicum* aroB: 3-dehydroquinate synthase gene derived from *Corynebacterium glutamicum* aroA: 3-phosphoshikimate 1-carboxyvinyltransferase gene derived from *Corynebacterium glutamicum* (here, SEQ ID NO. 114)

aroD: 3-dehydroquinate dehydratase gene derived from *Corynebacterium glutamicum* (here, SEQ ID NO. 115)

aroE: shikimate dehydrogenase gene derived from *Corynebacterium glutamicum* (here, SEQ ID NO. 116)

ΔldhA: lactate dehydrogenase gene disruption (5) Construction of 4-ABA-Production Gene Expression Plasmid Introduced Strains The above-described pabAB gene expression plasmids were introduced into the pabC gene chromosome introduced strain (ESani12), and the pabC gene expression plasmids were introduced into the pabAB gene chromosome introduced strain (ESani41), whereby 4-ABA producing strains were constructed.

The plasmid introduced strains are outlined in Tables 8 and 9.

TABLE 8

| pabAB gene expression plasmid introduced strains | | | |
|---|---|---|---|
| Constructed strain | Host strain | Introduced plasmid | pabAB gene source |
| ANI 137 | ESani12 | Pani190 | *Corynebacterium efficiens* |
| ANI 138 | ESani12 | Pani199 | *Neurospora crassa* |
| ANI 139 | ESani12 | Pani192 | *Corynebacterium glutamicum* |
| ANI 140 | ESani12 | Pani198 | *Corynebacterium callunae* |
| ANI 152 | ESani12 | Pani206 | *Corynebacterium casei* |
| ANI 155 | ESani12 | Pani211 | *Rhodococcus erythropolis* |
| ANI 156 | ESani12 | Pani212 | *Rhodococcus opacus* |
| ANI 157 | ESani12 | Pani213 | *Corynebacterium terpenotabidum* |
| ANI 158 | ESani12 | Pani214 | *Corynebacterium argentoratense* |
| ANI 205 | ESani12 | Pani251 | *Corynebacterium ureicelerivorans* |

TABLE 9

| pabC gene expression plasmid introduced strains | | | |
|---|---|---|---|
| Constructed strain | Host strain | Introduced plasmid | pabC gene source |
| ANI 207 | ESani41 | Pani151 | *Escherichia coli* |
| ANI 208 | ESani41 | Pani159 | *Escherichia fergusonii* |
| ANI 209 | ESani41 | Pani161 | *Saccharophagus degradans* |
| ANI 210 | ESani41 | Pani231 | *Shewanella woodyi* |
| ANI 211 | ESani41 | Pani235 | *Arthrobacter phenanthrenivorans* |
| ANI 212 | ESani41 | Pani237 | *Anabaena variabilis* |
| ANI 213 | ESani41 | Pani240 | *Azotobacter vinelandii* |
| ANI 214 | ESani41 | Pani241 | *Ochrobactrum anthropi* |
| ANI 215 | ESani41 | Pani243 | *Clostridium beijerinckii* |
| ANI 216 | ESani41 | Pani245 | *Xenorhabdus bovienii* |
| ANI 217 | ESani41 | Pani246 | *Bacillus pseudofirmus* |
| ANI 218 | ESani41 | Pani247 | *Caulobacter crescentus* |
| ANI 219 | ESani41 | Pani248 | *Synechococcus* sp. |
| ANI 220 | ESani41 | Pani249 | *Bacteroides thraiotaomicron* |
| ANI 221 | ESani41 | Pani250 | *Ferrimonas balearica* |
| ANI 222 | ESani41 | Pani259 | *Escherichia coli* |

By introducing the pabAB expression plasmid (Pani198) into the 4-ABA-production-related gene introduced strains shown in Table 5, 4-ABA producing strains having an enhanced metabolic pathway were constructed. The 4-ABA producing strains having an enhanced metabolic pathway are outlined in Table 10.

TABLE 10

| 4-ABA producing strains having enhanced metabolic pathway | | | |
|---|---|---|---|
| Constructed strain | Host strain | Introduced plasmid | pabAB gene source |
| ANI 162 | ESani13 | Pani198 | *Corynebacterium callunae* |
| ANI 166 | ESani16 | Pani198 | *Corynebacterium callunae* |
| ANI 179 | ESani19 | Pani198 | *Corynebacterium callunae* |
| ANI 186 | ESani24 | Pani198 | *Corynebacterium callunae* |
| ANI 187 | ESani27 | Pani198 | *Corynebacterium callunae* |
| ANI 192 | ESani31 | Pani198 | *Corynebacterium callunae* |
| ANI 198 | ESani33 | Pani198 | *Corynebacterium callunae* |

By simultaneously introducing the pabA expression plasmid and the pabBC expression plasmid mentioned above into *Corynebacterium glutamicum* strain R, a 4-ABA producing strain was constructed. Further, by simultaneously introducing the pabAB expression plasmid and the pabBC expression plasmid mentioned above, a 4-ABA producing strain was constructed. The 4-ABA producing strains are outlined in Table 11.

*Corynebacterium glutamicum* ANI 198 was deposited in Incorporated Administrative Agency National institute of Technology and Evaluation, NITE Patent Microorganisms Depositary (2-5-8 Kazusakamatari, Kisarazu-shi, Chiba 292-0818 Japan) as an international depositary authority, under Accession Number NITE BP-02188 on Jan. 6, 2016. The strain is therefore available to the public.

TABLE 11 pabBC gene expression plasmid introduced strain

| Constructed strain | Host strain | Introduced plasmid 1 | Introduced plasmid 2 |
|---|---|---|---|
| ANI 123 | R | Pani187 | Pani171 |
| ANI 127 | R | Pani219 | Pani171 |

By simultaneously introducing the pabAB expression plasmid and the pabC expression plasmid mentioned above into *Corynebacterium glutamicum* strain R, a 4-ABA producing strain was constructed. Further, by simultaneously introducing the pabAB expression plasmid and the pabC expression plasmid mentioned above into *Escherichia coli* K-12 MG1655, a 4-ABA producing strain whose host was different was constructed. The 4-ABA producing strains are outlined in Table 12.

TABLE 12

4-ABA producing strains with different hosts

| Constructed strain | Host strain | Introduced plasmid 1 | Introduced plasmid 2 |
|---|---|---|---|
| ANI 109 | R | Pani198 | Pani191 |
| ANI 225 | *Escherichia coli* | Pani198 | Pani269 |

[Example 2] (Combination of pabAB and pabC)

Production Test in Test Tube (10 mL Scale)

By using strain ANI 198, which is a para-aminobenzoic acid producing strain, which was constructed on the basis of strain ESani 33 as a *Corynebacterium glutamicum* strain R in which the shikimiate pathway was enhanced (see Example 1 (Table 10)), experiments of producing para-aminobenzoic acid in an aerobic batch reaction using a test tube were carried out by the method described below.

Strain ANI 198 was applied to A-agar plate [obtained by dissolving the following in distilled water 1 L: $(NH_2)_2CO$ 2 g, $(NH_4)_2SO_4$ 7 g, $KH_2PO_4$ 0.5 g, $K_2HPO_4$ 0.5 g, $MgSO_4.7H_2O$ 0.5 g, 0.06% (w/v) $FeSO_4.7H_2O$+0.042% (w/v) $MnSO_4.2H_2O$ 1 ml, 0.02% (w/v) biotin solution 1 ml, 0.01% (w/v) thiamin solution 2 ml, yeast extract 2 g, vitamin assay casamino acid 7 g, agar 15 g] containing kanamycin of final concentration 50 μg/mL and 4% glucose, and was incubated at 33° C. for 15 hours in a dark place.

One platinum loop of strain ANI 198 grown on the above-described plate was inoculated in a test tube containing 10 ml of A-liquid medium [obtained by dissolving the following in distilled water 1 L: $(NH_2)_2CO$ 2 g, $(NH_4)_2SO_4$ 7 g, $KH_2PO_4$ 0.5 g, $K_2HPO_4$ 0.5 g, $MgSO_4.7H_2O$ 0.5 g, 0.06% (w/v) $FeSO_4.7H_2O$+0.042% (w/v) $MnSO_4.2H_2O$ 1 ml, 0.02% (w/v) biotin solution 1 ml, 0.01% (w/v) thiamin solution 2 ml, yeast extract 2 g, vitamin assay casamino acid 7 g] containing kanamycin of final concentration 50 μg/mL and 2% glucose. Aerobic shaking culture was carried out at 33° C. for 7 to 15 hours.

Each strain grown under the above-described conditions was suspended in 10 ml of A-liquid medium containing kanamycin of final concentration 50 μg/mL and 4% glucose so that the initial bacterial cell concentration $OD_{610}$=0.5. 200 mg of $CaCO_3$ was added thereto and aerobic shaking culture was carried out at 33° C. for 48 hours. The culture solution obtained after 48 hours was centrifuged (4° C., 15000×g, 5 minutes), whereby supernatant of culture was obtained. The concentration of metabolite in the supernatant of culture was analyzed by using a high-performance liquid chromatography system (Prominence HPLC (manufactured by Shimadzu Corporation), COSMOSIL Packed column 5C18-AR-II, separation using 20% methanol and 0.07% perchloric acid for the mobile phase). Consequently, this strain produced 40.1 mM of para-aminobenzoic acid after 48 hours.

Example 3

Experiments of Production of Para-Aminobenzoic Acid in Jar Fermenter Using *Corynebacterium glutamicum* Transformant (250 mL Scale)

(Combination of pabAB and pabC)

By using strain ANI 198, which is a para-aminobenzoic acid producing strain, which was constructed on the basis of strain ESani 22, as a *Corynebacterium glutamicum* strain R in which the shikimate pathway was enhanced (see Example 1 (Table 10)), experiments of producing para-aminobenzoic acid in an aerobic fed-batch reaction using a jar fermenter were carried out by the method described below.

Strain ANI 198 was inoculated in 20 ml of the A-liquid medium containing kanamycin of final concentration 50 μg/mL and 2% glucose, and thereafter, aerobic shaking culture was carried out at 33° C. for 18 hours.

Strain ANI 198 was inoculated in 100 ml of the A-liquid medium containing kanamycin of final concentration 50 μg/mL and 2% glucose, and thereafter, aerobic shaking culture was carried out at 33° C. for 12 hours.

Bacterial cells grown under the above-described conditions were collected by centrifugation (4° C., 3000×g, 10 minutes), bacterial cells thus obtained were suspended in 600 ml of a culture solution [obtained by dissolving the following in 1 L of distilled water: $(NH_4)_2SO_4$ 7 g, $KH_2PO_4$ 0.5 g, $K_2HPO_4$ 0.5 g, $MgSO_4.7H_2O$ 0.5 g, 0.06% (w/v) $FeSO_4.7H_2O$+0.042% (w/v) $MnSO_4.2H_2O$ 1 ml, 0.02% (w/v) biotin solution 25 μl, 0.01% (w/v) thiamin solution 2 ml, yeast extract 2 g, and vitamin assay casamino acid 7 g] containing kanamycin of final concentration 50 μg/mL, 6% glucose, and 5 g/L of an antifoam agent (DISFOAM CB-442) in a jar fermenter culture vessel having a capacity of 1000 ml so that $OD_{610}$=0.5, and aeration agitation culture was carried out by the 1000 ml capacity jar fermenter under the conditions of 33° C., pH 7.0 (controlled by adding 5.0 N ammonium hydroxide), aeration amount of 0.6 L/min (air, 1 vvm), and dissolved oxygen concentration (DO) 10% (with the saturated dissolved oxygen concentration under the atmospheric pressure being assumed to be 100%), for 18 hours.

Bacterial cells of the strain grown under the above-described conditions were collected by centrifugation (4° C., 5000×g, 10 minutes), and the bacterial cells thus obtained were washed with 0.9% sodium chloride aqueous solution once. The bacterial cells were suspended in 250 ml of a reaction solution [obtained by dissolving the following in 1 L of distilled water: $(NH_4)_2SO_4$ 7 g, $KH_2PO_4$ 0.5 g, $K_2HPO_4$ 0.5 g, $MgSO_4.7H_2O$ 0.5 g, 0.06% (w/v) $Fe_2SO_4.7H_2O$+0.042% (w/v) $MnSO_4.2H_2O$ 1 ml, 0.01% (w/v) thiamine solution 2 ml] containing 7.2% glucose so that 100 g of wet bacterial cells were contained per liter (10% of the medium volume in terms of weight of wet bacterial cells), and a para-aminobenzoic acid generating reaction was caused under the conditions of 33° C., pH 7.0 (controlled by adding 5.0 N ammonium hydroxide), aeration amount of 0.25 L/min (air, 1 vvm), DO 5%, by using the 1000 ml capacity jar fermenter. The glucose concentration in the reaction solution was monitored by using a glucose sensor (BF-5i, manufactured by Oji-keisoku.co.jp), and glucose was additionally added before it ran out. The concentration of metabolite in the supernatant of culture was analyzed by using the high-performance liquid chromatography system described above.

Figure 3:
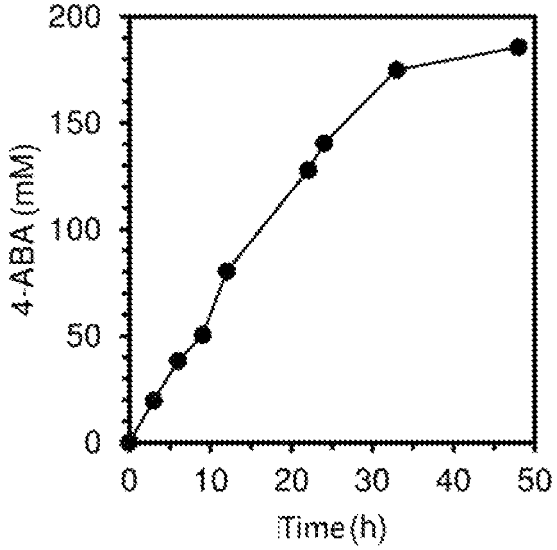
FIG. 3 illustrates changes with time of the production of para-aminobenzoic acid from glucose by a *Corynebacterium glutamicum* transformant in which pabAB and pabC were introduced.

The results are shown in FIG. 3. The strain ANI 198 produced 186 mM (25.5 g/l) of para-aminobenzoic acid by 48 hours after the start of the reaction (para-aminobenzoic acid production rate 3.9 mM/h). Further, no substantial growth of bacteria cells was observed during the reaction of producing para-aminobenzoic acid caused by the strain. These results indicate that the strain has extremely high para-aminobenzoic acid productivity in the reaction process without bacterial cell growth that uses an inorganic salt minimal medium. The para-aminobenzoic acid productivity of this strain significantly exceeded the productivity of *Escherichia coli* recombinant strain, 35 mM (4.8 g/L) in 48 hours (Patent Document 1, Non-patent Document 2), which is the highest productivity among the productivities by the processes of fermentation from saccharides that have been reported so far.

[Example 4] (Combination of pabA and pabBC)

Experiments of Production in Test Tube (10 mL Scale)

By using strain ANI 123, which is a para-aminobenzoic acid producing strain, which was constructed on the basis of a *Corynebacterium glutamicum* strain R (see Example 1 (Table 11)), experiments of producing para-aminobenzoic acid in an aerobic batch reaction using a test tube were carried out by the method described below.

Strain ANI 123 was applied to A-agar plate containing kanamycin of final concentration 50 μg/mL, 5 μg/mL chloramphenicol, and 4% glucose, and was incubated at 33° C. for 15 hours in a dark place.

One platinum loop of this strain grown on the above-described plate was inoculated in a test tube containing 10 ml of the A-liquid medium containing kanamycin of final concentration 50 μg/mL, 5 μg/mL chloramphenicol, and 2% glucose. Aerobic shaking culture was carried out at 33° C. for 7 to 15 hours.

Each strain grown under the above-described conditions was suspended in 10 ml of the A-liquid medium containing kanamycin of final concentration 50 μg/mL, 5 μg/mL chloramphenicol, and 4% glucose so that the initial bacterial cell concentration $OD_{610}$=0.5. 200 mg of $CaCO_3$ was added thereto and aerobic shaking culture was carried out at 33° C. for 48 hours. The culture solution obtained after 48 hours was centrifuged (4° C., 15000×g, 5 minutes), and the supernatant of culture obtained was subjected to quantitative analysis of para-aminobenzoic acid, using the above-mentioned high-performance liquid chromatography system. Consequently, this strain produced 16.6 mM of para-aminobenzoic acid after 48 hours.

[Example 5] (Combination of pabAB and pabBC)

Production Test in Test Tube (10 mL Scale)

By using strain ANI 127, which is a para-aminobenzoic acid producing strain, which was constructed on the basis of a *Corynebacterium glutamicum* strain R (see Example 1 (Table 11)), experiments of producing para-aminobenzoic acid in an aerobic batch reaction using a test tube were carried out by the method described below.

Strain ANI 127 was applied to A-agar plate containing kanamycin of final concentration 50 μg/mL, 5 μg/mL chloramphenicol, and 4% glucose, and was incubated at 33° C. for 15 hours in a dark place.

One platinum loop of this strain grown on the above-described plate was inoculated in a test tube containing 10 ml of the A-liquid medium containing kanamycin of final concentration 50 μg/mL, 5 μg/mL chloramphenicol, and 2% glucose. Aerobic shaking culture was carried out at 33° C. for 7 to 15 hours.

Each strain grown under the above-described conditions was suspended in 10 ml of the A-liquid medium containing kanamycin of final concentration 50 μg/mL, 5 μg/mL chloramphenicol, and 4% glucose so that the initial bacterial cell concentration $OD_{610}$=0.5. 200 mg of $CaCO_3$ was added thereto and aerobic shaking culture was carried out at 33° C. for 48 hours. The culture solution obtained after 48 hours was centrifuged (4° C., 15000×g, 5 minutes), and the supernatant of culture obtained was subjected to quantitative analysis of para-aminobenzoic acid, using the above-mentioned high-performance liquid chromatography system. Consequently, this strain produced 7.6 mM of para-aminobenzoic acid after 48 hours.

Example 6

Influences on Para-Aminobenzoic Acid Production by pabAB Derived from Various Living Things To examine what effects the introduction of the gene pabAB causes in the production of para-aminobenzoic acid by *Corynebacterium glutamicum* transformants, para-aminobenzoic acid productivities of a plurality of types of strains that were constructed on the basis of strain ESani 12 were compared. Each strain was applied to the above-described A-agar plate containing kanamycin of final concentration 50 μg/mL and 4% glucose, and it was incubated at 33° C. for 15 hours in a dark place.

One platinum loop of each strain grown on the above-described plate was inoculated in a test tube containing 10 ml of the A-liquid medium containing kanamycin of final concentration 50 μg/mL and 2% glucose. Aerobic shaking culture was carried out at 33° C. for 7 to 15 hours.

Each strain grown under the above-described conditions was inoculated in 10 ml of the A-liquid medium containing kanamycin of final concentration 50 μg/mL and 4% glucose so that the initial bacterial cell concentration $OD_{610}$=0.5. 200 mg of $CaCO_3$ was added thereto and aerobic shaking culture was carried out at 33° C. for 48 hours. The culture solution obtained after 48 hours was centrifuged (4° C., 15000×g, 5 minutes), and the supernatant of culture obtained was subjected to quantitative analysis of para-aminobenzoic acid, using the above-mentioned high-performance liquid chromatography system.

The results are shown in Table 13. These results indicate that the para-aminobenzoic acid production amount increased owing to high expression of pabAB derived from the genus *Corynebacterium*, and that a particularly large production amount was exhibited particularly in a case where pabAB derived from *Corynebacterium callunae* was used.

TABLE 13

Comparison of amounts of produced para-aminobenzoic acid in case of different pabAB origins

| Strain | pabAB gene source | Concentration of produced 4-ABA (mM) |
|---|---|---|
| ANI 137 | *Corynebacterium efficiens* | 20.3 |
| ANI 138 | *Neurospora crassa* | 10.0 |
| ANI 139 | *Corynebacterium glutamicum* | 10.5 |
| ANI 140 | *Corynebacterium callunae* | 24.0 |
| ANI 152 | *Corynebacterium casei* | 18.0 |
| ANI 155 | *Rhodococcus erythropolis* | 0.8 |
| ANI 156 | *Rhodococcus opacus* | 10.8 |
| ANI 157 | *Corynebacterium terpenotabidum* | 5.6 |
| ANI 158 | *Corynebacterium argentoratense* | 7.0 |
| ANI 205 | *Corynebacterium ureicelerivorans* | 9.9 |

As shown in Table 13, the 4-ABA production amount significantly varied depending on the origin of pabAB. pabAB derived from the genus *Corynebacterium* generally provided excellent 4-ABA production. In particular, transformants into which pabAB derived from *Corynebacterium efficiens, Corynebacterium callunae*, or *Corynebacterium casei* exhibited high 4-ABA production.

Example 7

Influences on Para-Aminobenzoic Acid Production by pabC Derived from Various Living Things To examine what effects the introduction of the gene pabC causes in the production of para-aminobenzoic acid by *Corynebacterium glutamicum* transformants, para-aminobenzoic acid productivities of a plurality of types of strains that were constructed on the basis of strain ESani 41 were compared in the same manner as in Example 6. The results are shown in Table 14.

TABLE 14

Comparison of amounts of produced para-aminobenzoic acid in case of different pabC origins

| Strain | pabC gene source | Concentration of produced 4-ABA (mM) |
|---|---|---|
| ANI 207 | *Escherichia coli* | 13.1 |
| ANI 208 | *Escherichia fergusonii* | 12 |
| ANI 209 | *Saccharophagus degradans* | 11.1 |
| ANI 210 | *Shewanella woodyi* | 0.5 |
| ANI 211 | *Corynebacterium callunae* | 3.8 |
| ANI 212 | *Arthrobacter phenanthrenivorans* | 11.4 |
| ANI 213 | *Anabaena variabilis* | 12.4 |
| ANI 214 | *Azotobacter vinelandii* | 11.4 |
| ANI 215 | *Ochrobactrum anthropi* | 10.7 |
| ANI 216 | *Clostridium beijerinckii* | 5.7 |
| ANI 217 | *Xenorhabdus bovienii* | 12.7 |
| ANI 218 | *Bacillus pseudofirmus* | 10.3 |
| ANI 219 | *Caulobacter crescentus* | 9.7 |
| ANI 220 | *Synechococcus* sp. | 9.7 |
| ANI 221 | *Bacteroides thraiotaomicron* | 9.8 |
| ANI 222 | *Ferrimonas balearica* | 10.1 |

As shown in Table 14, the high expression of pabC derived from the genus *Escherichia*, the genus *Saccharophagus*, the genus *Arthrobacter*, the genus *Anabaena*, the genus *Ochrobactrum*, the genus *Xenorhabdus*, the genus *Bacillus*, or the genus *Ferrimonas* caused increases in the production of para-aminobenzoic acid.

Example 8

Influences on Para-Aminobenzoic Acid Productivity by Enhancement of Metabolic Pathway and Cutoff of by-Product Formation Pathway To examine the effects of optimization of the metabolic pathway in the para-aminobenzoic acid production by *Corynebacterium glutamicum* transformants, para-aminobenzoic acid productivities of a plurality of types of strains were compared in the same manner as in Example 6.

Here, effects in a case where a gene on the shikimate pathway was added onto the chromosome, and effects in a case where the by-product formation pathway gene was disrupted, were compared. The results are shown in Table 15.

TABLE 15

Comparison of amounts of produced para-aminobenzoic acid of strains with enhanced shikimiate pathway and by-product formation pathway cutoff

| Strain | Concentration of produced 4-ABA (mM) |
|---|---|
| ANI 140 | 24.0 |
| ANI 162 | 24.2 |
| ANI 166 | 26.3 |
| ANI 179 | 36.8 |
| ANI 186 | 37.5 |
| ANI 187 | 37.1 |
| ANI 192 | 39.5 |
| ANI 198 | 40.1 |

As shown in Table 15, the amount of produced para-aminobenzoic acid was increased by enhancing the shikimate pathway and cutting off the by-product formation pathway.

Example 9

Influences of Host on 4-ABA Productivity (*Escherichia coli* and Coryneform Bacterium)

To examine how the 4-ABA productivity varies depending on the host, pabAB and pabC derived from the same species were introduced into a coryneform bacterium and *Escherichia coli*, and 4-ABA productivities were compared. Here, pabAB derived from *Corynebacterium callunae*, and pabC derived from *Escherichia coli*, were used.

Strain ANI 109, which was constructed on the basis of a wild strain of a coryneform bacterium (Example 1 (Table 12), was applied to A-agar plate containing kanamycin of final concentration 50 μg/mL, 5 μg/mL chloramphenicol, and 4% glucose, and was incubated at 33° C. for 15 hours in a dark place. One platinum loop of each strain grown on the above-described plate was inoculated in a test tube containing 10 ml of the A-liquid medium containing kanamycin of final concentration 50 μg/mL, 5 μg/mL chloramphenicol, and 2% glucose. Aerobic shaking culture was carried out at 33° C. for 7 to 15 hours.

Each strain grown under the above-described conditions was inoculated in 10 ml of the A-liquid medium containing kanamycin of final concentration 50 μg/mL, 5 μg/mL chloramphenicol, and 4% glucose so that the initial bacterial cell concentration $OD_{610}$=0.5. 200 mg of $CaCO_3$ was added thereto and aerobic shaking culture was carried out at 33° C. for 48 hours. The culture solution obtained after 48 hours was centrifuged (4° C., 15000×g, 5 minutes), and the supernatant of culture obtained was subjected to quantitative analysis of para-aminobenzoic acid, using the above-mentioned high-performance liquid chromatography system.

Strain ANI 225, which was constructed on the basis of a wild strain of an *Escherichia coli* K-12 MG1655 (Example 1 (Table 12), was applied to LB-agar plate containing kanamycin of final concentration 50 μg/mL and 50 μg/mL chloramphenicol, and was incubated at 33° C. for 15 hours in a dark place. One platinum loop of each strain grown on the above-described plate was inoculated in a test tube containing 10 ml of the above-described LB-liquid medium containing kanamycin of final concentration 50 μg/mL, 50 μg/mL chloramphenicol, and 2% glucose. Aerobic shaking culture was carried out at 37° C. for 7 to 15 hours.

Each strain grown under the above-described conditions was inoculated in 10 ml of the above-described LB-liquid medium containing kanamycin of final concentration 50 μg/mL, 50 μg/mL chloramphenicol, and 4% glucose so that the initial bacterial cell concentration $OD_{610}$=0.5. 200 mg of $CaCO_3$ was added thereto and aerobic shaking culture was carried out at 37° C. for 48 hours. The culture solution obtained after 48 hours was centrifuged (4° C., 15000×g, 5 minutes), and the supernatant of culture obtained was subjected to quantitative analysis of para-aminobenzoic acid, using the above-mentioned high-performance liquid chromatography system.

As a result, the concentration of 4-ABA contained in the supernatant of 48-hour culture of strain ANI 109 constructed on the basis of a coryneform bacterium as a host was 16.2 mM. In contrast, in the case of ANI 225 constructed on the basis of *Escherichia coli* as a host, the concentration of 4-ABA was below the detection limit.

INDUSTRIAL APPLICABILITY

By the process of the present invention, 4-ABA or a salt thereof can be produced from glucose and the like with a practical efficiency by using microorganisms.

The invention claimed is:

1. A transformant having 4-aminobenzoic acid producing ability, the transformant being obtained by introducing a gene that encodes a two-component enzyme having para-aminobenzoate synthase component I activity and para-aminobenzoate synthase component II activity, which is a gene pabAB, and a gene that encodes an enzyme having 4-amino-4-deoxy chorismate lyase activity, which is a gene pabC, into *Corynebacterium glutamicum* as a host, wherein the pabAB is a gene of *Corynebacterium callunae, Corynebacterium efficiens*, or *Corynebacterium casei*, and wherein the pabC is a gene of *Escherichia coli, Escherichia fergusonii, Saccharophagus degradans, Arthrobacter phenanthrenivorans, Anabaena variabilis, Azotobacter vinelandii, Ochrobactrum anthropi, Xenorhabdus bovienii, Bacillus pseudofirmus, Caulobacter crescentus, Synechococcus* sp., *Bacteroides thetaiotaomicron*, or *Ferrimonas balearica.*

2. The transformant according to claim 1, wherein *Corynebacterium glutamicum Corynebacterium glutamicum* as a host is *Corynebacterium glutamicum* R (FERM BP-18976), ATCC13032, or ATCC 13869.

3. A *Corynebacterium glutamicum* transformant ANI198 (NITE BP-02188).

4. A method for producing 4-aminobenzoic acid or a salt thereof, the process comprising the step of culturing the transformant according to claim 1 in a reaction solution containing a saccharide so that the transformant produces 4-aminobenzoic acid or a salt thereof.

5. The method according to claim 4, wherein the transformant is cultured under conditions that are aerobic and under which the transformant does not grow.

6. The transformant according to claim 1, wherein a gene that encodes an enzyme having 3-deoxy-D-arabino-heptulosonate-7-phosphate synthase is further introduced into the *Corynebacterium glutamicum* as a host.

7. The transformant according to claim 1, wherein a gene aroA, a gene aroB, a gene aroC, a gene aroD, a gene aroE, a gene aroG, and a gene aroK is further introduced into the *Corynebacterium glutamicum* as a host.

8. The transformant according to claim 1, wherein lactate dehydrogenase gene is disrupted.

9. The transformant according to claim 1, wherein the gene pabAB:

(a) consists of a base sequence of any one of SEQ ID NOs:18 to 20;

(b) consists of a base sequence having 90% or more of identity with any one of SEQ ID NOs:18 to 20, and encodes a polypeptide having para-aminobenzoate synthase component I activity and para-aminobenzoate synthase component II activity.

10. The transformant according to claim 1, wherein the gene pabC:

(c) consists of a base sequence of any one of SEQ ID NOs:2 to 4, 6 to 9 and 11 to 16;

(d) consists of a base sequence having 90% or more of identity with any one of SEQ ID NOs:2 to 4, 6 to 9 and 11 to 16, and encodes a polypeptide having 4-amino-4-deoxychorismate lyase activity.

11. The transformant according to claim 1, wherein a gene aroG is further introduced into the *Corynebacterium glutamicum* as a host.

12. The transformant according to claim 1, wherein a gene aroB, a gene aroC, a gene aroG, and a gene aroK is further introduced into the *Corynebacterium glutamicum* as a host.

13. The transformant according to claim 1, wherein a gene aroA, a gene aroB, a gene aroC, a gene aroG, and a gene aroK is further introduced into the *Corynebacterium glutamicum* as a host.

14. The transformant according to claim 1, wherein a gene aroA, a gene aroB, a gene aroC, a gene aroD, a gene aroG, and a gene aroK is further introduced into the *Corynebacterium glutamicum* as a host.

* * * * *